United States Patent
Yamamoto et al.

(10) Patent No.: US 11,390,889 B2
(45) Date of Patent: Jul. 19, 2022

(54) METHOD FOR MANUFACTURING 1,3-PROPANEDIOL

(71) Applicants: Green Earth Institute Co., Ltd., Tokyo (JP); Natural Beauty, Limited, Tokyo (JP)

(72) Inventors: Keisuke Yamamoto, Chiba (JP); Atsunari Tsuchisaka, Chiba (JP); Shuhei Nakane, Chiba (JP); Toru Nakayashiki, Chiba (JP)

(73) Assignees: Green Earth Institute Co., Ltd., Tokyo (JP); Natural Beauty, Limited, Tokyo (JP)

( * ) Notice: Subject to any disclaimer, the term of this patent is extended or adjusted under 35 U.S.C. 154(b) by 0 days.

(21) Appl. No.: 16/620,881

(22) PCT Filed: Oct. 30, 2018

(86) PCT No.: PCT/JP2018/040416
§ 371 (c)(1),
(2) Date: Jun. 23, 2021

(87) PCT Pub. No.: WO2020/090017
PCT Pub. Date: May 7, 2020

(65) Prior Publication Data
US 2021/0324424 A1    Oct. 21, 2021

(51) Int. Cl.
| | |
|---|---|
| C12P 7/18 | (2006.01) |
| C12N 15/52 | (2006.01) |
| C12N 9/02 | (2006.01) |
| C12N 9/16 | (2006.01) |
| C12N 9/90 | (2006.01) |
| C12N 9/88 | (2006.01) |

(52) U.S. Cl.
CPC .................. *C12P 7/18* (2013.01); *C12N 9/88* (2013.01); *C12N 9/90* (2013.01); *C12N 15/52* (2013.01); *C12Y 101/05006* (2013.01); *C12Y 102/01003* (2013.01); *C12Y 104/01001* (2013.01)

(58) Field of Classification Search
CPC ... C12N 9/88; C12N 9/93; C12N 9/16; C12N 9/18; C12N 9/0028; C12P 7/18; C12Y 101/05006; C12Y 102/01003; C12Y 401/01001; C12Y 102/01
USPC .......... 435/158, 252.33, 135, 189, 190, 155
See application file for complete search history.

(56) References Cited

U.S. PATENT DOCUMENTS

| | | | |
|---|---|---|---|
| 8,647,847 B2 | 2/2014 | Nonaka | |
| 9,926,577 B2 | 3/2018 | Feldman et al. | |
| 2015/0368677 A1 | 12/2015 | Furutani et al. | |
| 2016/0257976 A1 | 9/2016 | Lee et al. | |

FOREIGN PATENT DOCUMENTS

| | | |
|---|---|---|
| CN | 103025877 | 4/2013 |
| CN | 103917651 | 7/2014 |
| CN | 104109651 | 10/2014 |
| CN | 107384846 | 11/2017 |
| JP | H07107968 | 4/1995 |
| JP | H10507082 | 7/1998 |
| JP | 2001504338 | 4/2001 |
| JP | 2013529924 | 7/2013 |
| JP | 2014525239 | 9/2014 |
| JP | 2018519829 | 7/2018 |
| WO | 9635799 | 11/1996 |
| WO | 9821341 | 5/1998 |
| WO | 2010141920 | 12/2010 |
| WO | 2012004247 | 1/2012 |
| WO | 2012018624 | 2/2012 |
| WO | 2013025945 | 2/2013 |
| WO | 2013036764 | 3/2013 |
| WO | 2014071286 | 5/2014 |
| WO | 2014112627 | 7/2014 |
| WO | 2015017721 | 2/2015 |
| WO | 2017011915 | 1/2017 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Wu Congyi et al., "Research Progress in Preparation of 1,3-Propanediol", Journal of Molecular Catalysis (China), with English translation thereof, Jan. 2012, pp. 1-18.
Jaehyeon Lee et al., "Production of 1,3-Propandiol from Glucose by Recombinant *Escherichia coli* BL21(DE3).", Biotechnology and Bioprocess Engineering, May 12, 2018, pp. 1-1.
Office Action of China Counterpart Application, with English translation thereof, dated Jul. 19, 2021, pp. 1-13.
"International Search Report (Form PCT/ISA/210) of PCT/JP2018/040416," dated Jan. 29, 2019, pp. 1-4.
"Office Action of Japan Counterpart Application", dated Jul. 16, 2019, with English translation thereof, p. 1-p. 8.
"Office Action of Japan Counterpart Application", dated Nov. 5, 2019, with English translation thereof, p. 1-p. 6.
"Written Opinion of the International Searching Authority (Form PCT/ISA/237) of PCT/JP2018/040416," dated Jan. 29, 2019, with English translation thereof, pp. 1-8.

(Continued)

*Primary Examiner* — Robert B Mondesi
*Assistant Examiner* — Mohammad Y Meah
(74) *Attorney, Agent, or Firm* — JCIPRNET

(57) ABSTRACT

A method for manufacturing 1,3-propanediol includes culturing, in the presence of a saccharide and formaldehyde to produce 1,3-propanediol, a microorganism having the following genes: (a) a first gene encoding an enzyme that catalyzes an aldol reaction between pyruvic acid and aldehydes; (b) a second gene encoding an enzyme that catalyzes a decarboxylation reaction of α-keto acids; and (c) a third gene encoding an enzyme that catalyzes a reduction reaction of aldehydes, is provided.

15 Claims, 1 Drawing Sheet

Specification includes a Sequence Listing.

(56) References Cited

OTHER PUBLICATIONS

Feiyan Liang, et al., "Engineered cyanobacteria with enhanced growth show increased ethanol production and higher biofuel to biomass ratio," Metabolic Engineering, vol. 46, Feb. 2018, pp. 51-59.

Ferenci,T., et al., "predicted 2,4-dihydroxyhept-2-ene-1,7-dioic acid aldolase [*Escherichia coli* BW2952]," accessed Dec. 2019, Available at: https://www.ncbi.nlm.nih.gov/protein/ACR64091.1.

Yujin Cao et al., "Biotechnological production of 1,2,4-butanetriol: An efficient process to synthesize energetic material precursor from renewable biomass", Scientific Reports, vol. 5, Dec. 2015, pp. 1-9.

Bin Zhuge et al., "Expression of 1,3-propanediol oxidoreductase and its isoenzyme in Klebsiella pneumoniae for bioconversion of glycerol into 1,3-propanediol", Appl Microbiol Biotechnol, vol. 87, May 2010, pp. 2177-2184.

Wang Fenghuan et al., "High-level expression of the 1,3-propanediol oxidoreductase from Klebsiella pneumoniae in *Escherichia coli*", Molecular Biotechnology, vol. 31, Nov. 2005, pp. 211-219.

Anita Loeschcke et al., "Pseudomonas putida—a versatile host for the production of natural products", Appl Microbiol Biotechnol, vol. 99, Jun. 2015, pp. 6197-6214.

"Office Action of China Counterpart Application" with English translation thereof, dated Apr. 24, 2022, p. 1-p. 7.

* cited by examiner

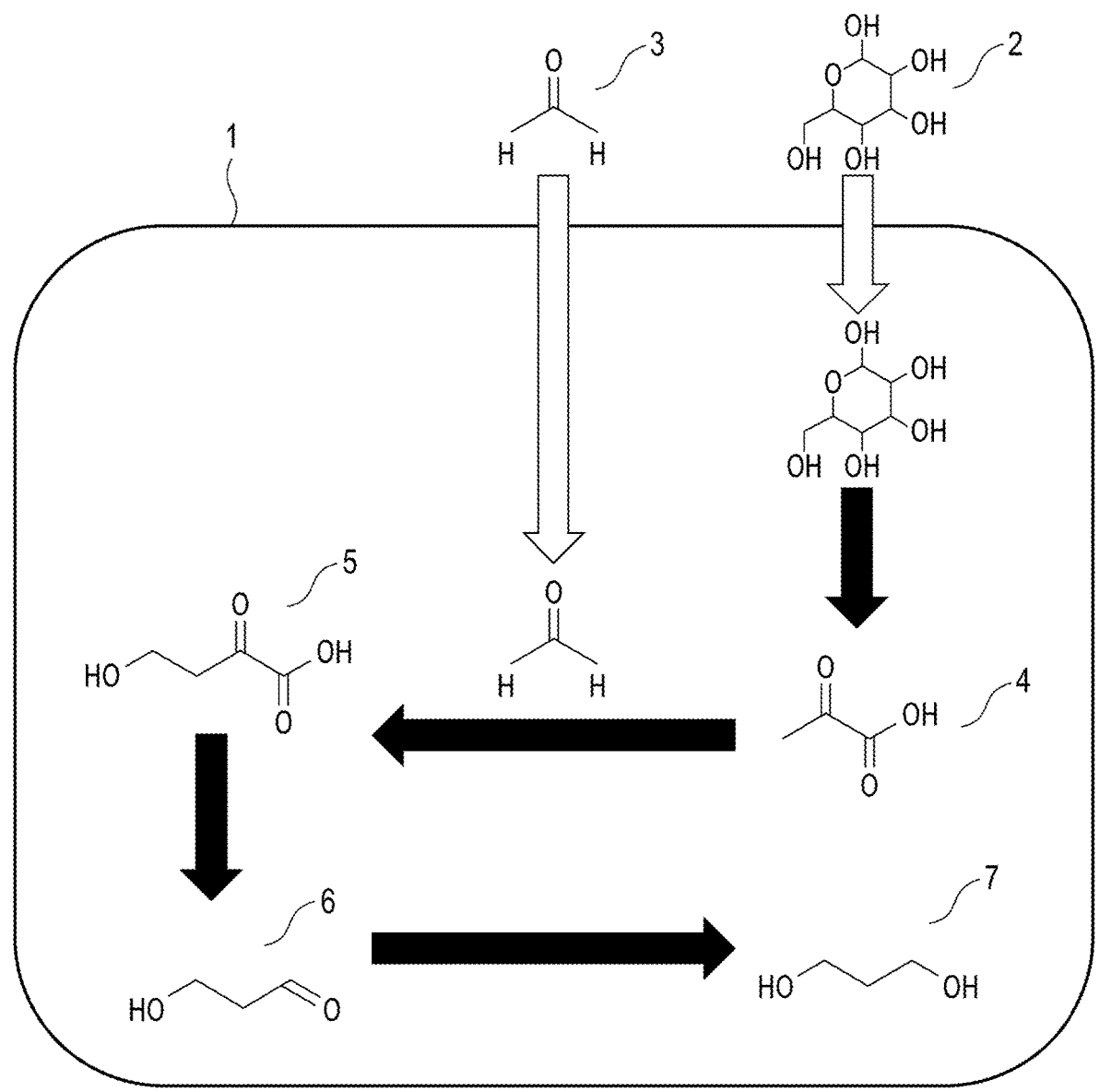

METHOD FOR MANUFACTURING 1,3-PROPANEDIOL

CROSS-REFERENCE TO RELATED APPLICATION

This application is a 371 of international application of PCT application serial no. PCT/JP2018/040416, filed on Oct. 30, 2018. The entirety of each of the above-mentioned patent application is hereby incorporated by reference herein and made a part of this specification.

TECHNICAL FIELD

The present invention relates to a method for manufacturing 1,3-propanediol.

BACKGROUND ART

Currently, instead of petroleum resources which are considered the cause of global warming, it is strongly desired to produce chemical products using biological resources, which are renewable resources, as raw materials. For this reason, for the purpose of producing chemical products from biological materials such as saccharides, research has been actively conducted to produce chemical products used for industrial raw materials, fuel, feedstocks, food additives, and the like using microorganisms and their transformants. For example, it has been reported that organic compounds such as alcohols or amino acids can be manufactured from saccharides using a transformant of yeast or *Escherichia coli* (refer to U.S. Pat. Nos. 9,926,577 and 8,647,847).

SUMMARY OF INVENTION

Technical Problem

An objective of the present invention is to provide a novel method for producing an organic compound.

Production of chemical products using microorganisms is generally limited to microbial metabolites as production targets. In addition, even in the case of microbial metabolites, there are many microbial metabolites that are difficult to produce due to lack of energy in the microbial metabolic system and imbalance in the oxidation-reduction balance. One effective approach for solving such problems is to create a transformant. However, the inventors of the present invention consider that when attempting to solve the problems only by this method, it may take a lot of time to develop bacterial cells capable of producing a target compound. Meanwhile, they consider that, in the future, it is necessary to produce various compounds other than microbial metabolites from biological materials. Accordingly, the inventors of the present invention have examined development of a new process in which production of useful substances is not simply depend on creation of a transformant of microorganisms.

Solution to Problem

As a result of intensive studies conducted by the inventors of the present invention, the inventors have found a production process in which 1,3-propanediol can be obtained by culturing a microorganism having a specific gene in the presence of formaldehyde, and therefore have completed the present invention.

According to the present invention, the following method is provided.

A method for manufacturing 1,3-propanediol, including culturing, in the presence of a saccharide and formaldehyde to produce 1,3-propanediol, a microorganism having the following genes:

(a) a first gene encoding an enzyme that catalyzes an aldol reaction between pyruvic acid and aldehydes;

(b) a second gene encoding an enzyme that catalyzes a decarboxylation reaction of α-keto acids; and (c) a third gene encoding an enzyme that catalyzes a reduction reaction of aldehydes.

According to the present invention, a method for manufacturing 1,3-propanediol using a microorganism is provided.

BRIEF DESCRIPTION OF DRAWINGS

FIG. 1 is a schematic diagram showing a process in which a microorganism produces 1,3-propanediol.

DESCRIPTION OF EMBODIMENTS

Hereinafter, the present invention will be described in detail. The following description is intended to explicate the present invention and is not intended to limit the present invention.

A method for manufacturing 1,3-propanediol includes culturing, in the presence of a saccharide and formaldehyde to produce 1,3-propanediol, a microorganism having the following genes:

(a) a first gene encoding an enzyme that catalyzes an aldol reaction between pyruvic acid and aldehydes;

(b) a second gene encoding an enzyme that catalyzes a decarboxylation reaction of α-keto acids; and (c) a third gene encoding an enzyme that catalyzes a reduction reaction of aldehydes.

In the following description, the microorganism having the first, second, and third genes is also referred to as a "1,3-propanediol-producing microorganism." The 1,3-propanediol-producing microorganism may be a microorganism inherently having the first, second, and third genes, or may be a microorganism obtained by transforming a host with the first, second, and third genes. Hereinafter, the case where the 1,3-propanediol-producing microorganism is a transformant will be described as an example.

(1.) Transformant (1.1) Host

Any host can be used as a host. As the host, for example, it is possible to use yeasts and bacteria, more specifically, it is possible to use aerobic bacteria, and even more specifically, it is possible to use coryneform bacteria, *Escherichia coli*, or *Vibrio natriegens*. The host is preferably coryneform bacteria.

Coryneform bacteria are a group of microorganisms defined in Bergey's Manual of Determinative Bacteriology, Vol. 8, 599 (1974), and are not particularly limited as long as they grow in general aerobic conditions. Specific examples thereof include bacteria belonging to the genus *Corynebacterium*, bacteria belonging to the genus *Brevibacterium*, bacteria belonging to the genus *Arthrobacter*, bacteria belonging to the genus *Mycobacterium*, bacteria belonging to the genus *Micrococcus*, and the like. Among the coryneform bacteria, bacteria belonging to the genus *Corynebacterium* are preferable.

Examples of bacteria belonging to the genus *Corynebacterium* includes *Corynebacterium glutamicum*, *Corynebac-*

*terium efficiens*, *Corynebacterium ammoniagenes*, *Corynebacterium halotolerance*, *Corynebacterium alkanolyticum*, and the like. Among them, *Corynebacterium glutamicum* is preferable in terms of high productivity of 1,3-propanediol. Preferable bacterial strains thereof include the strains ATCC 13032, ATCC 13869, ATCC 13058, ATCC 13059, ATCC 13060, ATCC 13232, ATCC 13286, ATCC 13287, ATCC 13655, ATCC 13745, ATCC 13746, ATCC 13761, ATCC 14020, ATCC 31831, MJ-233 (FERM BP-1497), MJ-233AB-41 (FERM BP-1498), and the like. Among them, the strains ATCC 13032 and ATCC 13869 are preferable.

According to molecular biology classification, bacterial names of coryneform bacteria such as *Brevibacterium flavum*, *Brevibacterium lactofermentum*, *Brevibacterium divaricatum*, and *Corynebacterium lilium* are unified by being classified as *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int J Syst Bacteriol. 41: 255-260. (1991), Kazuo Komagata et al., Classification of Coryneform Bacteria, Fermentation and Industry, 45: 944-963 (1987)).

The strain ATCC 13869 of *Brevibacterium lactofermentum*, the strains MJ-233 (FERM BP-1497) and MJ-233AB-41 of *Brevibacterium flavum* (FERM BP-1498), and the like in the old classification are also suitable *Corynebacterium glutamicum*.

Examples of the genus *Brevibacterium* include *Brevibacterium ammoniagenes* (for example, the strain ATCC 6872) and the like.

Examples of the genus *Arthrobacter* include *Arthrobacter globiformis* (for example, the strains ATCC 8010, ATCC 4336, ATCC 21056, ATCC 31250, ATCC 31738, and ATCC 35698), and the like.

Examples of the genus *Mycobacterium* include *Mycobacterium bovis* (for example, the strains ATCC 19210 and ATCC 27289), and the like.

Examples of the genus *Micrococcus* include *Micrococcus freudenreichii* (for example, No. 239 strain (FERM P-13221)), *Micrococcus luteus* (for example, No. 240 strain (FERM P-13222)), *Micrococcus ureae* (for example, the strain IAM1010), *Micrococcus roseus* (for example, the strain IF03964), and the like.

Next, the first, second, and third genes to be introduced into a host will be described.

(1.2) First Gene

The first gene encodes an "enzyme that catalyzes an aldol reaction between pyruvic acid and aldehydes." The "enzyme that catalyzes an aldol reaction between pyruvic acid and aldehydes" refers to an enzyme having an activity of 10 mU/mg protein or more when measured using an enzymatic reaction solution containing purified proteins, pyruvic acid (an initial substrate concentration 1 mM), and aldehydes (an initial substrate concentration 1 mM) as an enzymatic reaction solution according to a measurement method to be described later. An aldehyde in the "enzyme that catalyzes an aldol reaction between pyruvic acid and aldehydes" is, for example, formaldehyde. The "enzyme that catalyzes an aldol reaction between pyruvic acid and aldehydes" is, for example, an aldolase.

The first gene may be a gene encoding an aldolase to be exemplified below.

(a1) 2-Dehydro-3-deoxy-phosphogluconate aldolase (EC number: 4.1.2.14), (a2) 2-Dehydro-3-deoxy-6-phosphogluconate aldolase (EC number: 4.1.2.55), (a3) 4-Hydroxy-2-oxoglutarate aldolase (EC number: 4.1.3.16), (a4) (4S)-4-Hydroxy-2-oxoglutarate aldolase (EC number; 4.1.3.42), (a5) 2-Dehydro-3-deoxy-D-pentonate aldolase (EC number: 4.1.2.28), (a6) 2-Dehydro-3-deoxy-D-gluconate aldolase (EC number: 4.1.2.51), (a7) 3-Deoxy-D-manno-octulosonate aldolase (EC number: 4.1.2.23), (a8) 4-Hydroxyl-2-oxovalerate aldolase (EC number: 4.1.3.39), (a9) 4-(2-Carboxyphenyl)-2-oxobut-3-enoate aldolase (EC number: 4.1.2.34), (a10) 4-Hydroxy-2-oxoheptanedioate aldolase (EC number: 4.1.2.52), (a11) 2-Dehydro-3-deoxyglucarate aldolase (EC number: 4.1.2.20), (a12) 2-Keto-3-deoxy-L-rhamnonate aldolase (EC number: 4.1.2.53), (a13) 4-Hydroxyl-4-methyl-2-oxoglutarate aldolase (EC number: 4.1.3.17), and (a14) 4-Hydroxy-2-oxohexanoate aldolase (EC number: 4.1.3.43).

Examples of aldolases included in (a1), (a2), (a3), and (a4) include an eda protein. The eda protein is preferably derived from *Escherichia coli*.

Examples of aldolases included in (a2) include a dgoA protein. The dgoA protein is preferably derived from *Escherichia coli*.

Examples of aldolases included in (a5) include a yjhH protein. The yjhH protein is preferably derived from *Escherichia coli*.

Examples of aldolases included in (a6) include a yagE protein. The yagE protein is preferably derived from *Escherichia coli*.

Examples of aldolases included in (a7) include a nanA protein. The nanA protein is preferably derived from *Escherichia coli*.

Examples of aldolases included in (a8) include an mhpE protein. The mhpE protein is preferably derived from *Escherichia coli*. When the first gene is an mhpE gene, the mhpE gene may be introduced into a host in a state of being linked to an mhpF gene.

Examples of aldolases included in (a8) and (a10) include an hpaI protein. The hpaI protein is preferably derived from *Escherichia coli*.

Examples of aldolases included in (a8) and (a14) include a bphI protein. The bphI protein is preferably derived from *Burkholderia xenovorans*. When the first gene is a bphI gene, the bphI gene may be introduced into a host in a state of being linked to a bphJ gene.

Examples of aldolases included in (a9) include a phdJ protein. The phdJ protein is preferably derived from bacteria belonging to *Nocardioides* sp.

Examples of aldolases included in (a11) include a garL protein. The garL protein is preferably derived from *Escherichia coli*.

Examples of aldolases included in (a12) include a rhmA protein. The rhmA protein is preferably derived from *Escherichia coli*.

Examples of aldolases included in (a13) include a galC protein. The galC protein is preferably derived from *Pseudomonas putida*.

The first gene may encode class I aldolases or class II aldolases.

Examples of class I aldolases include an eda protein, a yjhH protein, a yagE protein, a dgoA protein, a nanA protein, a mhpE protein, and a phdJ protein.

Examples of class II aldolases include a hpaI protein, a garL protein, a rhmA protein, a galC protein, and bphI protein.

Preferably, the first gene is selected from the following group consisting of:

(1-1) a gene encoding a protein (that is, a hpaI protein derived from *Escherichia coli*) that consists of an amino acid sequence set forth in SEQ ID NO: 2 and catalyzes an aldol reaction between pyruvic acid and aldehydes;

(1-2) a gene encoding a protein that consists of an amino acid sequence in which one or a plurality of amino acids is deleted, substituted, or added in SEQ ID NO: 2, and has an activity of catalyzing an aldol reaction between pyruvic acid and aldehydes;

(1-3) a gene encoding a protein (that is, a rhmA protein derived from *Escherichia coli*) that consists of an amino acid sequence set forth in SEQ ID NO: 4 and catalyzes an aldol reaction between pyruvic acid and aldehydes;

(1-4) a gene encoding a protein that consists of an amino acid sequence in which one or a plurality of amino acids is deleted, substituted, or added in SEQ ID NO: 4, and has an activity of catalyzing an aldol reaction between pyruvic acid and aldehydes;

(1-5) a gene encoding a protein (that is, a nanA protein derived from *Escherichia coli*) that consists of an amino acid sequence set forth in SEQ ID NO: 6 and catalyzes an aldol reaction between pyruvic acid and aldehydes; and (1-6) a gene encoding a protein that consists of an amino acid sequence in which one or a plurality of amino acids is deleted, substituted, or added in SEQ ID NO: 6, and has an activity of catalyzing an aldol reaction between pyruvic acid and aldehydes.

In the present specification, regarding "one or a plurality of amino acids" in the expression, "one or a plurality of amino acids is deleted, substituted, or added," the number thereof varies depending on positions of amino acid residues in a three-dimensional structure of a protein or types of amino acid residue, but it is preferably 1 to 60, is more preferably 1 to 30, is even more preferably 1 to 15, is still more preferably 1 to 10, and is yet more preferably 1 to 5.

The above-described deletion, substitution, or addition of one or a plurality of amino acids is, for example, a conservative mutation that enables a protein to maintain its normal function. A typical conservative mutation is a conservative substitution. A conservative substitution is a mutation in which a substitution occurs between Phe, Trp, and Tyr when a substitution site is an aromatic amino acid, in which a substitution occurs between Leu, Ile, and Val when a substitution site is a hydrophobic amino acid, in which a substitution occurs between Gln and Asn when a substitution site is a polar amino acid, in which a substitution occurs between Lys, Arg, and His when a substitution site is a basic amino acid, in which a substitution occurs between Asp and Glu when a substitution site is an acidic amino acid, and in which a substitution occurs between Ser and Thr when a substitution site is an amino acid having a hydroxyl group. Specific examples of substitutions regarded as conservative substitutions include a substitution of Ala to Ser or Thr; a substitution of Arg to Gln, His, or Lys; a substitution of Asn to Glu, Gln, Lys, His, or Asp; a substitution of Asp to Asn, Glu, or Gln; a substitution of Cys to Ser or Ala; a substitution of Gln to Asn, Glu, Lys, His, Asp, or Arg; a substitution of Glu to Gly, Asn, Gln, Lys, or Asp; a substitution of Gly to Pro; a substitution of His to Asn, Lys, Gln, Arg, or Tyr; a substitution of Ile to Leu, Met, Val, or Phe; a substitution of Leu to Ile, Met, Val, or Phe; a substitution of Lys to Asn, Glu, Gln, His, or Arg; a substitution of Met to Ile, Leu, Val, or Phe; a substitution of Phe to Trp, Tyr, Met, Ile, or Leu; a substitution of Ser to Thr or Ala; a substitution of Thr to Ser or Ala; a substitution of Trp to Phe or Tyr; a substitution of Tyr to His, Phe, or Trp; and a substitution of Val to Met, Ile, or Leu. In addition, deletions, substitutions, or additions of amino acids include deletions, substitutions, or additions caused by naturally occurring mutations (mutants or variants) which are based on individual differences or species differences in bacteria from which a gene is derived.

A "gene encoding a protein that consists of an amino acid sequence in which one or a plurality of amino acids is deleted, substituted, or added in SEQ ID NO: 2, and has an activity of catalyzing an aldol reaction between pyruvic acid and aldehydes" may be a "gene encoding a protein that consists of an amino acid sequence showing a homology of 80% or more, preferably 90% or more, more preferably 95% or more, even more preferably 97% or more, still more preferably 98% or more, and yet more preferably 99% or more to an amino acid sequence set forth in SEQ ID NO: 2, which is a protein having an activity of catalyzing an aldol reaction between pyruvic acid and aldehydes."

A "gene encoding a protein that consists of an amino acid sequence in which one or a plurality of amino acids is deleted, substituted, or added in SEQ ID NO: 4, and has an activity of catalyzing an aldol reaction between pyruvic acid and aldehydes" may be a "gene encoding a protein that consists of an amino acid sequence showing a homology of 80% or more, preferably 90% or more, more preferably 95% or more, even more preferably 97% or more, still more preferably 98% or more, and yet more preferably 99% or more to an amino acid sequence set forth in SEQ ID NO: 4, which is a protein having an activity of catalyzing an aldol reaction between pyruvic acid and aldehydes."

A "gene encoding a protein that consists of an amino acid sequence in which one or a plurality of amino acids is deleted, substituted, or added in SEQ ID NO: 6, and has an activity of catalyzing an aldol reaction between pyruvic acid and aldehydes" may be a "gene encoding a protein that consists of an amino acid sequence showing a homology of 80% or more, preferably 95% or more, more preferably 97% or more, even more preferably 98% or more, and still more preferably 99% or more to an amino acid sequence set forth in SEQ ID NO: 6, which is a protein having an activity of catalyzing an aldol reaction between pyruvic acid and aldehydes."

A UniProtKB accession number of a hpaI protein derived from *Escherichia coli* is, for example, Q47098; a UniProtKB accession number of a rhmA protein derived from *Escherichia coli* is, for example, P76469; and a UniProtKB accession number of a nanA protein derived from *Escherichia coli* is, for example, P0A6L4.

More preferably, the first gene is a hpaI gene which is derived from *Escherichia coli* and consists of a base sequence set forth in SEQ ID NO: 1, a rhmA gene which is derived from *Escherichia coli* and consists of a base sequence set forth in SEQ ID NO: 3, or a nanA gene which is derived from *Escherichia coli* and consists of a base sequence set forth in SEQ ID NO: 5.

A base sequence set forth in SEQ ID NO: 1 and an amino acid sequence set forth in SEQ ID NO: 2 are as follows.

TABLE 1

(SEQ ID NO: 1) Ec_hpaI gene
atgGAAAACAGTTTTAAAGCGGCGCTGAAAGCAGGCCGTCCGCAGATTGGA
TTATGGCTGGGGCTGAGCAGCAGCTACAGCGCGGAGTTACTGGCCGGAGCA
GGATTCGACTGGTTGTTGATCGACGGTGAGCACGCACCGAACAACGTACAA
ACCGTGCTCACCCAGCTACAGGCGGATTCGCCCTATCCCAGCCAGCCGGTA
GTACGTCCGTCGTGGAACGATCCGGTGCAAATCAAACAACTGCTGGACGTC
GGCACACAAACCTTACTGGTGCCGATGGTACAAAACGCCGACGAAGCCCGT
GAAGCGGTACGCGCCACCCGTTATCCCCCCGCCGGTATTCGCGGTGTGGGC
AGTGCGCTGGCTCGCGCCTCGCGCTGGAATCGCATTCCTGATTACCTGCAA
AAAGCCAACGATCAAATGTGCGTGCTGGTGCAGATCGAAACGCGTGAGGCA
ATGAAGAACTTACCGCAGATTCTGGACGTGGAAGGCGTCGACGGCGTGTTT
ATCGGCCCGGCGGATCTGAGCGCCGATATGGGTTATGCCGGTAATCCGCAG
CACCCGGAAGTACAGGCCGCCATTGAGCAGGCGATCGTGCAGATCCGCGAA
GCGGGCAAAGCGCCGGGGATCCTGATCGCCAATGAGCTACTGGCAAAACGC
TATCTGGAACTGGGCGCGCTGTTTGTCGCCGTCGGCGTTGACACCACCCTG
CTCGCCCGCGCCGCCGAAGCGCTGGCAGCACGGTTTGGCGCGCAGGCTACA
GCGATTAAGCCCGGCGTGTATtaa

TABLE 2

(SEQ ID NO: 2) Ec_hpaI protein
MENSFKAALKAGRPQIGLWLGLSSSYSAELLAGAGFDWLLIDGEHAPNNVQ
TVLTQLQAIAPYPSQPVVRPSWNDPVQIKQLLDVGTQTLLVPMVQNADEAR
EAVRATRYPPAGIRGVGSALARASRWNRIPDYLQKANDQMCVLVQIETREA
MKNLPQILDVEGVDGVFIGPADLSADMGYAGNPQHPEVQAAIEQAIVQIRE
AGKAPGILIANELLAKRYLELGALFVAVGVDTTLLARAAEALAARFGAQAT
AIKPGVY A base sequence set forth in SEQ ID NO: 3 and an amino acid sequence set forth in SEQ ID NO: 4 are as follows.

TABLE 3

(SEQ ID NO: 3) Ec_rhmA gene
atgAACGCATTATTAAGCAATCCCTTTAAAGAACGTTTACGCAAGGGCGAA
GTGCAAATTGGTCTGTGGTTAAGCTCAACGACTGCCTATATGGCAGAAATT
GCCGCCACTTCTGGTTATGACTGGTTGCTGATTGACGGGGAGCACGCGCCA
AACACCATTCAGGATCTTTATCATCAGCTAGAGGCGGTAGCGCCCTATGCC
AGCCAACCCGTGATCCGTCCGGTGGAAGGCAGTAAACCGCTGATTAAACAA
GTCCTGGATATTGGCGCGCAAACTCTACTGATCCCGATGGTCGATACTGCC
GAACAGGCACGTCAGGTGGTGTCTGCCACGCGCTATCCTCCCTACGGTGAG
CGTGGTGTCGGGGCCAGTGTGGCACGGGCTGCGCGCTGGGGACGCATTGGA
AATTACATGGCGCAAGTTAACGATTCGCTTTGTCTGTTGGTGCAGGTGGAA
AGTAAAACGGCACTGGATAACCTGGACGAAATCCTCGACGTCGAAGGGATT
GATGGCGTGTTTATTGGACCTGCCGATCTTTCTGCGTCGTTGGGCTACCCG
GATAACGCCCGGGCACCCGGAAGTGCAGCGAATTATTGAAACCAGTATTCGG
CGGATCCGTGCTGCGGGTAAAGCGGCTGGTTTTCTGGCTGTGGCTCCTGAT
ATGGCGCAGCAATGCCTGGCGTGGGGAGCGAACTTTGTCGCTGTTGGCGTT
GACACGATGCTCTACAGCGATGCCCTGGATCAACGACTGGCGATGTTTAAA
TCAGGCAAAAATGGGCCACGCATAAAAGGTAGTTATtaa

TABLE 4

(SEQ ID NO: 4) Ec_rhmA protein
MNALLSNPFKERLRKGEVQIGLWLSSTTAYMAEIAATSGYDWLLIDGEHAP
NTIQDLYHQLQAVAPYASQPVIRPVEGSKPLIKQVLDIGAQTLLIPMVDTA
EQARQVVSATRYPPYGERGVGASVARAARWGRIENYMAQVNDSLCLLNQVE
SKTALDNLDEILDVEGIDGVFIGPADLSASLGYPDNAGHPEVQRIIETSIR
RIRAAGKAAGFLAVAPDMAQQCLAWGANFVAVGVDTMLYSDALDQRLAMFK
SGKNGPRIKGSY A base sequence set forth in SEQ ID NO: 5 and an amino acid sequence set forth in SEQ ID NO: 6 are as follows.

TABLE 5

(SEQ ID NO: 5) Ec_nanA gene
atgGCAACGAATTTACGTGGCGTAATGGCTGCACTCCTGACTCCTTTTGAC
CAACAACAAGCACTGGATAAAGCGAGTCTGCGTCGCCTGGTTCAGTTCAAT
ATTCAGCAGGGCATCGACGGTTTATACGTGGGTGGTTCGACCGGCGAGGCC
TTTGTACAAAGCCTTTCCGAGCGTGAACAGGTACTGGAAATCGTCGCCGAA
GAGGCGAAAGGTAAGATTAAACTCATCGCCCACGTCGGTTGCGTCAGCACC

TABLE 5-continued

GCCGAAAGCCAACAACTTGCGGCATCGGCTAAACGTTATGGCTTCGATGCC
GTCTCCGCCGTCACGCCGTTCTACTATCCTTTCAGCTTTGAAGAACACTCC
GATCACTATCGGGCAATTATTGATTCGGCGGATGGTTTGCCGATGGTGGTG
TACAACATTCCAGCCCTGAGTGGGGTAAAACTGACCCTGGATCAGATCAAC
ACACTTGTTACATTGCCTGGCGTAGGTGCGCTGAAACAGACCTCTGGCGAT
CTCTATCAGATGGAGCAGATCCGTCGTGAACATCCTGATCTTGTGCTCTAT
AACGGTTACGACGAAATCTTCGCCTCTGGTCTGCTGGCGGGCGCTGATGGT
GGTATCGGCAGTACCTACAACATCATGGGCTGGCGCTATCAGGGGATCGTT
AAGGCGCTGAAAGAAGGCGATATCCAGACCGCGCAGAAACTGCAAACTGAA
TGCAATAAAGTCATTGATTTACTGATCAAAACGGGCGTATTCCGCGGCCTG
AAAACTGTCCTCCATTATATGGATGTCGTTTCTGTGCCGCTGTGCCGCAAA
CCGTTTGGACCGGTAGATGAAAAATATCTGCCAGAACTGAAGGCGCTGGCC
CAGCAGTTGATGCAAGAGCGCGGGtaa

TABLE 6

(SEQ ID NO: 6) Ec_nanA protein
MATNLRGVMAALLTPFDQQQALDKASLRRLVQFNIQQGIDGLYVGGSTGEA
FVQSLSEREQVLEIVAEEAKGKIKLIAHVGCVSTAESQQLAASAKRYGFDA
VSAVTPFYYPFSFEEHCDHYRAIIDSADGLPMVVYNIPALSGVKLTLDQIN
TLVTLPGVGALKQTSGDLYQMEQIRREHPDLVLYNGYDEIFASGLLAGADG
GIGSTYNIMGWRYQGIVKALKEGDIQTAQKLQTECNKVIDLLIKTGVFRGL
KTVLHYMDVVSVPLCRKPFGPVDEKYLPELKALAQQLMQERG Amino acid sequence homologies can be determined using the algorithm BLAST [Pro. Natl. Acad. Sci. USA, 90, 5873 (1993)] and FASTA [Methods Enzymol, 183, 63 (1990)] by Karlin and Altschul. Based on the algorithm BLAST, programs called BLASTN and BLASTX have been developed [J. Mol. Biol., 215, 403 (1990)]. In addition, when an amino acid sequence is analyzed according to BLASTX based on BLAST, parameters are set to score=50 and word length=3, for example. To obtain gapped alignment, Gapped BLAST can be utilized as described in Altschul et al. (1997, Nucleic Acids Res. 25: 3389-3402). Alternatively, PSI-Blast or PHI-Blast can be used to perform an iterated search that detects a positional relationship (Id.) between molecules and a relationship between molecules sharing a common pattern. When using BLAST, Gapped BLAST, PSI-Blast, and PHI-Blast programs, default parameters of the respective programs can be used. These can be referred to at http://www.ncbi.nlm.nih.gov.

The activity of catalyzing an aldol reaction between pyruvic acid and aldehydes can be calculated by, for example, performing this enzyme reaction at 25° C. in 100 mM HEPES-NaOH buffer (pH 8.0) containing 2 mM magnesium chloride, and measuring an initial generation rate of an aldol compound produced from pyruvic acid and aldehydes which are raw materials. A generation rate of the aldol compound can be calculated from, for example, changes of a concentration of the aldol compound itself over time. The concentration of the aldol compound can be measured by, for example, mixing an enzymatic reaction solution and a solution of 130 mM O-benzylhydroxylamine hydrochloride (pyridine:methanol:water=33:15:2) at 1:5 to stop the reaction, detecting O-benzyloxime derivatives produced at that time from the aldol compound using high-performance liquid chromatography, and comparing it with a sample of a known concentration. Here, an activity by which 1 μmol of an aldol compound is formed per minute at 25° C. is defined as 1 unit.

The "gene (hereinafter referred to as a hpaI gene mutant) encoding a protein that consists of an amino acid sequence in which one or a plurality of amino acids is deleted, substituted, or added in SEQ ID NO: 2, and has an activity of catalyzing an aldol reaction between pyruvic acid and aldehydes" can be selected from, for example, DNA libraries of another organism species through PCR or hybridization using primers or probes designed according to pieces of information based on a base sequence of SEQ ID NO: 2. A gene thus selected has a high probability of encoding a protein having an activity of catalyzing an aldol reaction between pyruvic acid and aldehydes.

The "gene (a rhmA gene mutant) encoding a protein that consists of an amino acid sequence in which one or a plurality of amino acids is deleted, substituted, or added in SEQ ID NO: 4, and has an activity of catalyzing an aldol reaction between pyruvic acid and aldehydes" can be selected from, for example, DNA libraries of another organism species through a method similar to the above-mentioned method for selecting the hpaI gene mutant.

The "gene (a nanA gene mutant) encoding a protein that consists of an amino acid sequence in which one or a plurality of amino acids is deleted, substituted, or added in SEQ ID NO: 6, and has an activity of catalyzing an aldol reaction between pyruvic acid and aldehydes" can be selected from, for example, DNA libraries of another organism species through a method similar to the above-mentioned method for selecting the hpaI gene mutant.

(1.3) Second Gene

The second gene encodes an "enzyme that catalyzes a decarboxylation reaction of α-keto acids." The "enzyme that catalyzes a decarboxylation reaction of α-keto acids" refers to an enzyme having an activity of 1 mU/mg protein or more when measured using an enzymatic reaction solution containing purified proteins and α-keto acids (an initial substrate concentration 1 mM) as an enzymatic reaction solution according to a measurement method to be described later. The second gene encodes, for example, an enzyme that catalyzes a decarboxylation reaction of α-keto acids obtained by the aldol reaction catalyzed by the protein encoded by the first gene. An α-keto acid in the "enzyme that catalyzes a decarboxylation reaction of α-keto acids" is, for example, 4-hydroxy-2-oxobutyric acid. The "enzyme that catalyzes a decarboxylation reaction of α-keto acids" is, for example, a decarboxylase.

The second gene may be a gene encoding decarboxylases exemplified below.

(b1) Pyruvate decarboxylase (EC number 4.1.1.1),
(b2) Benzoylformate decarboxylase (EC number 4.1.1.7), and
(b3) Indolepyruvate decarboxylase (EC number 4.1.1.74).

Examples of decarboxylases included in (b1) include a pdc protein. The pdc protein is preferably derived from *Zymomonas mobilis*.

Examples of decarboxylases included in (b2) include an mdlC protein. The mdlC protein is preferably derived from *Pseudomonas putida*.

Examples of decarboxylases included in (b3) include a kivD protein. The kivD protein is preferably derived from *Lactococcus lactis*.

Preferably, the second gene is selected from the following group consisting of:

(2-1) a gene encoding a protein (that is, an mdlC protein derived from *Pseudomonas putida*) that consists of an amino acid sequence set forth in SEQ ID NO: 8 and catalyzes a decarboxylation reaction of α-keto acids; and (2-2) a gene encoding a protein that consists of an amino acid sequence in which one or a plurality of amino acids is deleted, substituted, or added in SEQ ID NO: 8, and has an activity of catalyzing a decarboxylation reaction of α-keto acids.

A "gene encoding a protein that consists of an amino acid sequence in which one or a plurality of amino acids is deleted, substituted, or added in SEQ ID NO: 8, and has an activity of catalyzing a decarboxylation reaction of α-keto acids" may be a "gene encoding a protein that consists of an amino acid sequence showing a homology of 80% or more, preferably 90% or more, more preferably 95% or more, even more preferably 97% or more, still more preferably 98% or more, and yet more preferably 99% or more to an amino acid sequence set forth in SEQ ID NO: 8, which is a protein having an activity of catalyzing a decarboxylation reaction of α-keto acids."

A UniProtKB accession number of an mdIC protein derived from *Pseudomonas putida* is, for example, P20906.

The second gene is more preferably an mdIC gene derived from *Pseudomonas putida* consisting of a base sequence set forth in SEQ ID NO: 7.

A base sequence set forth in SEQ ID NO: 7 and an amino acid sequence set forth in SEQ ID NO: 8 are as follows.

TABLE 7

(SEQ ID NO: 7) Pp_mdlc gene
atgGCTTCGGTACACGGCACCACATACGAACTCTTGCGACGTCAAGGCATC
GATACGGTCTTCGGCAATCCTGGCTCGAACGAGCTCCCGTTTTTGAAGGAC
TTTCCAGAGGACTTTCGATACATCCTGGCTTTCCAGGAAGCGTGTGTGGTG
GGCATTGCAGACGGCTATGCGCAAGCCAGTCGGAAGCCGGCTTTCATTAAC
CTGCATTCTGCTGCTGGTACCGGCAATCCTATGGGTGCACTCAGTAACGCC
TGGAACTCACATTCCCCGCTGATCGTCACTGCCGGCCAGCAGACCAGGGCG
ATGATTGGCGTTGAAGCTCTGCTGACCAACGTCGATGCCGCCAACCTGCCA
CGACCACTTGTCAAATGGAGCTACGAGCCCGCAAGCGCAGCAGAAGTCCCT
CATGCGATGAGCAGGGCTATCCATATGGCAAGCATGGCGCCACAAGGCCCT
GTCTATCTTTCGGTGCCATATGACGATTGGGATAAGGATGCTGATCCTCAG
TCCCACCACCTTTTTGATCGCCATGTCAGTTCATCAGTACGCCTGAACGAC
CAGGATCTCGATATTCTGGTGAAAGCTCTCAACAGCGCATCCAACCCGGCG
ATCGTCCTGGGCCCGGACGTCGACGCAGCAAATGCGAACGCAGACTGCGTC
ATGTTGGCCGAACGCCTCAAAGCTCCGGTTTCGGTTGCGCCATCCGCTCCA
CGCTGCCCATTCCCTACCCGTCATCCTTGCTTCCGTGGATTGATGCCAGCT
GGCATCGCAGCGATTTCTCAGCTGCTCGAAGGTCACGATCTGGTTTTGGTA
ATCGGCGCTCCAGTGTTCCGTTACCACCAATACGACCCAGGTCAATATCTC
AAACCTGGCACGCGATTGATTTCGGTGACCTGCGACCCGCTCGAAGCTGCA
CGCGCGCCAATGGGCGATGCGATCGTGGCAGACATTGGTGCGATGGCTAGC
GCTCTTGCCAACTTGGTTGAAGAGAGCAGCCGCCAGCTCCCAACTGCAGCT
CCGGAACCCGCGAAGGTTGACCAAGACGCTGGCCGACTTCACCCAGAGACA
GTGTTCGACACACTGAACGACATGGCCCCGGAGAATGCGATTTACCTGAAC
GAGTCGACTTCAACGACCGCCCAAATGTGGCAGCGCCTGAACATGCGCAAC
CCTGGTAGCTACTACTTCTGTGCAGCTGGCGGACTGGGCTTCGCCCTGCCT
GCAGCAATTGGCGTTCAACTCGCAGAACCCGAGCGACAAGTCATCGCCGTC
ATTGGCGACGGATCGGCCAACTACAGCATTAGTGCGTTGTGGACTGCAGCT
CAGTACAACATCCCCACTATCTTCGTGATCATGAACAACGGCACCTACGGT
GCGTTGCGATGGTTTGCCGGCGTTCTCGAAGCAGAAAACGTTCCTGGGCTG
GATGTCCCAGGGATCGACTTCCGCGCACTCGCCAAGGGCTATGGTGTCCAA
GCGCTGAAAGCCGACAACCTTGACCAGCTCAAGGGTTCGCTACAAGAAGCG
CTTTCTGCCAAAGGCCCGGTACTTATCGAAGTAAGCACCGTAAGCCCGGTG
AAGtga

TABLE 8

(SEQ ID NO: 8) Pp_mdlC protein
MASVHGTTYELLRRQGIDTVFGNPGSNELPFLKDFPEDFRYILALQEACVV
GIADGYAQASRKPAFINLHSAAGTGNAMGALSNAWNSHSPLIVTAGQQTRA
MIGVEALLTNVDAANLPRPLVKWSYEPASAAEVPHAMSRAIHMASMAPQGP
VYLSVPYDDWDKDADPQSHHLFDRHVSSSVRLNDQDLDILVKALNSASNPA
IVLGPDVDAANANADCVMLAERLKAPVWVAPSAPRCPFPTRHPCFRGLMPA
GIAAISQLLEGHDVVLVIGAPVFRYHQYDPGQYLKPGTRLISVTCDPLEAA
RAPMGDAIVADIGAMASALANLVEESSRQLPTAAPEPAKVDQDAGRLHPET
VFDTLNDMAPENAIYLNESTSTTAQMWQRLNMRNPGSYYFCAAGGLGFALP
AAIGVQLAEPERQVIAVIGDGSANYSISALWTAAQYNIPTIFVIMNNGTYG
ALRWPAGVLEAENVPGLDVPGIDFRALAKGYGVQALKADNLEQLKGSLQEA
LSAKGPVLIEVSTVSPVK The activity of catalyzing a decarboxylation reaction of α-keto acids can be calculated by, for example, performing this enzyme reaction at 30° C. in 100 mM potassium phosphate buffer (pH 6.0) containing 0.5 mM thiamine pyrophosphate, 1 mM magnesium chloride, 10 mM NADH, and an excess amount of alcohol dehydrogenase, and measuring an initial generation rate of an alcohol compound produced by sequential reduction of an aldehyde compound generated from an α-keto acid which is a raw material. A generation rate of the alcohol compound can be calculated from, for example, changes of a concentration of the alcohol compound itself over time. The concentration of the alcohol compound can be measured by, for example, detecting the alcohol compound using high-performance liquid chromatography, and comparing it with a sample of a known concentration. Here, an activity by which 1 µmol of an α-keto acid is decarboxylated per minute at 30° C. is defined as 1 unit.

The "gene (an mdlC gene mutant) encoding a protein that consists of an amino acid sequence in which one or a plurality of amino acids is deleted, substituted, or added in SEQ ID NO: 8, and has an activity of catalyzing a decarboxylation reaction of α-keto acids" can be selected from, for example, DNA libraries of another organism species through a method similar to the above-mentioned method for selecting the hpaI gene mutant.

(1.4) Third Gene

The third gene encodes an "enzyme that catalyzes a reduction reaction of aldehydes." The "enzyme that catalyzes a reduction reaction of aldehydes" refers to an enzyme having an activity of 10 mU/mg protein or more when measured using an enzymatic reaction solution containing purified proteins and aldehydes (an initial substrate concentration 1 mM) as an enzymatic reaction solution according to a measurement method to be described later. Specifically, types of aldehyde in the "enzyme that catalyzes a reduction reaction of aldehydes" differ from types of aldehydes which are substrates of the aldol reaction catalyzed by the enzyme encoded by the first gene. The third gene encodes, for example, an enzyme that catalyzes a reduction reaction of aldehydes obtained by the decarboxylation reaction catalyzed by the protein encoded by the second gene. An aldehyde in the "enzyme that catalyzes a reduction reaction of aldehydes" is, for example, 3-hydroxypropionaldehyde. The "enzyme that catalyzes a reduction reaction of aldehydes" is, for example, an alcohol dehydrogenase.

The third gene may be, for example, a gene encoding 1,3-propanediol dehydrogenase (EC number 1.1.1.202).

Examples of 1,3-propanediol dehydrogenase include a dhaT protein or a lpo protein. The dhaT protein is preferably derived from *Klebsiella pneumoniae*. The lpo protein is preferably derived from *Lactobacillus reuteri*.

Preferably, the third gene is selected from the following group consisting of:

(3-1) a gene encoding a protein (that is, a dhaT protein derived from *Klebsiella pneumoniae*) that consists of an amino acid sequence set forth in SEQ ID NO: 10 and catalyzes a reduction reaction of aldehydes; and (3-2) a gene encoding a protein that consists of an amino acid sequence in which one or a plurality of amino acids is deleted, substituted, or added in SEQ ID NO: 10, and has an activity of catalyzing a reduction reaction of aldehydes.

A "gene encoding a protein that consists of an amino acid sequence in which one or a plurality of amino acids is deleted, substituted, or added in SEQ ID NO: 10, and has an activity of catalyzing a reduction reaction of aldehydes" may be a "gene encoding a protein that consists of an amino acid sequence showing a homology of 80% or more, preferably 90% or more, more preferably 95% or more, even more preferably 97% or more, still more preferably 98% or more, and yet more preferably 99% or more to an amino acid sequence set forth in SEQ ID NO: 10, which is a protein having an activity of catalyzing a reduction reaction of aldehydes."

A UniProtKB accession number of a dhaT protein derived from *Klebsiella pneumoniae* is, for example, Q59477.

The third gene is more preferably a dhaT gene derived from *Klebsiella pneumoniae* consisting of a base sequence set forth in SEQ ID NO: 9.

A base sequence set forth in SEQ ID NO: 9 and an amino acid sequence set forth in SEQ ID NO: 10 are as follows.

TABLE 9

(SEQ ID NO: 9) Kp_dhaT gene
atgAGCTATCGTATGTTCGATTATCTGGTGCCAAACGTTAACTTTTTTGGC
CCCAACGCCATTTCCGTAGTCGGCGAACGCTGCCAGCTGCTGGGGGGGAAA
AAAGCCCTGCTGGTCACCGACAAAGGCCTGCGGGCAATTAAAGATGGCGCG
GTGGACAAAACCCTGCATTATCTGCGGGAGGCCGGGATCGAGGTGGCGATC
TTTGACGGCGTCGAGCCGAACCCGAAAGACACCAACGTGCGCGACGGCCTC
GCTGTGTTTCGCCGCGAACAGTGCGACATCATCGTCACCGTGGGCGGCGGC
AGCCCGCACGATTGCGGCAAAGGCATCGGCATCGCCGCCACCCATGAGGGC
GATCTGTACCAGTATGCCGGAATCGAGACCCTGACCAACCCGCTGCCGCCT
ATCGTCGCGGTCAATACCACCGCCGGCACCGCCAGCGAGGTCACCCGCCAC
TGCGTCCTGACCAACACCGAAACCAAAGTGAAGTTTGTGATCGTCAGCTGG
CGCAACCTGCCGTCGGTCTCTATCAACGATCCACTGCTGATGATCGGTAAA
CCGGCCGCCCTGACCGCGGCGACCGGGATGGATGCCCTGACCCACGCCGTA
GAGGCCTATATCTCCAAAGACGCTAACCCGGTGACGGACGCCGCCGCCATG
CAGGCGATCCGCCTCATCGCCCGCAACCTGCGCCAGGCCGTGGCCCTCGGC
AGCAATCTGCAGGCGCGGGAAAACATGGCCTATGCCTCTCTGCTGGCCGGG
GATGGCTTTCAATAACCCAACCTCGGCTACGTGCACGCCATGGCACACCAG
CTGGGCGGCCTGTACGACATGCCGCACGGCGTGGCCAACGCTGTCCTGCTG
CCGCATGTGGCGCGCTACAACCTGATCGCCAACCCGGAGAAATTCGCCGAT
ATTGCTGAACTGATGGGCGAAAATATCACCGGACTGTCCACTCTCGACGCG
GCGGAAAAAGCCATCGCCGCTATCACGCGTCTGTCGATGGATATCGGTATT
CCGCAGCATCTGCGCGATCTGGGAGTAAAAGAGGCCGACTTCCCCTACATG
GCGGAGATGGCTCTGAAAGACGGCAATGCGTTCTCGAACCCGCGTAAAGGC
AACGAGCAGGAGATTGCCGCGATTTTCCGCCAGGCATTCtaa

TABLE 10

(SEQ ID NO: 10) Kp_dhaT protein
MSYRMFDYLVPNVNFFGPNAISVVGERCQLLGGKKALLVTDKGLRAIKDGA
VDKTLHYLREAGIEVAIFDGVEPNPKDTNVRDGLAVFRREQCDIIVTVGGG
SPHDCGKGIGIAATHEGDLYQYAGIETLTNPLPPIVAVNTTAGTASEVTRH
CVLTNTETKVKFVIVSWRNLPSVSINDPLLMIGKPAALTAATGMDALTHAV
EAYISKDANPVTDAAAMQAIRLIARNLRQAVALGSNLQARENMAYASLLAG
MAFNNANLGYVHAMAHQLGGLYDMPHGVANAVLLPHVARYNLIANPEKFAD
IAELMGENITGLSTLDAAEKATAAITRLSMDIGIPQHLRDLGVKEADFPYM
AEMALKDGNAFSNPRKGNEQEIAAIFRQAF The activity of catalyzing a reduction reaction of aldehydes can be calculated by, for example, performing the enzyme reaction at 30° C. in 50 mM MES-NaOH buffer (pH 6.5) containing 0.2 mM NADH, and measuring an initial consumption rate of NADH consumed when an aldehyde that is a raw material is reduced to an alcohol compound. The initial consumption rate of NADH can be calculated by, for example, measuring a rate of decrease in absorbance at 340 nm which is caused due to NADH in an enzymatic reaction solution. Here, an activity by which 1 µmol of an aldehyde is reduced per minute at 30° C. is defined as 1 unit.

The "gene (a dhaT gene mutant) encoding a protein that consists of an amino acid sequence in which one or a plurality of amino acids is deleted, substituted, or added in SEQ ID NO: 10, and has an activity of catalyzing a reduction reaction of aldehydes" can be selected from, for example, DNA libraries of another organism species through a method similar to the above-mentioned method for selecting the hpaI gene mutant.

(1.5) Construction of Recombinant Vector for Transformation

The first, second, and third genes can be incorporated into an appropriate plasmid vector for transformation.

As a plasmid vector, a known plasmid vector can be used depending on hosts. The plasmid vector may include a gene that controls an autonomous replication function in a host, or may include a base sequence necessary for incorporation of a gene into a host chromosome.

The first, second, and third genes may be respectively incorporated into individual plasmid vectors, or may be incorporated into the same plasmid vector. A transformant can be produced using the obtained recombinant vector.

(1.6) Transformation Form

As a transformation method, a known method can be used without limitation. Examples of such known methods include a calcium chloride/rubidium chloride method, a calcium phosphate method, DEAE-dextran-mediated transfection, an electric pulse method, and the like.

The obtained transformant may be cultured immediately after transformation using a medium generally used for culturing transformants.

A culture temperature may be any temperature as long as it is suitable for growing the transformant. A pH of the medium may be any pH as long as it is suitable for growing the transformant. A pH of the medium can be adjusted by a known method. A pH of the medium can be appropriately adjusted as necessary during culture. A culture time may be any time as long as it is sufficient for growing the transformant.

When the transformant is produced using a recombinant vector as described above, the first, second, and third genes may be respectively incorporated into a host chromosome, or may be present in the cytoplasm of a host in the form of a recombinant vector.

(1.7) Disruption or Deletion of Host Chromosome Gene

A host may be a mutant strain or an artificial genetic recombinant in addition to a wild strain. When the host is a coryneform bacterium, the host is preferably a gene-disrupted strain or a gene-deleted strain obtained by disrupting or deleting at least one of genes originally possessed by coryneform bacteria of a wild strain, the genes being as follows: a lactate dehydrogenase (for example, ldhA) gene, a phosphoenolpyrvate carboxylase (for example, ppc) gene, a pyruvate carboxylase (for example, pyc) gene, a pyruvate dehydrogenase (for example, poxB) gene, a glutamate-pyruvate aminotransferase (for example, alaA) gene, an acetolactate synthase (for example, ilvB) gene, an N-succinyldiaminopimelate aminotransferase (for example, cg0931) gene, an S-(hydroxymethyl)mycothiol dehydrogenase (for example, adhE) gene, and an acetaldehyde dehydrogenase (for example, ald) gene. By using such a gene-disrupted strain or gene-deleted strain as a host, it is possible to improve productivity of 1,3-propanediol or to suppress production of by-products.

Construction of a gene-disrupted strain or a gene-deleted strain can be performed by a known method.

(2.) Culturing Process

A 1,3-propanediol-producing microorganism (for example, the above-described transformant) can be cultured in the presence of a saccharide and formaldehyde to produce 1,3-propanediol. "Culturing in the presence of a saccharide and formaldehyde" refers to culture in a culture solution containing a saccharide and formaldehyde. "Culturing in the presence of a saccharide and formaldehyde" is preferably performed by culturing in a culture solution to which a saccharide and formaldehyde are added.

Prior to culturing in the presence of a saccharide and formaldehyde, the above-described transformant is preferably cultured under aerobic conditions to grow. This culture under aerobic conditions will be hereinafter referred to as growth culture, and culture in the presence of a saccharide and formaldehyde will be hereinafter referred to as production culture. Specifically, for example, culture under aerobic conditions is culture under conditions where a sufficient amount of oxygen for growing the transformant is supplied to a culture solution during a culturing period. Culture under aerobic conditions can be performed by a known method. Culture under aerobic conditions can be realized by supplying oxygen to a culture solution through, for example, aeration, agitation, shaking, or a combination thereof. More specifically, culture under aerobic conditions can be realized by shaking culture or submerged aeration and agitation culture.

When carrying out growth culture prior to production culture, growth culture and subsequent production culture can be performed as follows for example. After the growth culture, first, a container containing a culture solution used in the growth culture (hereinafter referred to as a culture solution for growth) and the transformant suspended in the culture solution for growth is centrifuged to precipitate the transformant. Thereafter, the culture solution for growth is removed from the container, the separated transformant is suspended in a culture solution used for the production culture (hereinafter referred to as a culture solution for production), and thereby the production culture can be performed.

Alternatively, for growth culture and subsequent production culture, after the growth culture, saccharides and formaldehydes are added to the culture solution for growth containing the transformant, aerobic conditions are changed to anaerobic conditions or microaerobic conditions, and thereby the production culture can be performed without exchanging the culture solution. As described above, the growth culture and the production culture can be consecutively performed.

In the present specification, the term "culture" means maintaining the transformant under specifically controlled conditions suitable for growth of the transformant. During a culture period, the transformant may grow or may not grow. Accordingly, the term "culture" can be rephrased as "incubation."

(2.1) Culture Solution for Growth

In the culture solution for growth, it is possible to use a medium generally used for culturing a transformant, such as, for example, a known medium containing a carbon source, a nitrogen source, inorganic salts, and the like.

A culture temperature in the growth culture may be any temperature as long as it is suitable for growing the transformant. A pH of the culture solution for growth may be any pH as long as it is suitable for growing the transformant. A pH of the culture solution for growth can be adjusted by a known method. A culture time in the growth culture may be any time as long as it is sufficient for growing the transformant.

(2.2) Culture Solution for Production

As the culture solution for production, it is possible to use a culture solution containing saccharides, formaldehydes, and other necessary components. As other necessary components, it is possible to use, for example, inorganic salts, carbon sources other than saccharides, or nitrogen sources. A concentration of each component in the culture solution described in the present specification refers to a final concentration in the culture solution at the time of adding each component.

As saccharides, any saccharide can be used as long as it can be incorporated into a living body and can be converted into pyruvic acid by the transformant. Specific examples of saccharides include monosaccharides such as glucose, fructose, mannose, xylose, arabinose, and galactose; disaccharides such as sucrose, maltose, lactose, cellobiose, xylobiose, and trehalose; polysaccharides such as starch; molasses; and the like. Among them, monosaccharides are preferable, and fructose and glucose are more preferable. In addition, saccharides containing glucose as a constituent monosaccharide, specifically disaccharides such as sucrose, oligosaccharides containing glucose as a constituent monosaccharide, and polysaccharides containing glucose as a constituent monosaccharide are preferable. One kind of saccharide may be used, or two or more kinds thereof may be mixed and used. Furthermore, saccharides can be added in the form of a saccharified liquid (including a plurality of saccharides such as glucose and xylose) which is obtained by saccharifying non-edible agricultural waste such as rice straw, bagasse, and corn stover; and energy crops such as switchgrass, napier grass, and miscanthus with saccharifying enzymes.

A concentration of saccharides in the culture solution for production can be as high as possible as long as production of 1,3-propanediol is not inhibited thereby. A concentration of saccharides in the culture solution for production is preferably within a range of 0.1 to 40 (w/v) %, is more preferably within a range of 1 to 20 (w/v) %. In addition, supplementary saccharides can be added according to a decrease of saccharides associated with production of 1,3-propanediol.

A concentration of formaldehydes in the culture solution for production is preferably within a range of 0.001 to 10 (w/v) %, and is more preferably within a range of 0.01 to 1 (w/v) %. In addition, supplementary formaldehydes can be added according to a decrease of formaldehydes associated with production of 1,3-propanediol.

Furthermore, inorganic salts can be added as necessary. As the inorganic salts, it is possible to use metal salts such as phosphates, sulfates, magnesium, potassium, manganese, iron, and zinc. Specifically, it is possible to use monopotassium phosphate, dipotassium phosphate, magnesium sulfate, sodium chloride, ferrous nitrate, iron(II) sulfate, manganese sulfate, zinc sulfate, cobalt sulfate, calcium carbonate, and the like. One kind of inorganic salt may be used, or two or more kinds thereof may be mixed and used. A concentration of inorganic salts in the culture solution for production varies depending on inorganic salts used, but it can be generally set to about 0.01 to 1 (w/v) %.

Furthermore, carbon sources other than saccharides can be added as necessary. As carbon sources other than saccharides, it is possible to use sugar alcohols such as mannitol, sorbitol, xylitol, glycerol, and glycerin; organic acids such as acetic acid, citric acid, lactic acid, fumaric acid, maleic acid, and gluconic acid; hydrocarbons such as normal paraffin; and the like.

Furthermore, nitrogen sources can be added as necessary. As nitrogen sources, it is possible to use inorganic or organic ammonium salts such as ammonium chloride, ammonium sulfate, ammonium nitrate, and ammonium acetate; urea; aqueous ammonia; nitrate salts such as sodium nitrate and potassium nitrate; and the like. Furthermore, it is possible to use corn steep liquor; meat extract; yeast extract; soybean hydrolyzates; protein hydrolyzates such as peptone, NZ-amine, or casein hydrolyzates; nitrogen-containing organic compounds such as amino acids; and the like. One kind of nitrogen source may be used, or two or more kinds thereof may be mixed and used. A concentration of the nitrogen sources in the culture solution for production varies depending on nitrogen compounds used, but it can be generally set to about 0.1 to 10 (w/v) %.

Furthermore, vitamins can be added as necessary. Examples of vitamins include biotin, thiamine (vitamin B1), pyridoxine (vitamin B6), pantothenic acid, inositol, nicotinic acid, and the like.

Specific examples of culture solutions for production include those of glucose, formaldehyde, ammonium sulfate, potassium dihydrogen phosphate, dipotassium hydrogen phosphate, magnesium sulfate, iron(II) sulfate, and manganese(II) sulfate, and a medium having a pH of 6.0 can be used.

Furthermore, as the culture solution for production, it is also possible to use a culture solution obtained by adding saccharides and formaldehyde to a base culture solution having the same composition as the culture solution for growth used in the growth culture. When a sufficient amount of saccharides is present in the above-mentioned base culture solution, saccharides may not be added.

(2.3) Conditions for Production Culture

A culture temperature in the production culture may be any temperature as long as it is suitable for production of 1,3-propanediol. A culture temperature in the production culture is preferably about 20° C. to 50° C., and is more preferably about 25° C. to 47° C. When the temperature is within the above-mentioned range, 1,3-propanediol can be manufactured efficiently. A pH of the culture solution for production may be any pH as long as it is suitable for production of 1,3-propanediol. A pH of the culture solution for production is preferably maintained within a range of about 6 to 8. A pH of the culture solution for production can be adjusted, for example, using an aqueous potassium hydroxide solution. During the production culture, a pH of the culture solution for production can be adjusted as necessary. A culture time in the production culture may be any time as long as it is a sufficient time for the transformant to produce 1,3-propanediol. A culture time in the production culture is preferably about 3 hours to 7 days, and is more preferably about 1 to 3 days.

The production culture may be performed under aerobic conditions, or may be performed under anaerobic conditions or microaerobic conditions. The reason for this is because the above-mentioned transformant has a pathway which is for producing 1,3-propanediol and works under aerobic conditions, anaerobic conditions, or microaerobic conditions. A route for producing 1,3-propanediol will be described in the section "(3.) Actions and effects" below.

<Anaerobic Conditions or Microaerobic Conditions>

The production culture is preferably performed under anaerobic conditions or microaerobic conditions.

When the transformant is cultured under anaerobic conditions or microaerobic conditions, the transformant does not substantially grow and can produce 1,3-propanediol more efficiently.

The "anaerobic conditions or microaerobic conditions" refer to conditions in which a concentration of dissolved oxygen in the culture solution for production is within a range of 0 to 2 ppm, for example. The "anaerobic conditions or microaerobic conditions" preferably refer to conditions in which a concentration of dissolved oxygen in the culture solution for production is within a range of 0 to 1 ppm, and more preferably refers to conditions in which a concentration of dissolved oxygen in the culture solution for production is within a range of 0 to 0.5 ppm. A concentration of dissolved oxygen in the culture solution can be measured using, for example, a dissolved oxygen analyzer.

The term "anaerobic conditions" is a technical term that refers to conditions in which electron acceptors such as dissolved oxygen and oxides such as a nitric acid are not present. On the other hand, it is not necessary to employ the exact conditions described above as preferable conditions for the production culture as long as, due to an insufficient amount of these electron acceptors or due to the nature of the electron acceptors, the transformant does not grow, and thus carbon sources supplied are used for production of 1,3-propanediol, and thereby production efficiency can be increased. That is, in preferable conditions for the production culture, as long as growth of the transformant can be inhibited and production efficiency of 1,3-propanediol can be increased, electron acceptors such as dissolved oxygen and oxides such as a nitric acid may be present in the culture solution for production. Accordingly, the expression "anaerobic conditions or microaerobic conditions" used in the present specification includes such a state.

The anaerobic conditions and microaerobic conditions can be realized by, for example, not ventilating an oxygen-containing gas so that an amount of oxygen supplied from a gas-liquid interface becomes insufficient for growth of the transformant. Alternatively, these conditions can be realized by ventilating an inert gas, specifically a nitrogen gas, into the culture solution for production. Alternatively, these conditions can be realized by sealing a container used for the production culture.

<High Density Conditions>

The production culture is preferably performed in a state in which the transformant is suspended in the culture solution for production at high density. When the transformant is cultured in such a state, 1,3-propanediol can be produced more efficiently.

The "state in which the transformant is suspended in the culture solution for production at a high density" refers to, for example, a state in which the transformant is suspended in the culture solution for production so that a wet bacterial cell weight % of the transformant becomes within a range of 1 to 50 (w/v) %. The "state in which the transformant is suspended in the culture solution for production at a high density" preferably refers to, for example, a state in which the transformant is suspended in the culture solution for production so that a wet bacterial cell weight % of the transformant becomes within a range of 3 to 30 (w/v) %.

The production culture is more preferably performed, under anaerobic conditions or microaerobic conditions, in a state in which the transformant is suspended in the culture solution for production at a high density.

(2.4) Recovery of 1,3-Propanediol

As described above, when the transformant containing the first, second, and third genes is cultured in the culture solution for production, 1,3-propanediol is produced in the culture solution for production. 1,3-Propanediol can be recovered by recovering the culture solution for production, and 1,3-propanediol can also be separated and purified from the culture solution for production by a known method. Examples of such known methods include a distillation method, a concentration method, an ion exchange resin method, an activated carbon adsorption elution method, a solvent extraction method, a crystallization method, and the like.

From the culture solution for production, it is also possible to recover substances such as 4-hydroxy-2-oxobutyric acid produced by the aldol reaction catalyzed by the enzyme encoded by the first gene.

(3.) Actions and Effects

FIG. 1 schematically shows a process in which a 1,3-propanediol-producing microorganism produces 1,3-propanediol. In the process shown in FIG. 1, a case in which a saccharide is glucose will be described as an example.

As shown in FIG. 1, first, glucose 2 and formaldehyde 3 are incorporated into a 1,3-propanediol-producing microorganism 1. Next, the glucose 2 is converted into pyruvic acid 4 through a glycolysis system. Next, the pyruvic acid 4 and the formaldehyde 3 are converted into 4-hydroxy-2-oxobutyric acid 5 by the "enzyme that catalyzes an aldol reaction between pyruvic acid and aldehydes" which is encoded by the first gene. Next, the 4-hydroxy-2-oxobutyric acid 5 is converted into 3-hydroxypropionaldehyde 6 by the "enzyme that catalyzes a decarboxylation reaction of α-keto acids" which is encoded by the second gene. Next, the 3-hydroxypropionaldehyde 6 is converted into 1,3-propanediol 7 by the "enzyme that catalyzes a reduction reaction of aldehydes" which is encoded by the third gene. As described above, 1,3-propanediol is produced.

As described above, in the method described above, the inventors of the present invention have found a production process in which 1,3-propanediol can be obtained by culturing a microorganism having a specific gene in the presence of formaldehyde, and therefore have completed the present invention. Because formaldehyde is generally harmful to microbial growth, the fact that useful compounds were obtained in the presence of formaldehyde was a surprising finding. 1,3-Propanediol is a compound that can be used as a polymer raw material, a cosmetic material, and an antifreeze liquid.

(4.) Preferable Embodiments

Preferable embodiments of the present invention are collectively shown below.

[1] A method for manufacturing 1,3-propanediol, including culturing, in the presence of a saccharide and formaldehyde to produce 1,3-propanediol, a microorganism including the following genes:

(a) a first gene encoding an enzyme that catalyzes an aldol reaction between pyruvic acid and aldehydes;

(b) a second gene encoding an enzyme that catalyzes a decarboxylation reaction of α-keto acids; and (c) a third gene encoding an enzyme that catalyzes a reduction reaction of aldehydes.

[2] The method according to [1], in which the culture is performed by culturing the microorganism in a culture solution containing a saccharide and formaldehyde.

[3] The method according to [2], in which the culture solution is a culture solution to which a saccharide and formaldehyde are added.

[4] The method according to [3], in which the saccharide is added to the culture solution so that a concentration thereof becomes 0.1 to 40 (w/v) %, preferably 1 to 20 (w/v) %.

[5] The method according to [3] or [4], in which the formaldehyde is added in the culture solution so that a concentration thereof becomes 0.001 to 10 (w/v) %, preferably 0.01 to 1 (w/v) %.

[6] The method according to any one of [1] to [5], in which the saccharide is a saccharified liquid obtained by treating, with saccharifying enzymes, monosaccharides such as fructose or glucose; disaccharides such as sucrose; polysaccharides such as a polysaccharide containing glucose as a constituent monosaccharide; or plants (non-edible agricultural waste or energy crops).

[7] The method according to [1] to [6], in which the saccharide is glucose.

[8] The method according to any one of [1] to [7], in which the culture is performed under anaerobic conditions or microaerobic conditions.

[9] The method according to [8], in which the culture is performed by culturing the microorganism in a culture solution containing a saccharide and formaldehyde.

[10] The method according to [9], in which the anaerobic conditions or the microaerobic conditions are conditions in which a concentration of dissolved oxygen in the culture solution is within a range of 0 to 2 ppm, preferably within a range of 0 to 1 ppm, and more preferably within the range of 0 to 0.5 ppm.

[11] The method according to any one of [1] to [10], in which the culture is performed in a state where the microorganism is suspended in the culture solution at a high density.

[12] The method according to [11], in which the culture is performed by culturing the microorganism in a culture solution containing a saccharide and formaldehyde.

[13] The method according to [12], in which the state in which the microorganism is suspended in the culture solution at a high density is a state in which the microorganism is suspended in the culture solution so that a wet bacterial cell weight % of the microorganism is within a range of 1 to 50 (w/v) %, and is preferably a state in which the microorganism is suspended in the culture solution so that a wet bacterial cell weight % of the microorganism is within a range of 3 to 30 (w/v) %.

[14] The method according to any one of [1] to [13], in which the first gene encodes an aldolase.

[15] The method according to any one of [1] to [14], in which the first gene encodes a type I aldolase.

[16] The method according to any one of [1] to [14], in which the first gene encodes a type II aldolase.

[17] The method according to any one of [1] to [16], in which the first gene encodes an aldolase selected from the group consisting of:
  (a1) 2-dehydro-3-deoxy-phosphogluconatealdolase;
  (a2) 2-dehydro-3-deoxy-6-phosphogluconatealdolase;
  (a3) 4-hydroxy-2-oxoglutarate aldolase;
  (a4) (4 S)-4-hydroxyl-2-oxoglutarate aldolase;
  (a5) 2-dehydro-3-deoxy-D-pentonate aldolase;
  (a6) 2-dehydro-3-deoxy-D-gluconate aldolase;
  (a7) 3-deoxy-D-manno-octulosonate aldolase;
  (a8) 4-hydroxyl-2-oxovalerate aldolase;
  (a9) 4-(2-carboxyphenyl)-2-oxobut-3-enoate aldolase;
  (a10) 4-hydroxy-2-oxoheptanedioate aldolase;
  (a11) 2-dehydro-3-deoxyglucarate aldolase;
  (a12) 2-keto-3-deoxy-L-rhamnonate aldolase;
  (a13) 4-hydroxyl-4-methyl-2-oxoglutarate aldolase; and
  (a14) 4-hydroxy-2-oxohexanoate aldolase.

[18] The method according to any one of [1] to [17], in which the first gene encodes an aldolase selected from the group consisting of an eda protein, preferably an eda protein derived from *Escherichia coli*; a dgoA protein, preferably a dgoA protein derived from *Escherichia coli*; a yjhH protein, preferably a yjhH protein derived from *Escherichia coli*; a yagE protein, preferably a yagE protein derived from *Escherichia coli*; a nanA protein, preferably a nanA protein derived from *Escherichia coli*; an mhpE protein, preferably a mhpE protein derived from *Escherichia coli*; a hpaI protein, preferably a hpaI protein derived from *Escherichia coli*; a bphI protein, preferably a bphI protein derived from *Burkholderia xenovorans*; a phdJ protein, preferably a phdJ protein derived from the genus *Nocardioides*; a garL protein, preferably a galL protein derived from *Escherichia coli*; an rhmA protein, preferably an rhmA protein derived from *Escherichia coli*; and a galC protein, preferably, a galC protein derived from *Pseudomonas putida*.

[19] The method according to any one of [1] to [18], in which the first gene encodes an aldolase selected from the group consisting of a nanA protein, preferably a nanA protein derived from *Escherichia coli*; an hpaI protein, preferably an hpaI protein derived from *Escherichia coli*; and a rhmA protein, preferably an rhmA protein derived from *Escherichia coli*.

[20] The method according to any one of [1] to [19], in which the first gene is selected from the group consisting of:
  (1-1) a gene encoding a protein that consists of an amino acid sequence set forth in SEQ ID NO: 2 and catalyzes an aldol reaction between pyruvic acid and aldehydes;
  (1-2) a gene encoding a protein that consists of an amino acid sequence in which one or a plurality of amino acids is deleted, substituted, or added in SEQ ID NO: 2, and has an activity of catalyzing an aldol reaction between pyruvic acid and aldehydes;
  (1-3) a gene encoding a protein that consists of an amino acid sequence set forth in SEQ ID NO: 4 and catalyzes an aldol reaction between pyruvic acid and aldehydes;
  (1-4) a gene encoding a protein that consists of an amino acid sequence in which one or a plurality of amino acids is deleted, substituted, or added in SEQ ID NO: 4, and has an activity of catalyzing an aldol reaction between pyruvic acid and aldehydes;
  (1-5) a gene encoding a protein that consists of an amino acid sequence set forth in SEQ ID NO: 6 and catalyzes an aldol reaction between pyruvic acid and aldehydes; and
  (1-6) a gene encoding a protein that consists of an amino acid sequence in which one or a plurality of amino acids is deleted, substituted, or added in SEQ ID NO: 6, and has an activity of catalyzing an aldol reaction between pyruvic acid and aldehydes.

[21] The method according to any one of [1] to [20], in which the first gene is selected from the group consisting of:
  a hpaI gene which is derived from *Escherichia coli* and consists of a base sequence set forth in SEQ ID NO: 1;
  a rhmA gene which is derived from *Escherichia coli* and consists of a base sequence set forth in SEQ ID NO: 3; and
  a nanA gene which is derived from *Escherichia coli* and consists of a base sequence set forth in SEQ ID NO: 5.

[22] The method according to any one of [1] to [21], in which the second gene encodes the enzyme that catalyzes the decarboxylation reaction of α-keto acids obtained by the aldol reaction.

[23] The method according to any one of [1] to [22], in which the second gene encodes a decarboxylase.

[24] The method according to any one of [1] to [23], in which the second gene encodes a decarboxylase selected from the group consisting of:
  (b1) pyruvate decarboxylase;
  (b2) benzoylformate decarboxylase; and
  (b3) indolepyruvate decarboxylase.

[25] The method according to any one of [1] to [24], in which the second gene encodes a decarboxylase selected from the group consisting of a pdc protein, preferably a pdc protein derived from *Zymomonas mobilis*; a mdlC protein, preferably a mdlC protein derived from *Pseudomonas putida*; and a kivD protein, preferably a kivD protein derived from *Lactococcus lactis*.

[26] The method according to any one of [1] to [25], in which the second gene encodes an mdlC protein, preferably an mdlC protein derived from *Pseudomonas putida*.
[27] The method according to any one of [1] to [26], in which the second gene is selected from the group consisting of:
(2-1) a gene encoding a protein that consists of an amino acid sequence set forth in SEQ ID NO: 8 and catalyzes a decarboxylation reaction of α-keto acids; and
(2-2) a gene encoding a protein that consists of an amino acid sequence in which one or a plurality of amino acids is deleted, substituted, or added in SEQ ID NO: 8, and has an activity of catalyzing a decarboxylation reaction of α-keto acids.
[28] The method according to any one of [1] to [27], in which the second gene is an mdlC gene derived from *Pseudomonas putida* consisting of a base sequence set forth in SEQ ID NO: 7.
[29] The method according to any one of [1] to [28], in which the third gene encodes the enzyme that catalyzes a reduction reaction of an aldehyde that is a type different from the aldehyde that is a substrate of the aldol reaction catalyzed by the enzyme encoded by the first gene.
[30] The method according to any one of [1] to [29], in which the third gene encodes the enzyme that catalyzes the reduction reaction of the aldehyde obtained by the decarboxylation reaction.
[31] The method according to any one of [1] to [30], in which the third gene encodes an alcohol dehydrogenase.
[32] The method according to any one of [1] to [31], in which the third gene encodes a 1,3-propanediol dehydrogenase.
[33] The method according to any one of [1] to [32], in which the third gene encodes 1,3-propanediol dehydrogenase selected from the group consisting of a dhaT protein, preferably a dhaT protein derived from *Klebsiella pneumoniae*; and an lpo protein, preferably an lpo protein derived from *Lactobacillus reuteri*.
[34] The method according to any one of [1] to [33], in which the third gene is selected from the group consisting of:
(3-1) a gene encoding a protein that consists of an amino acid sequence set forth in SEQ ID NO: 10 and catalyzes a reduction reaction of aldehydes; and
(3-2) a gene encoding a protein that consists of an amino acid sequence in which one or a plurality of amino acids is deleted, substituted, or added in SEQ ID NO: 10, and has an activity of catalyzing a reduction reaction of aldehydes.
[35] The method according to any one of [1] to [34], in which the third gene is a dhaT gene derived from *Klebsiella pneumoniae* consisting of a base sequence set forth in SEQ ID NO: 9.
[36] The method according to any one of [1] to [35], in which the first gene is selected from the group consisting of:
(1-1) a gene encoding a protein that consists of an amino acid sequence set forth in SEQ ID NO: 2 and catalyzes an aldol reaction between pyruvic acid and aldehydes;
(1-2) a gene encoding a protein that consists of an amino acid sequence in which one or a plurality of amino acids is deleted, substituted, or added in SEQ ID NO: 2, and has an activity of catalyzing an aldol reaction between pyruvic acid and aldehydes;
(1-3) a gene encoding a protein that consists of an amino acid sequence set forth in SEQ ID NO: 4 and catalyzes an aldol reaction between pyruvic acid and aldehydes;
(1-4) a gene encoding a protein that consists of an amino acid sequence in which one or a plurality of amino acids is deleted, substituted, or added in SEQ ID NO: 4, and has an activity of catalyzing an aldol reaction between pyruvic acid and aldehydes;
(1-5) a gene encoding a protein that consists of an amino acid sequence set forth in SEQ ID NO: 6 and catalyzes an aldol reaction between pyruvic acid and aldehydes; and
(1-6) a gene encoding a protein that consists of an amino acid sequence in which one or a plurality of amino acids is deleted, substituted, or added in SEQ ID NO: 6, and has an activity of catalyzing an aldol reaction between pyruvic acid and aldehydes,
in which the second gene is selected from the group consisting of:
(2-1) a gene encoding a protein that consists of an amino acid sequence set forth in SEQ ID NO: 8 and catalyzes a decarboxylation reaction of α-keto acids; and
(2-2) a gene encoding a protein that consists of an amino acid sequence in which one or a plurality of amino acids is deleted, substituted, or added in SEQ ID NO: 8, and has an activity of catalyzing a decarboxylation reaction of α-keto acids, and
in which the third gene is selected from the group consisting of:
(3-1) a gene encoding a protein that consists of an amino acid sequence set forth in SEQ ID NO: 10 and catalyzes a reduction reaction of aldehydes; and
(3-2) a gene encoding a protein that consists of an amino acid sequence in which one or a plurality of amino acids is deleted, substituted, or added in SEQ ID NO: 10, and has an activity of catalyzing a reduction reaction of aldehydes.
[37] The method according to any one of [1] to [36] in which the microorganism is an aerobic bacterium, is preferably a coryneform bacterium, is more preferably bacteria belonging to the genus *Corynebacterium*, and is even more preferably *Corynebacterium glutamicum*.
[38] The method according to any one of [1] to [37], in which the microorganism is a microorganism transformed with the first gene, the second gene, and the third gene.
[39] The method according to any one of [1] to [38], in which the microorganism is a gene-deleted strain from which at least one gene is deleted, the gene being selected from the group consisting of a lactate dehydrogenase gene, a phosphoenolpyrvate carboxylase gene, a pyruvate carboxylase gene, a pyruvate dehydrogenase gene, a glutamate-pyruvate aminotransferase gene, an acetolactate synthase gene, an N-succinyldiaminopimelate aminotransferase gene, an S-(hydroxymethyl)mycothiol dehydrogenase gene, and an acetaldehyde dehydrogenase gene.
[40] The method according to any one of [1] to [39], further including culturing the microorganism under aerobic conditions before the culturing.
[41] The method according to any one of [1] to [40], further including recovering the produced 1,3-propanediol.

EXAMPLES

1. Materials and Methods (1-1) Medium

Reagents were purchased from FUJIFILM Wako Pure Chemical Corporation unless otherwise indicated.
(A Medium)
Urea 2.0 g, ammonium sulfate 7.0 g, potassium dihydrogen phosphate 0.50 g, dipotassium hydrogen phosphate 0.50 g, magnesium sulfate heptahydrate 0.50 g, Yeast Extract (manufactured by Difco) 2.0 g, Casamino Acids Vitamin Assay (manufactured by Difco) 7.0 g, iron(II) sulfate heptahydrate 6.0 mg, manganese(II) sulfate-hydrate 4.2 mg, D(+)-biotin 0.20 mg, and thiamine hydrochloride 0.20 mg were dissolved in 0.92 L of water, and a pH was adjusted to 7.0 using a 5 M aqueous potassium hydroxide solution. The mixture was autoclave-sterilized at 121° C. for 20 minutes and cooled to room temperature. Thereafter, 80 mL of a 50% (w/v) autoclave-sterilized aqueous glucose solution was added thereto, and thereby a liquid medium was prepared.

(A Agar Medium)

Urea 2.0 g, ammonium sulfate 7.0 g, potassium dihydrogen phosphate 0.50 g, dipotassium hydrogen phosphate 0.50 g, magnesium sulfate heptahydrate 0.50 g, Yeast Extract (manufactured by Difco) 2.0 g, Casamino Acids Vitamin Assay (manufactured by Difco) 7.0 g, iron(II) sulfate heptahydrate 6.0 mg, manganese(II) sulfate-hydrate 4.2 mg, D(+)-biotin 0.20 mg, and thiamine hydrochloride 0.20 mg were dissolved and suspend in 0.92 L of water, and a pH was adjusted to 7.0 using a 5 M aqueous potassium hydroxide solution. The mixture was autoclave-sterilized at 121° C. for 20 minutes and cooled to 50° C. Thereafter, 80 mL of a 50% (w/v) autoclave-sterilized aqueous glucose solution was added thereto. The mixture was dispensed to a Petri dish, and then cooled and solidified, and thereby a solid medium was prepared.

(BA Medium)

Urea 2.0 g, ammonium sulfate 7.0 g, potassium dihydrogen phosphate 0.50 g, dipotassium hydrogen phosphate 0.50 g, magnesium sulfate heptahydrate 0.50 g, Yeast Extract (manufactured by Difco) 2.0 g, Casamino Acids Vitamin Assay (manufactured by Difco) 7.0 g, iron(II) sulfate heptahydrate 6.0 mg, manganese(II) sulfate-hydrate 4.2 mg, D(+)-biotin 0.20 mg, thiamine hydrochloride 0.20 mg, and 4-morpholinopropanesulfonic acid 21 g were dissolved in 0.92 L of water, and a pH was adjusted to 7.0 using a 5 M aqueous potassium hydroxide solution. The mixture was autoclave-sterilized at 121° C. for 20 minutes and cooled to room temperature. Thereafter, 80 mL of a 50% (w/v) autoclave-sterilized aqueous glucose solution was added thereto, and thereby a liquid medium was prepared.

(Lb Medium)

Bacto Tryptone (manufactured by Difco) 10 g, Yeast Extract (manufactured by Difco) 5.0 g, and sodium chloride 10 g were dissolved in 1 L of water, and a pH was adjusted to 7.0 using a 5 M aqueous sodium hydroxide solution. Thereafter, autoclave sterilization was performed at 121° C. for 20 minutes, and thereby a liquid medium was prepared.

(LB Agar Medium)

Bacto Tryptone (manufactured by Difco) 10 g, Yeast Extract (manufactured by Difco) 5.0 g, sodium chloride 10 g, and agar 15 g were dissolved and suspended in 1 L of water, and a pH was adjusted to 7.0 using a 5 M aqueous sodium hydroxide solution. Thereafter, the mixture was autoclave-sterilized at 121° C. for 20 minutes and cooled to 50° C. Thereafter, the mixture was dispensed to a Petri dish, and then cooled and solidified, and thereby a solid medium was prepared.

(Suc Agar Medium)

Bacto Tryptone (manufactured by Difco) 10 g, Yeast Extract (manufactured by Difco) 5.0 g, sodium chloride 10 g, and Agar 15 g were dissolved and suspended in 0.5 L of water, and a pH was adjusted to 7.0 using a 5 M aqueous sodium hydroxide solution. The mixture was autoclave-sterilized at 121° C. for 20 minutes and cooled to 50° C. Thereafter, 0.5 L of a 20% (w/v) autoclave-sterilized aqueous sucrose solution was added thereto. The mixture was dispensed to a Petri dish, and then cooled and solidified, and thereby a solid medium was prepared.

(BHIS Medium)

Brain Heart Infusion (manufactured by Difco) 36 g and sorbitol 91 g were dissolved in 1 L of water, and a pH was adjusted to 7.0 using a 5 M aqueous sodium hydroxide solution. Thereafter, autoclave sterilization was performed at 121° C. for 20 minutes, and thereby a liquid medium was prepared.

(BHIS-GIT Medium)

Brain Heart Infusion (manufactured by Difco) 36 g, glycine 8.0 g, isoniazid 1.3 g, Tween 80 3 mL, and sorbitol 91 g were dissolved in 1 L of water, and a pH was adjusted to 7.0 using a 5 M aqueous sodium hydroxide solution. Thereafter, autoclave sterilization was performed at 121° C. for 20 minutes, and thereby a liquid medium was prepared.

(1-2) Buffers and Reagents (TE Buffer)

Trishydroxymethylaminomethane 1.2 g and ethylenediamine-N,N,N',N'-tetraacetic acid disodium salt dihydrate 0.37 g were dissolved in 1 L of water, and a pH was adjusted to 8.0 using 6M hydrochloric acid. Thereafter, autoclave sterilization was performed at 121° C. for 20 minutes, and thereby a buffer solution was obtained.

(TG Buffer)

Trishydroxymethylaminomethane 0.12 g and glycerol 10 g were dissolved in 1 L of water, and a pH was adjusted to 7.5 using 6M hydrochloric acid. Thereafter, autoclave sterilization was performed at 121° C. for 20 minutes, and thereby a buffer solution was prepared.

(10% Glycerol Aqueous Solution)

100 g of glycerol was dissolved in 1 L of water, and then autoclave-sterilized at 121° C. for 20 minutes. Thereby, an aqueous solution was prepared.

(BR Buffer)

Potassium dihydrogen phosphate 0.50 g, dipotassium hydrogen phosphate 0.50 g, magnesium sulfate heptahydrate 0.50 g, iron(II) sulfate heptahydrate 6.0 mg, and manganese(II) sulfate-hydrate 4.2 mg were dissolved in 1.0 L of water, and a pH was adjusted to 7.0 using a 5 M aqueous potassium hydroxide solution. Thereby, a buffer solution was obtained.

(1-3) Definition of Analysis Conditions and Experimental Method (Extraction and Purification of DNA Fragments after Agarose Gel Electrophoresis) DNA fragments were extracted and purified using NucleoSpin (registered trademark) Gel and PCR Clean-up (manufactured by MACHEREY-NAGEL GmbH & Co. KG) according to the attached instructions.

(Plasmid Extraction)

Plasmid extraction and purification were performed using NucleoSpin (registered trademark) Plasmid EasyPure (manufactured by MACHEREY-NAGEL GmbH & Co. KG) according to the attached instructions.

(PCR Method)

PCR was performed according to the attached instructions using any of the following DNA polymerases and reagents attached thereto: PrimeSTAR (registered trademark) HS DNA Polymerase (manufactured by Takara Bio Inc.), PrimeSTAR (registered trademark) Max DNA Polymerase (manufactured by Takara Bio Inc.), and Tks Gflex™ DNA Polymerase (manufactured by Takara Bio Inc.).

(Liquid Chromatography for Organic Acid Analysis)

An organic acid analysis system which is manufactured by Shimadzu Corporation and is configured of the following devices was used. The devices are: a System controller: CBM-20A, a liquid feeding unit: LC-20AB, an online degassing unit: DGU-20A3R, an autoinjector: SIL-20AC, a column oven: CTO-20AC, and a photodiode array detector: SPD-M20A.

Analysis conditions are as follows.

Guard column: TSKgel OApak-P (manufactured by Tosoh Corporation)

Analysis column: TSKgel OApak-P (manufactured by Tosoh Corporation)

Column oven temperature: 40° C.

Mobile phase: 0.75 mM sulfuric acid

Flow rate: 1.0 mL/min (Liquid Chromatography for Sugar Analysis)

A sugar analysis system which is manufactured by Shimadzu Corporation and configured of the following devices was used. The devices are: a System controller: CBM-20A, a liquid feeding unit: LC-20AB, an online degassing unit: DGU-20A3R, an autoinjector: SIL-20AC, a column oven: CTO-20AC, a refractive index detector: RID-10A.

Analysis conditions are as follows.

Pretreatment: Desalting Cartridge (manufactured by Bio-Rad Laboratories)

Analysis column: Aminex HPX-87P (manufactured by Bio-Rad Laboratories)

Column oven temperature: 85° C.

Mobile phase: water

Flow rate: 0.6 mL/min.

(Genomic DNA Extraction)

The microorganisms were liquid-cultured according to the attached instructions of the source were recovered by centrifugation and frozen at −80° C. Bacterial cell pellets were thawed at room temperature, 537 µL of a 10 mg/ml lysozyme aqueous solution was added thereto, and the mixture was shaken at 37° C. for 1 hour. Next, 30 µL of a 0.5 M EDTA aqueous solution, 30 µL of a 10% SDS aqueous solution, and 3 µL of a 20 mg/ml proteinase K aqueous solution were added, and the mixture was shaken at 37° C. for 1 hour. Thereafter, 100 µL of a 5M sodium chloride aqueous solution and 80 µL of a 10% hexadecyltrimethylammonium bromide aqueous solution (in 0.7M sodium chloride) were added, and the mixture was heated at 65° C. for 10 minutes. After cooling to room temperature, 780 µL of chloroform-isoamyl alcohol (24:1) was added and gently mixed. Centrifugation was performed at 15000×g and 4° C. for 5 minutes to recover 600 µL of an aqueous layer. 600 µL of phenol-chloroform-isoamyl alcohol (25:24:1) was added thereto and gently mixed. Centrifugation was performed at 15000×g and 4° C. for 5 minutes to recover 500 µL of an aqueous layer. 300 µL of isopropanol was added thereto and centrifuged at 15000×g and 4° C. for 5 minutes, and then the supernatant was removed. Genomic DNA obtained as a precipitate was washed with 500 µL of 70% ethanol and centrifuged at 15000×g and 4° C. for 5 minutes. This washing was repeated twice, drying was performed at room temperature, and then the obtained genomic DNA was dissolved in 100 µL of TE buffer.

(Electroporation for Transforming Strain Derived from *Corynebacterium glutamicum* ATCC13032)

A glycerol stock of a strain derived from *Corynebacterium glutamicum* ATCC13032 to be transformed was inoculated into the A agar medium under aseptic conditions and cultured at 33° C. Bacterial cells grown on the agar medium were inoculated into 10 mL of the A medium and shaking-cultured at 33° C., and thereby a seed culture solution was obtained. This seed culture solution was inoculated into 100 mL of the BHIS medium prepared in a 500 mL flask so that a turbidity was 0.2. The mixture was shaken at 33° C. and cultured until a turbidity reached 0.5 to 0.7. This culture solution was centrifuged at 4° C. and 5500×g for 20 minutes, and the supernatant was removed. The recovered bacterial cells were washed with 10 mL of TG buffer, centrifuged at 4° C. and 5500×g for 5 minutes, and the supernatant was removed. This washing was performed twice. Thereafter, the cells were washed with 10 mL of a 10% glycerol aqueous solution and centrifuged at 4° C. and 5500×g for 5 minutes, and the supernatant was removed. The obtained bacterial cell pellets were suspended in 1 mL of a 10% glycerol aqueous solution, dispensed to a sterilized 1.5 mL tube by 150 µL, frozen using liquid nitrogen, and stored at −80° C. as competent cells.

In a case of gene deletion and gene replacement on genomic DNA, 150 µL of competent cells were thawed on ice, and 500 ng of plasmid was added thereto. These cells were transferred to a 0.2 cm-gap sterile electroporation cuvette (manufactured by Bio-Rad), and electroporation was performed at 25 g, 2000, 2500 V using a Gene Pulser Xcell™ electroporation system (manufactured by Bio-Rad). The bacterial cell suspension was diluted with 1 mL of the BHIS medium, incubated at 46° C. for 6 minutes, and then incubated at 33° C. for 1 hour. This bacterial cell suspension was inoculated into an A agar medium containing an appropriate antibiotic substance, and a desired transformant was selected.

In a case where a gene overexpression plasmid was introduced, 50 µL of competent cells was thawed on ice, and 200 ng of plasmid was added thereto. These cells were transferred to a 0.2 cm-gap sterile electroporation cuvette (manufactured by Bio-Rad), and electroporation was performed at 25 g, 2000, 2500 V using a Gene Pulser Xcell™ electroporation system (manufactured by Bio-Rad). The bacterial cell suspension was diluted with 1 mL of the BHIS medium, incubated at 46° C. for 6 minutes, and then incubated at 33° C. for 1 hour. This bacterial cell suspension was inoculated into an A agar medium containing an appropriate antibiotic substance, and a desired transformant was selected.

(Colony PCR)

Reagents other than a template DNA were mixed according to the attached instructions of TaKaRa Ex Taq (registered trademark) (manufactured by Takara Bio Inc.) using a combination of primers capable of amplifying a target DNA sequence. A small amount of a colony of a bacterial strain produced in the agar medium was suspended in this mixture, and using DNA present therein as a template, PCR was performed according to the attached instructions. PCR products were analyzed by agarose gel electrophoresis, and it was confirmed that a target plasmid was retained, or that the corresponding DNA sequence on the genome was deleted or substituted.

(Turbidity Measurement)

A turbidity of the culture solution of *Escherichia coli* and *Corynebacterium glutamicum* was measured at a wavelength of 610 nm using Ultrospec 8000 (manufactured by GE Healthcare).

(1-4) Details of Primer DNAs, Bacterial Cells, and Plasmids

Details of primer DNAs, bacterial cells, and plasmids are shown in Tables 11 to 31 below.

TABLE 11

| Plasmid ID | Target gene | Target vector | | Template | DNA ID | DNA sequences |
|---|---|---|---|---|---|---|
| PGE015 | sacB | pHSG299 | F | pNIC28-Bsa4 | GEP007 | GGGGAAGCTTGACGTCCACATATACCTGCC (SEQ ID NO: 11) |
| | | | R | | GEP008 | ATTCGGATCCGTATCCACCTTTAC (SEQ ID NO: 12) |

TABLE 12

| DNA ID | DNA sequences |
|---|---|
| GEP808 | TGAACAGATACCATTTGCCGTTCATT (SEQ ID NO: 13) |
| GEP809 | AATGGTATCTGTTCACTGACTCCCGC (SEQ ID NO: 14) |

TABLE 13

| Plasmid ID | Deletion target | Target vector | | Template | DNA ID | DNA sequences |
|---|---|---|---|---|---|---|
| pGE020 | ppc | PGE015 (EcoRI) | Up-F | ATCC13032 genome | GEP132 | CCATGATTACGAATTCGGGAAACTTTTTTAAGAAA (SEQ ID NO: 15) |
| | | | Up-R | ATCC13032 genome | GEP133 | TAACTACTTTAAACACTCTT (SEQ ID NO: 16) |
| | | | Down-F | ATCC13032 genome | GEP134 | TGTTTAAAGTAGTTATCCAGCCGGCTGGGTAGTAC (SEQ ID NO: 17) |
| | | | Down-R | ATCC13032 genome | GEP135 | TACCGAGCTCGAATTGAAGTATTCAAGGGGATTTC (SEQ ID NO: 18) |
| pGE033 | IdhA | pGE015 (EcoRI) | Up-F | ATCC13032 genome | GEP169 | GACGGCCACTGAATTTTTCATACGACCACGGGCTA (SEQ ID NO: 19) |
| | | | Up-R | ATCC13032 genome | GEP170 | GACAATCTTGTTACCGACGG (SEQ 10 NO: 20) |
| | | | Down-F | ATCC13032 genome | GEP215 | GGTAACAAGATTGTCCATTCCGCAAATACCCTGCG (SEQ ID NO: 21) |
| | | | Down-R | ATCC13032 genome | GEP216 | TACCGAGCTCGAATTGGGACGTTGATGACGCTGCC (SEQ ID NO: 22) |

TABLE 14

| Plasmid ID | Deletion target | Target vector | | Template | DNA ID | DNA sequences |
|---|---|---|---|---|---|---|
| PGE177 | pyc | pGE015 (EcoRI) | Up-F | ATCC13032 genome | GEP615 | GACGGCCAGTGAATTGTTGATGACTGTTGGTTCCA (SEQ ID NO: 23) |
| | | | Up-R | ATCC13032 genome | GEP616 | CTCGAGTAGAGTAATTATTCCTTTCA (SEQ ID NO: 24) |
| | | | Down-F | ATCC13032 genome | GEP617 | ATTACTCTACTCGAGACCTTTCTGTAAAAGCCCC (SEQ ID NO: 25) |
| | | | Down-R | ATCC13032 genome | GEP618 | TACCGAGCTCGAATTCACGATCCGCCGGGCAGCCT (SEQ ID NO: 26) |
| pGE191 | poxB | pGE015 (EcoRI) | Up-F | ATCC13032 genome | GEP406 | GACGGCCAGTGAAAACGTTAATGAGGAAAACCG (SEQ ID NO: 27) |
| | | | Up-R | ATCC13032 genome | GEP407 | AATTAATTGTTCTGCGTAGC (SEQ ID NO: 28) |
| | | | Down-F | ATCC13032 genome | GEP698 | GCAGAACAATTAATTCTCGAGTCGAACATAAGGAATATTCC (SEQ ID NO: 29) |
| | | | Down-R | ATCC13032 genome | GEP409 | TACCGAGCTCGAATTTCCAGGTACGGAAAGTGCC (SEQ ID NO: 30) |

TABLE 15

| Plasmid ID | Deletion target | Target vector | | Template | DNA ID | DNA sequences |
|---|---|---|---|---|---|---|
| pGE210 | alaA | pGE015 (EcoRI) | Up-F | ATCC13032 genome | GEP810 | GACGGCCAGTGAATTTTTCACCGAAGTGACACCTA (SEQ ID NO: 31) |
| | | | Up-R | ATCC13032 genome | GEP811 | CTCGAGCCGCTCAATGTTGCCACTTT (SEQ ID NO: 32) |
| | | | Down-F | ATCC13032 genome | GEP812 | ATTGAGCGGCTCGAGTAGTTGTTAGGATTCACCAC (SEQ ID NO: 33) |
| | | | Down-R | ATCC13032 genome | GEP813 | TACCGAGCTCGAATTGTTCCCTGGAAATTGTTTGC (SEQ ID NO: 34) |
| pGE228 | ilvB | pGE015 (EcoRI) | Up-F | ATCC13032 genome | GEP956 | GACGGCCAGTGAATTACCGCACGCGACCAGTTATT (SEQ ID NO: 35) |
| | | | Up-R | ATCC13032 genome | GEP957 | GCTAGCGACTTTCTGGCTCCTTTACT (SEQ ID NO: 36) |
| | | | Down-F | ATCC13032 genome | GEP958 | CAGAAAGTCGCTAGCGGAGAGACCCAAGATGGCTA (SEQ ID NO: 37) |
| | | | Down-R | ATCC13032 genome | GEP959 | TACCGAGCTCGAATTCTCGATGTCGTTGGTGAAGA (SEQ ID NO: 38) |

TABLE 16

| Plasmid ID | Deletion target | Target vector | | Template | DNA ID | DNA sequences |
|---|---|---|---|---|---|---|
| pGE253 | cg0931 | pGE015 (EcoRI) | Up-F | ATCC13032 genome | GEP1132 | GACGGCCAGTGAATTAGCAGGGACGAAAGTCGGGA (SEQ ID NO: 39) |
| | | | Up-R | ATCC13032 genome | GEP1133 | CTCGAGGCAGCTACTATATTTGATCC (SEQ ID NO: 40) |
| | | | Down-F | ATCC13032 genome | GEP1134 | AGTAGCTGCCTCGAGTTTGAACAGGITGTTGGGGG (SEQ ID NO: 41) |
| | | | Down-R | ATCC13032 genome | GEP1135 | TACCGAGCTCGAATTATCGACGGCAAAACGCCCAA (SEQ ID NO: 42) |
| pGE1171 | adhE | pGE209 (KpnI, BamHI) | Up-F | ATCC13032 genome | GEP2606 | GTGAATTCGAGCTCGCAGAAGCAGATCTTGCAATC (SEQ ID NO: 43) |
| | | | Up-R | ATCC13032 genome | GEP2607 | CTTCCTCGAGAATTCCAGGCACTACAGTGCTC (SEQ ID NO: 44) |
| | | | Down-F | ATCC13032 genome | GEP2608 | GAATTCTCGAGGAAGAGGCTTTCAACACCATG (SEQ ID NO: 45) |
| | | | Down-R | ATCC13032 genome | GEP2609 | AGGTGGATACGGATCGGAACAAAGTGTCTCCAGAG (SEQ ID NO: 46) |

TABLE 17

| Plasmid ID | Deletion target | Target vector | | Template | DNA ID | DNA sequences |
|---|---|---|---|---|---|---|
| pGE1218 | adhE | pGE209 (KpnI, BamHI) | Up-F | ATCC13032 genome | GEP2688 | GTGAATTCGAGCTCGATTCAGGATTTGCTTCGCGACG (SEQ ID NO: 47) |
| | | | Up-R | ATCC13032 genome | GEP2607 | CTTCCTCGAGAATTCCAGGCACTACAGTGCTC (SEQ ID NO: 44) |
| | | | Down-F | ATCC13032 genome | GEP2608 | GAATTCTCGAGGAAGAGGCTTTCAACACCATG (SEQ ID NO: 45) |
| | | | Down-R | ATCC13032 genome | GEP2689 | AGGTGGATACGGATCACAGTGTCCGGATCATCTGCTG (SEQ ID NO: 48) |
| pGE1172 | ald | PGE209 (KpnI, BamHI) | Up-F | ATCC13032 genome | GEP2610 | GTGAATTCGAGCTCGCCGAAACCTCAAAGAATCCC (SEQ ID NO: 49) |
| | | | Up-R | ATCC13032 genome | GEP2611 | GGTACTCGAGTCCTGGATTTGCGTAGACAGTC (SEQ TD NO: 50) |
| | | | Down-F | ATCC13032 genome | GEP2612 | CAGGACTCGAGTACCAGCAGACCAAGAACCTG (SEQ ID NO: 51) |
| | | | Down-R | ATCC13032 genome | GEP2613 | AGGTGGATACGGATCGATCTCCAGAGGTTTCAAGC (SEQ ID NO: 52) |

TABLE 18

| Plasmid ID | Deletion target | Target vector | Template | | DNA ID | DNA sequences |
|---|---|---|---|---|---|---|
| pGE1221 | ald | pGE209 (KpnI, BamHI) | Up-F | ATCC13032 genome | GEP2692 | gtgaattcgagctcgAACGCCAGATGGTCGTACTTTGC (SEQ ID NO: 53) |
| | | | Up-R | ATCC13032 genome | GEP2611 | GGTACTCGAGTCCTGGATTTGCGTAGACAGTC (SEQ ID NO: 50) |
| | | | Down-F | ATCC13032 genome | GEP2612 | CAGGACTCGAGTACCAGCAGACCAAGAACCTG (SEQ ID NO: 51) |
| | | | Down-R | ATCC13032 genome | GEP2693 | aggtggatacggatcTTCAACACCGCTGATTTCCTACG (SEQ ID NO: 54) |

TABLE 19

| Plasmid ID | Target gene | Target vector | | Template | DNA ID | DNA sequences |
|---|---|---|---|---|---|---|
| pGE403 | KnR | | F | pHSG298 | GEP433 | CGGTACCGTCGACGATATCGAGGTCTGCCTCGTGAAGAA (SEQ LD NO: 55) |
| | | | R | | GEP434 | GCCTTTTTACGGTTCGATTTATTCAACAAAGCCGC (SEQ ID NO: 56) |
| | pUCori | | F | pHSG298 | GEP437 | GAACCGTAAAAAGGCCGCGTTGCTGGCGTUTTCC (SEQ ID NO: 57) |
| | | | R | | GEP438 | GCGGCCGCGTAGAAAAGATCAAAGGATCTTCTTGA (SEQ ID NO: 58) |
| | pCG1ori | | F | pCG1 | GEP445 | TTTCTACGCGGCCGCCCATGGTCGTCACAGAGCTG (SEQ ID NO: 59) |
| | | | R | | GEP446 | TCGTCGACGGTACCGGATCCTTGGGAGCAGTCCTTGTGCG (SEQ ID NO: 60) |

TABLE 20

| Plasmid ID | Target gene | Target vector | | Template | DNA ID | DNA sequences |
|---|---|---|---|---|---|---|
| pGE409 | PgapA | pGE403 | F | ATCC13032 genome | GEP472 | CTGCTCCCAAGGATCGAAGAAATTTAGATGATTGA (SEQ ID NO: 61) |
| | | | R | | GEP478 | CCGTCGACGATATCATATGGTGTCTCCTCTAAAGATTGT (SEQ ID NO: 62) |
| | TrrnB | pGE403 | F | pFLAG-CTC | GEP467 | TGATATCGTCGACGGATCCTGCCTGGCGGCAGTAGCGCG (SEQ ID NO: 63) |
| | | | R | | GEP468 | GAGGCAGACCTCGATAAAAAGGCCATCCGTCAGGA (SEQ ID NO: 64) |

TABLE 21

| Plasmid ID | Target gene | Target vector | | Template | DNA ID | DNA sequences |
|---|---|---|---|---|---|---|
| pGE1031 | Ec_hpaI | pET15b (NdeI) | F | BL21 (DE3) genome | GEP2268 | CGCGCGGCAGCCATATGGAAAACAGTTTTAAAGCG (SEQ ID NO: 65) |
| | | | R | | GEP2269 | GGATUTCCAGGATAttaATACACGCCGCGCTTAATC (SEQ ID NO: 66) |
| pGE1143 | Ec_hpaI | pGE409 | F | pGE1031 | GEP2519 | AGAGGAGACACCATATGGGCAGCAGCCATCATCATC (SEQ ID NO: 67) |
| | | | R | | GEP2518 | CCGCCAGGGAGGATCCTTAATACACGCCGGGCTTAATC (SEQ ID NO: 68) |
| pGE1258 | Ec_rhmA | pGE409 | F | DH5alpha genome | GEP2765 | <u>AGAGGAGACACCAT</u>atgAACGCATTATTAAGCAA (SEQ ID NO: 73) |
| | | | R | | GEP2766 | CCGCCAGGCAGGATCagatcttaATAACTACCTTTTATGCG (SEQ ID NO: 74) |

TABLE 21-continued

| Plasmid ID | Target gene | Target vector | Template | | DNA ID | DNA sequences |
|---|---|---|---|---|---|---|
| pGE1226 | Ec_nanA | pGE409 (NdeI, BamHI) | F | DH5alpha genome | GEP2722 | AGAGGAGACACCATatgGCAACGAATTTACGTGG (SEQ ID NO: 75) |
| | | | R | | GEP2723 | CCGCCAGGCAGGATCctTaCCCGCGCTCTTGCATCAAC (SEQ ID NO: 76) |

TABLE 22

| Plasmid ID | Target gene | Target vector | Template | | DNA ID | DNA sequences |
|---|---|---|---|---|---|---|
| pGE1185 | ΔadhE::hpaI | pGE1171 (XhoI) | F | pGE1143 | GEP2637 | GCCTGGAATTCTCGAGAAGGACTGCTCCCAAGGATCG (SEQ ID NO: 69) |
| | | | R | | GEP2638 | AAGCCTCTTCCTCGATCTTCACGAGGCAGACTC (SEQ ID NO: 70) |
| pGE1186 | Δald::hpaI | pGE1172 (XhoI) | F | pGE1143 | GEP2639 | AAATCCAGGACTCGAGAAGGACTGCTCCCAAGGATCG (SEQ ID NO: 71) |
| | | | R | | GEP2640 | TCTGCTGGTACTCGATCTTCACGAGGCAGACCTC (SEQ ID NO: 72) |
| pGE1302 | Δald::rhmA | pGE1221 (XhoI) | F | pGE1258 | GEP2639 | AAATCCAGGACTCGAGAAGGACTGCTCCCAAGGATCG (SEQ ID NO: 70 |
| | | | R | | GEP2640 | TCTGCTGGTACTCGATCTTCACGAGGCAGACCTC (SEQ ID NC): 72) |

TABLE 23

| Plasmid ID | Target gene | Target vector | Template | | DNA ID | DNA sequences |
|---|---|---|---|---|---|---|
| pGE1304 | ΔadhE::rhmA | pGE1218 (XhoI) | F | pGE1258 | GEP2637 | GCCTGGAATTCTCGAGAAGGACTGCTCCCAAGGATCG (SEQ ID NO: 69) |
| | | | R | | GEP2638 | AAGCCTCTTCCTCGATCTTCACGAGGCAGACCTC (SEQ ID NO: 70) |
| pGE1272 | ΔadhE::nanA | pGE1218 (XhoI) | F | pGE1226 | GEP2637 | GCCTGGAATTCTGGAGAAGGACTGCTCCCAAGGATCG (SEQ ED NO: 69) |
| | | | R | | GEP2638 | AAGCCTCTTCCTCGATCTTCACGAGGCAGACCTC (SEQ ID NO: 70) |
| pGE1273 | Δald::nanA | pGE1221 (XhoI) | F | pGE1226 | GEP2639 | AAATCCAGGACTCGAGAAGGACTGCTCCCAAGGATCG (SEQ ID NO: 71) |
| | | | R | | GEP2640 | TCTGCTGGTACTCGATCTTCACGAGGCAGACCTC (SEQ ID NO: 72) |

TABLE 24

| Plasmid ID | Target gene | Target vector | | Template | DNA ID | DNA sequences |
|---|---|---|---|---|---|---|
| pGE402 | KnR | | F | pHSG298 | GEP433 | CGGTACCGTCGACGATATCGAGGTCTGCCTCGTGAAGAA (SEQ ID NO: 55) |
| | | | R | | GEP434 | GCCTTTTTACGGTTCGATTTATTCAACAAAGCCGC (SEQ ID NO: 56) |
| | pUCori | | F | pHSG298 | GEP437 | GAACCGTAAAAAGGCCGCGTTGCTGGCGTTTTTCC (SEQ ID NO: 57) |
| | | | R | | GEP438 | GCGGCCGCGTAGAAAAGATCAAAGGATCTTCTTGA (SEQ ID NO: 58) |
| | pCASE1ori | | F | pCASE1 | GEP443 | TTTCTACGCGGCCGCCACTGGAAGGGTTCTTCAGG ( SEQ ID NO: 77) |
| | | | R | | GEP444 | TCGTCGACGGTACCGGATCCCTGACTTGGTTACGATGGAC (SEQ ID NO: 78) |

TABLE 25

| Plasmid ID | Target gene | Target vector | | Template | DNA ID | DNA sequences |
|---|---|---|---|---|---|---|
| pGE411 | PldhA | pGE402 | F | ATCC13032 genome | GEP474 | ACCAAGTCAGGGATCGCGGAACTAGCTCTGCAATG (SEQ ID NO: 79) |
| | | | R | | GEP477 | CCGTCGACGATATCATATGCGATCCCACTTCCTGATTTC (SEQ ID NO: 80) |
| | TrrnB | pGE402 | F | pFLAG-CTC | GEP467 | TGATATCGTCGACGGATCCTGCCTGGCGGCAGTAGCGCG (SEQ ID NO: 63) |
| | | | R | | GEP468 | GAGGCAGACCTCGATAAAAAGGCCATCCGTCAGGA (SEQ ID NO: 64) |

TABLE 26

| Plasmid ID | Target gene | Target vector | | Template | DNA ID | DNA sequences |
|---|---|---|---|---|---|---|
| pGE619 | SpR | | F | pCR8/GW/TOPO invitrogen | GEP435 | CGGTACCGTCGACGATATCTCTAGACCAGCCAGGACAGA (SEQ ID NO: 81) |
| | | | R | | GEP436 | GCCTTTTTACGGTTCCTCGAGGGTTATTTGCCGAC (SEQ ID NO: 82) |
| | pUCori | | F | pHSG298 | GEP437 | GAACCGTAAAAAGGCCGCGTTGCTGGCGTTTTTCC (SEQ ID NO: 57) |
| | | | R | | GEP438 | GCGGCCGCGTAGAAAAGATCAAAGGATCTTCTTGA (SEQ ID NO: 58) |
| | pCASE1ori | | F | pCASE1 | GEP443 | TTTCTACGCGGCCGCCACTGGAAGGGTTCTTCAGG (SEQ ID NO: 75) |
| | | | R | | GEP444 | TCGTCGACGGTACCGGATCCCTGACTTGGTTACGATGGAC (SEQ ID NO: 76) |

TABLE 27

| Plasmid ID | Target gene | Target vector | | Template | DNA ID | DNA sequences |
|---|---|---|---|---|---|---|
| pGE945-2 | PldhA | pGE619 | F | ATCC13032 genome | GEP474 | ACCAAGTCAGGGATCGCGGAACTAGCTCTGCAATG (SEQ ID NO: 79) |
| | | | R | | GEP477 | CCGTCGACGATATCATATGCGATCCCACTTCCTGATTTC (SEQ ID NO: 80) |
| | TrrnB | pGE619 | F | pFLAG-CTC | GEP467 | TGATATCGTCGACGGATCCTGCCTGGCGGCAGTAGCGCG (SEQ ID NO: 63) |
| | | | R | | GEP2897 | GGCTGGTCTAGAGATAAAAAGGCCATCCGTCAGGA (SEQ ID NO. 83) |

TABLE 28

| Pladmid ID | Target gene | Target Vector | | Template | Oligo DNA | DNA sequences |
|---|---|---|---|---|---|---|
| pGE1161 | Pp_mdlC | pET15b (NdeI) | F | NBRC 14164 genome | GEP2550 | CGCGCGGCAGCCATATGGCTTCGGTACACGGCAC (SEQ ID NO: 84) |
| | | | R | | GEP2551 | GGATCCTCGAGCATATCACTTCACCGGGCTTACGGTG (SEQ ID NO: 85) |
| pGE1150 | Kp_dhaT | pET15b (NdeI) | F | pHA12-dhaBT | GEP2529 | CGCGCGGCAGCCATATGAGCTATCGTATGTTCGATTATC (SEQ ID NO: 88) |
| | | | R | | GEP2530 | GGATCCTCGAGCATATTAGAATGCCTGGCGGAAAATCG (SEQ ID NO: 89) |

TABLE 29

| Plasmid ID | Target gene | Target vector | | Template | Oligo DNA | DNA sequences |
|---|---|---|---|---|---|---|
| pGE1197 | Pp_mdlC | pGE409 (NdeI) | F | pGE1161 | GEP2653 | AGAGGAGACACCATATGGCTTCGGTACACGGCAC (SEQ ID NO: 86) |
| | | | R | | GEP2654 | GTCGACGATATCATATCACTTCACCGGGCTTACGGT (SEQ ID NO: 87) |

TABLE 29-continued

| Plasmid ID | Target gene | Target vector | Template | Oligo DNA | DNA sequences |
|---|---|---|---|---|---|
| pGE1190 | Kp_dhaT | pGE945-2 (NdeI, BamHI) | pGE1150 | F R | ligation |

TABLE 30

| Strain ID | Host strain | Plasmid |
|---|---|---|
| ATCC13032 | — | — |
| GES007 | Δppc | — |
| GES048 | ΔppcΔldhA | — |
| GES1041 | ΔppcΔldhAΔadhE | — |
| GES1070 | ΔppcΔldhAΔadhEΔald | — |
| GES1052 | ΔppcΔldhA ΔadhEΔald::PgapA-hpal | — |
| GES1063 | ΔppcΔldhA ΔadhE::PgapA-hpalΔald::PgapA-hpal | — |
| GES1188 | ΔppcΔldhA ΔadhEΔald::PgapA-nanA | — |
| GES1223 | ΔppcΔldhA ΔadhE::PgapA-nanAΔald::PgapA-nanA | — |
| GES1215 | ΔppcΔldhA ΔadhEΔald:: PgapA-rhmA | — |
| GES1242 | ΔppcΔldhA ΔadhE::PgapA-rhmAΔald:: PgapA-rhmA | — |
| GES1253 | ΔppcΔldhA ΔadhEΔald | pGE1197 PgapA-Pp_mdlC (pCG1, Km) pGE1190 PldhA-Kp_dhaT (pCASE1, Sp) |

TABLE 31

| Strain ID | Host strain | Plasmid |
|---|---|---|
| GES1077 | ΔppcΔldhA ΔadhE::PgapA-hpalΔald::PgapA-hpal | pGE1197 PgapA-Pp_mdlC (pCG1, Km) pGE1190 PldhA-Kp_dhaT (pCASE1, Sp) |
| GES1253 | ΔppcΔldhA ΔadhE::PgapA-nanAΔald:: PgapA-nanA | pGE1197 PgapA-Pp_mdlC (pCG1, Km) pGE1190 PldhA-Kp_dhaT (pCASE1, Sp) |
| GES1282 | ΔppcΔldhA ΔadhE::PgapA-rhmAΔald:: PgapA-rhmA | pGE1197 PgapA-Pp_mdlC (pCG1, Km) pGE1190 PldhA-Kp_dhaT (pCASE1, Sp) |

TABLE 32

| Strain ID | Host strain | Plasmid |
|---|---|---|
| GES385 | ΔppcΔldhA Δpyc | — |
| GES388 | ΔppcΔldhA ΔpycΔpoxB | — |
| GES393 | ΔppcΔldhA ΔpycΔpoxBΔalaA | — |
| GES405 | ΔppcΔldhA ΔpycΔpoxBΔalaAΔilvB | — |
| GES435 | ΔppcΔldhA ΔpycΔpoxBΔalaAΔilvBΔcg0931 | — |
| GES1042 | ΔppcΔldhA ΔpycΔpoxBΔalaAΔilvBΔcg0931 ΔadhE | — |
| GES1211 | ΔppcΔldhA ΔpycΔpoxBΔalaAΔilvBΔcg0931 ΔadhEΔald | — |
| GES1053 | ΔppcΔldhA ΔpycΔpoxBΔalaAΔilvBΔcg0931 ΔadhEΔald::PgapA-hpal | — |

TABLE 33

| Strain ID | Host strain | Plasmid |
|---|---|---|
| GES1064 | ΔppcΔldhA ΔpycΔpoxBΔalaAΔilvBΔcg0931 ΔadhE::PgapA-hpalΔald::PgapA-hpal | — |

TABLE 33-continued

| Strain ID | Host strain | Plasmid |
|---|---|---|
| GES1189 | ΔppcΔldhA ΔpycΔpoxBΔalaAΔilvBΔcg0931 ΔadhEΔald::PgapA-nanA | — |
| GES1233 | ΔppcΔldhA ΔpycΔpoxBΔalaAΔilvBΔcg0931 ΔadhE::PgapA-nanAΔald::PgapA-nanA | — |
| GES1068 | ΔppcΔldhA ΔpycΔpoxBΔalaAΔilvBΔcg0931 ΔadhE::PgapA-hpalΔald::PgapA-hpal | pGE1197 PgapA-Pp_mdlC (pCG1, Km) pGE1190 PldhA-Kp_dhaT (pCASE1, Sp) |
| GES1254 | ΔppcΔldhA ΔpycΔpoxBΔalaAΔilvBΔcg0931 ΔadhE::PgapA-nanAΔald:: PgapA-nanA | pGE1197 PgapA-Pp_mdlC (pCG1, Km) pGE1190 PldhA-Kp_dhaT (pCASE1, Sp) |

2. Plasmid Construction

(2-1) Gene Deletion

2-1-(1) Construction of Plasmid for Gene Disruption

Using pNIC28-Bsa4 (manufactured by Source BioScience) as a template, and using DNAs of base sequences represented by GEP007 (SEQ ID NO: 11) and GEP008 (SEQ ID NO: 12), a DNA fragment [Mol. Microbiol., 6, 1195 (1992)] containing a sacB gene derived from *Bacillus subtilis* was amplified by the PCR method. This PCR product was treated with BamHI and PstI, and after performing agarose gel electrophoresis, the DNA fragment was extracted and purified. In addition, a plasmid pHSG299 (manufactured by Takara Bio Inc.) having a gene conferring resistance to kanamycin was treated with BamHI and PstI, and after performing agarose gel electrophoresis, the DNA fragment was extracted and purified. These two DNA fragments were ligated using a DNA Ligation Kit, <Mighty Mix> (manufactured by Takara Bio Inc.) according to the attached instructions, and thereby a plasmid pGE015 was obtained.

For the purpose of deleting a KpnI recognition site that pGE015 has on sacB, using pGE015 as a template, and using DNAs of base sequences represented by GEP808 (SEQ ID NO: 13) and GEP809 (SEQ ID NO: 14), mutagenesis and plasmid amplification were carried out using a PrimeSTAR (registered trademark) Mutagenesis Basal Kit (manufactured by Takara Bio Inc.) according to the attached instructions. Thereby, pGE209 was obtained.

2-1-(2) Construction of Plasmid for Creating ppc-Gene-Disrupted Strain

A *Corynebacterium glutamicum* ATCC13032 strain was obtained as a NBRC12168 strain from the Biotechnology Center of the National Institute of Technology and Evaluation, cultured according to the attached instructions, and then genomic DNA extraction was performed.

Using a genomic DNA of the ATCC13032 strain as a template, and using a combination of DNAs of base sequences represented by GEP132 (SEQ ID NO: 15) and GEP133 (SEQ ID NO: 16), and a combination of DNAs of base sequences represented by GEP134 (SEQ ID NO: 17) and GEP135 (SEQ ID NO: 18), two types of PCR products were obtained by the PCR method, agarose gel electrophoresis was performed thereon, and then extraction and purification were performed. In addition, pGE015 was treated with EcoRI, agarose gel electrophoresis was performed thereon, and then extraction and purification were performed. These three DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 50 μg/ml of kanamycin. This transformant was cultured in a B medium containing 50 μg/ml of kanamycin, and plasmid extraction was performed using the obtained culture suspension. The plasmid thus obtained was designated as pGE020.

2-1-(3) Creation of ppc-Gene-Deleted Strain

A *Corynebacterium glutamicum* ATCC13032 strain was transformed by electroporation using pGE020, and a kanamycin-resistant strain was selected on an A medium containing 25 μg/ml of kanamycin at 33° C. Next, the obtained kanamycin-resistant strain was spread on a Suc agar medium and cultured at 33° C. The grown colonies were further cultured in the A medium, and a strain lacking a ppc gene was selected by colony PCR. The strain thus obtained was named GES007.

2-1-(4) Construction of Plasmid for Creating ldhA-Gene-Disrupted Strain

Using a genomic DNA of the ATCC13032 strain as a template, and using a combination of DNAs of base sequences represented by GEP169 (SEQ ID NO: 19) and GEP170 (SEQ ID NO: 20), and a combination of DNAs of base sequences represented by GEP215 (SEQ ID NO: 21) and GEP216 (SEQ ID NO: 22), two types of PCR products were obtained by the PCR method, agarose gel electrophoresis was performed thereon, and then extraction and purification were performed. In addition, pGE015 was treated with EcoRI, agarose gel electrophoresis was performed thereon, and then extraction and purification were performed. These three DNA fragments were mixed, and a plasmid obtained by the same operation as in the creation of pGE020 was designated as pGE033.

2-1-(5) Creation of ldhA-Gene-Deleted Strain

Using pGE033, GES007 was transformed by electroporation, and a strain selected by the same operation as in the creation of GES007 was named GES048.

2-1-(6) Construction of Plasmid for Creating Pyc-Gene-Disrupted Strain

Using a genomic DNA of the ATCC13032 strain as a template, and using a combination of DNAs of base sequences represented by GEP615 (SEQ ID NO: 23) and GEP616 (SEQ ID NO: 24), and a combination of DNAs of base sequences represented by GEP617 (SEQ ID NO: 25) and GEP618 (SEQ ID NO: 26), two types of PCR products were obtained by the PCR method, agarose gel electrophoresis was performed thereon, and then extraction and purification were performed. In addition, pGE015 was treated with EcoRI, agarose gel electrophoresis was performed thereon, and then extraction and purification were performed. These three DNA fragments were mixed, and a plasmid obtained by the same operation as in the creation of pGE020 was designated as pGE177.

2-1-(7) Creation of Pyc-Gene-Deleted Strain

Using pGE177, GES048 was transformed by electroporation, and a strain selected by the same operation as in the creation of GES007 was named GES385.

2-1-(8) Construction of Plasmid for Creating poxB-Gene-Disrupted Strain

Using a genomic DNA of the ATCC13032 strain as a template, and using a combination of DNAs of base sequences represented by GEP406 (SEQ ID NO: 27) and GEP407 (SEQ ID NO: 28), and a combination of DNAs of base sequences represented by GEP698 (SEQ ID NO: 29) and GEP409 (SEQ ID NO: 30), two types of PCR products were obtained by the PCR method, agarose gel electrophoresis was performed thereon, and then extraction and purification were performed. In addition, pGE015 was treated with EcoRI, agarose gel electrophoresis was performed thereon, and then extraction and purification were performed. These three DNA fragments were mixed, and a plasmid obtained by the same operation as in the creation of pGE020 was designated as pGE191.

2-1-(9) Creation of poxB-Gene-Deleted Strain

Using pGE191, GES385 was transformed by electroporation, and a strain selected by the same operation as in the creation of GES007 was named GES388.

2-1-(10) Construction of Plasmid for Creating alaA-Gene-Disrupted Strain

Using a genomic DNA of the ATCC13032 strain as a template, and using a combination of DNAs of base sequences represented by GEP810 (SEQ ID NO: 31) and GEP811 (SEQ ID NO: 32), and a combination of DNAs of base sequences represented by GEP812 (SEQ ID NO: 33) and GEP813 (SEQ ID NO: 34), two types of PCR products were obtained by the PCR method, agarose gel electrophoresis was performed thereon, and then extraction and purification were performed. In addition, pGE015 was treated with EcoRI, agarose gel electrophoresis was performed thereon, and then extraction and purification were performed. These three DNA fragments were mixed, and a plasmid obtained by the same operation as in the creation of pGE020 was designated as pGE210.

2-1-(11) Creation of alaA-Gene-Deleted Strain

Using pGE210, GES388 was transformed by electroporation, and a strain selected by the same operation as in the creation of GES007 was named GES393.

2-1-(12) Construction of Plasmid for Creating ilvB-Gene-Disrupted Strain

Using a genomic DNA of the ATCC13032 strain as a template, and using a combination of DNAs of base sequences represented by GEP956 (SEQ ID NO: 35) and GEP957 (SEQ ID NO: 36), and a combination of DNAs of base sequences represented by GEP958 (SEQ ID NO: 37) and GEP959 (SEQ ID NO: 38), two types of PCR products were obtained by the PCR method, agarose gel electrophoresis was performed thereon, and then extraction and purification were performed. In addition, pGE015 was treated with EcoRI, agarose gel electrophoresis was performed thereon, and then extraction and purification were performed. These three DNA fragments were mixed, and a plasmid obtained by the same operation as in the creation of pGE020 was designated as pGE228.

2-1-(13) Creation of ilvB-Gene-Deleted Strain

Using pGE228, GES393 was transformed by electroporation, and a strain selected by the same operation as in the creation of GES007 was named GES405.

2-1-(14) Construction of Plasmid for Creating cg0931-Gene-Disrupted Strain

Using a genomic DNA of the ATCC13032 strain as a template, and using a combination of DNAs of base sequences represented by GEP1132 (SEQ ID NO: 39) and GEP1133 (SEQ ID NO: 40), and a combination of DNAs of base sequences represented by GEP1134 (SEQ ID NO: 41) and GEP1135 (SEQ ID NO: 42), two types of PCR products were obtained by the PCR method, agarose gel electrophoresis was performed thereon, and then extraction and purification were performed. In addition, pGE015 was treated with EcoRI, agarose gel electrophoresis was performed thereon, and then extraction and purification were performed. These three DNA fragments were mixed, and a plasmid obtained by the same operation as in the creation of pGE020 was designated as pGE253.

2-1-(15) Creation of cg0931-Gene-Deleted Strain

Using pGE253, GES405 was transformed by electroporation, and a strain selected by the same operation as in the creation of GES007 was named GES435.

2-1-(16) Construction of Plasmid for Creating adhE-Gene-Disrupted Strain

Using a genomic DNA of the ATCC13032 strain as a template, and using a combination of DNAs of base sequences represented by GEP2606 (SEQ ID NO: 43) and GEP2607 (SEQ ID NO: 44), and a combination of DNAs of base sequences represented by GEP2608 (SEQ ID NO: 45) and GEP2609 (SEQ ID NO: 46), two types of PCR products were obtained by the PCR method, agarose gel electrophoresis was performed thereon, and then extraction and purification were performed. In addition, pGE209 was treated with KpnI and BamHI, agarose gel electrophoresis was performed thereon, and then extraction and purification were performed. These three DNA fragments were mixed, and a plasmid obtained by the same operation as in the creation of pGE020 was designated as pGE1171.

Using a genomic DNA of the ATCC13032 strain as a template, and using a combination of DNAs of base sequences represented by GEP2688 (SEQ ID NO: 47) and GEP2607 (SEQ ID NO: 44), and a combination of DNAs of base sequences represented by GEP2608 (SEQ ID NO: 45) and GEP2689 (SEQ ID NO: 48), two types of PCR products were obtained by the PCR method, agarose gel electrophoresis was performed thereon, and then extraction and purification were performed. In addition, pGE209 was treated with KpnI and BamHI, agarose gel electrophoresis was performed thereon, and then extraction and purification were performed. These three DNA fragments were mixed, and a plasmid obtained by the same operation as in the creation of pGE020 was designated as pGE1218.

2-1-(17) Creation of adhE-Gene-Deleted Strain

Using pGE1171, GES048 was transformed by electroporation, and a strain selected by the same operation as in the creation of GES007 was named GES1041.

2-1-(18) Construction of Plasmid for Creating Ald-Gene-Disrupted Strain

Using a genomic DNA of the ATCC13032 strain as a template, and using a combination of DNAs of base sequences represented by GEP2610 (SEQ ID NO: 49) and GEP2611 (SEQ ID NO: 50), and a combination of DNAs of base sequences represented by GEP2612 (SEQ ID NO: 51) and GEP2613 (SEQ ID NO: 52), two types of PCR products were obtained by the PCR method, agarose gel electrophoresis was performed thereon, and then extraction and purification were performed. In addition, pGE209 was treated with KpnI and BamHI, agarose gel electrophoresis was performed thereon, and then extraction and purification were performed. These three DNA fragments were mixed, and a plasmid obtained by the same operation as in the creation of pGE020 was designated as pGE1172.

Using a genomic DNA of the ATCC13032 strain as a template, and using a combination of DNAs of base sequences represented by GEP2692 (SEQ ID NO: 53) and GEP2611 (SEQ ID NO: 50), and a combination of DNAs of base sequences represented by GEP2612 (SEQ ID NO: 51) and GEP2693 (SEQ ID NO: 54), two types of PCR products were obtained by the PCR method, agarose gel electrophoresis was performed thereon, and then extraction and purification were performed. In addition, pGE209 was treated with KpnI and BamHI, agarose gel electrophoresis was performed thereon, and then extraction and purification were performed. These three DNA fragments were mixed, and a plasmid obtained by the same operation as in the creation of pGE020 was designated as pGE1221.

2-1-(19) Creation of Ald-Gene-Deleted Strain

Using pGE1172, GES1041 was transformed by electroporation, and a strain selected by the same operation as in the creation of GES007 was named GES1070.

(2-2) Gene Replacement 2-2-(1) Construction of pGE409

Using pHSG298 (manufactured by Takara Bio Inc.) as a template, and using a combination of DNAs of base sequences represented by GEP433 (SEQ ID NO: 55) and GEP434 (SEQ ID NO: 56), and a combination of DNAs of base sequences represented by GEP437 (SEQ ID NO: 57) and GEP438 (SEQ ID NO: 58), PCR products were obtained by the PCR method, agarose gel electrophoresis was performed thereon, and then extraction and purification were performed. These are DNA fragments respectively containing a kanamycin-resistant gene and a replication origin, pUCori for *Escherichia coli*.

A *Corynebacterium glutamicum* NBRC12169 strain was obtained from the Biotechnology Center of the National Institute of Technology and Evaluation and cultured according to the attached instructions, and the bacterial cells were recovered by centrifugation. The bacterial cell pellet was washed with 1 mL of a buffer solution of 10 mM cyclohexylene dinitrilotetraacetic acid and 25 mM Tris-HCl (pH 8.0), centrifuged at 6,000×g and 4° C. for 5 minutes, and recovered again. The bacterial cell pellet was suspended in 300 µL of Buffer A1 containing 15 mg/ml lysozyme (attached to NucleoSpin (registered trademark) Plasmid EasyPure manufactured by MACHEREY-NAGEL GmbH & Co. KG) and shaken at 37° C. for 2 hours. Thereafter, a pCG1 plasmid was extracted and purified according to the attached instructions of NucleoSpin (registered trademark) Plasmid EasyPure. Using this as a template, and using a combination of DNAs of base sequences represented by GEP445 (SEQ ID NO: 59) and GEP446 (SEQ ID NO: 60), PCR products were obtained by the PCR method, agarose gel electrophoresis was performed thereon, and then extraction and purification were performed. This is a DNA fragment containing a replication origin, pCGlori for *Corynebacterium*.

The above three DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 50 µg/ml of kanamycin. This transformant was cultured in an LB medium containing 50 µg/ml of kanamycin, and plasmid extraction was performed using the obtained culture suspension. The plasmid thus obtained was designated as pGE403.

Using a genomic DNA of the ATCC13032 strain as a template, and using a combination of DNAs of base sequences represented by GEP472 (SEQ ID NO: 61) and GEP478 (SEQ ID NO: 62), PCR products were obtained by the PCR method, agarose gel electrophoresis was performed thereon, and then extraction and purification were performed. In addition, using pFLAG-CTC (manufactured by Sigma-Aldrich) as a template, and using a combination of DNAs of base sequences represented by GEP467 (SEQ ID NO: 63) and GEP468 (SEQ ID NO: 64), PCR products were obtained by the PCR method, agarose gel electrophoresis was performed thereon, and then extraction and purification were performed. These are DNA fragments respectively containing a gap A promoter (PgapA) and an *E. coli*-ribosomal-RNA-transcriptional terminator (TrrnB) of the ATCC 13032 strain. In addition, pGE403 was treated with BamHI and EcoRV, agarose gel electrophoresis was performed thereon, and then extraction and purification were performed. These three DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 50 µg/ml of kanamycin. This transformant was cultured in an LB medium containing 50 µg/ml of kanamycin, and plasmid extraction was performed using the obtained culture suspension. The plasmid thus obtained was designated as pGE409.

2-2-(2) Construction of pGE1185 (Plasmid for Creating ΔadhE::hpaI-Substituted Strain)

ECOS™ Competent *E. coli* BL21 (DE3) (manufactured by NIPPON GENE CO., LTD.) was purchased, inoculated into an LB agar medium under aseptic conditions, and cultured at 37° C. The bacterial cells grown on the agar medium were inoculated into 10 mL of the LB medium, and the grown bacterial cells were recovered and subjected to genomic DNA extraction. Using a genomic DNA of the BL21 (DE3) strain as a template, and using a combination of DNAs of base sequences represented by GEP2268 (SEQ ID NO: 65) and GEP2269 (SEQ ID NO: 66), PCR products were obtained by the PCR method, agarose gel electrophoresis was performed thereon, and then extraction and purification were performed. This is a DNA fragment containing a hpaI gene (Ec_hpaI) of the *Escherichia coli* BL21 (DE3) strain. In addition, pET-15b (manufactured by Novagen) was treated with NdeI, agarose gel electrophoresis was performed thereon, and then extraction and purification were performed. These two DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 100 μg/ml of ampicillin. This transformant was cultured in an LB medium containing 100 μg/ml of ampicillin, and plasmid extraction was performed using the obtained culture suspension. In this manner, a plasmid pGE1031 in which Ec_hpaI was cloned into pET-15b was obtained.

Using pGE1031 as a template, and using a combination of DNAs of base sequences represented by GEP2519 (SEQ ID NO: 67) and GEP2518 (SEQ ID NO: 68), PCR products were obtained by the PCR method, agarose gel electrophoresis was performed thereon, and then extraction and purification were performed. In addition, pGE409 was treated with NdeI and BamHI, agarose gel electrophoresis was performed thereon, and then extraction and purification were performed. These two DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 50 μg/ml of kanamycin. This transformant was cultured in an LB medium containing 50 μg/ml of kanamycin, and plasmid extraction was performed using the obtained culture suspension. In this manner, a plasmid pGE1143 in which Ec_hpaI was subcloned into pGE409 was obtained.

Using pGE1143 as a template, and using a combination of DNAs of base sequences represented by GEP2637 (SEQ ID NO: 69) and GEP2638 (SEQ ID NO: 70), PCR products were obtained by the PCR method, agarose gel electrophoresis was performed thereon, and then extraction and purification were performed. This is a DNA fragment containing PgapA-hpaI-TrrnB. In addition, pGE1171 was treated with XhoI, agarose gel electrophoresis was performed thereon, and then extraction and purification were performed. These two DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 50 μg/ml of kanamycin. This transformant was cultured in an LB medium containing 50 μg/ml of kanamycin, and plasmid extraction was performed using the obtained culture suspension. The plasmid thus obtained was designated as pGE1185.

2-2-(3) Construction of pGE1186 (Plasmid for Creating Δald::hpaI-Substituted Strain)

Using pGE1143 as a template, and using a combination of DNAs of base sequences represented by GEP2639 (SEQ ID NO: 71) and GEP2640 (SEQ ID NO: 72), PCR products were obtained by the PCR method, agarose gel electrophoresis was performed thereon, and then extraction and purification were performed. This is a DNA fragment containing PgapA-hpaI-TrrnB. In addition, pGE1172 was treated with XhoI, agarose gel electrophoresis was performed thereon, and then extraction and purification were performed. These two DNA fragments were mixed, and a plasmid obtained by the same operation as in the creation of pGE1185 was designated as pGE1186.

2-2-(4) Creation of ΔadhE::hpaI- and Δald::hpaI-Substituted Strains

GES1041 was transformed by electroporation using pGE1186, and a kanamycin-resistant strain was selected on an A medium containing 25 μg/ml of kanamycin at 33° C. Next, the obtained kanamycin-resistant strain was spread on a Suc agar medium and cultured at 33° C. The grown colonies were further cultured in the A medium, and a strain in which the ald gene was substituted by PgapA-hpaI-TrrnB was selected by colony PCR. This was named GES1052. Furthermore, using pGE1185, GES1052 was transformed by electroporation, and a strain in which PgapA-hpaI-TrrnB was inserted at the position of the adhE gene was selected by the same operation as in the creation of GES1052. This was named GES1063.

Using pGE1171, GES435 was transformed by electroporation, and a strain selected by the same operation as in the creation of GES007 was named GES1042. Furthermore, using pGE1186, GES1042 was transformed by electroporation, and a strain in which the ald gene was substituted by PgapA-hpaI-TrrnB was selected by the same operation as in the creation of GES1052. This was named GES1053. Using pGE1185, GES1053 was transformed by electroporation, and a strain in which PgapA-hpaI-TrrnB was inserted at the position of the adhE gene was selected by the same operation as in the creation of GES1052. This was named GES1064.

2-2-(5) Construction of pGE1304 (Plasmid for Creating ΔadhE::rhmA-Substituted Strain)

*E. coli* DH5α Competent Cells (manufactured by Takara Bio Inc.) was purchased, inoculated into an LB agar medium under aseptic conditions, and cultured at 37° C. The bacterial cells grown on the agar medium were inoculated into 10 mL of the LB medium, and the grown bacterial cells were recovered and subjected to genomic DNA extraction. Using a genomic DNA of the DH5α strain as a template, and using a combination of DNAs of base sequences represented by GEP2765 (SEQ ID NO: 73) and GEP2766 (SEQ ID NO: 74), PCR products were obtained by the PCR method, agarose gel electrophoresis was performed thereon, and then extraction and purification were performed. This is a DNA fragment containing a rhmA gene (Ec_rhmA) of the *Escherichia coli* DH5α strain. In addition, pGE409 was treated with NdeI and BamHI, agarose gel electrophoresis was performed thereon, and then extraction and purification were performed. These two DNA fragments were mixed, and a plasmid pGE1258 in which Ec_rhmA was cloned into pGE409 was obtained by the same operation as in the creation of pGE1143.

Using pGE1258 as a template, and using a combination of DNAs of base sequences represented by GEP2637 (SEQ ID NO: 69) and GEP2638 (SEQ ID NO: 70), PCR products were obtained by the PCR method, agarose gel electrophoresis was performed thereon, and then extraction and purification were performed. This is a DNA fragment containing PgapA-rhmA-TrrnB. In addition, pGE1218 was treated with XhoI, agarose gel electrophoresis was performed thereon, and then extraction and purification were performed. These two DNA fragments were mixed, and a plasmid obtained by the same operation as in the creation of pGE1185 was designated as pGE1304.

2-2-(6) Construction of pGE1302 (Plasmid for Creating Δald::rhmA-Substituted Strain)

Using pGE1258 as a template, and using a combination of DNAs of base sequences represented by GEP2639 (SEQ ID NO: 71) and GEP2640 (SEQ ID NO: 72), PCR products were obtained by the PCR method, agarose gel electrophoresis was performed thereon, and then extraction and purification were performed. In addition, pGE1221 was treated with XhoI, agarose gel electrophoresis was performed thereon, and then extraction and purification were performed. This is a DNA fragment containing PgapA-rhmA-TrrnB. These two DNA fragments were mixed, and a plasmid obtained by the same operation as in the creation of pGE1185 was designated as pGE1302.

2-2-(7) Creation of ΔadhE::rhmA- and Δald::rhmA-Substituted Strains

Using pGE1302, GES1041 was transformed by electroporation, and a strain in which the ald gene was substituted by PgapA-rhmA-TrrnB was selected by the same operation as in the creation of GES1052. This was named GES1215. Furthermore, using pGE1304, GES1215 was transformed by electroporation, and a strain in which PgapA-rhmA-TrrnB was inserted at the position of the adhE gene was selected by the same operation as in the creation of GES1052. This was named GES1242.

2-2-(8) Construction of pGE1272 (Plasmid for Creating ΔadhE::nanA-Substituted Strain)

*E. coli* DH5α Competent Cells (manufactured by Takara Bio Inc.) was purchased, inoculated into an LB agar medium under aseptic conditions, and cultured at 37° C. The bacterial cells grown on the agar medium were inoculated into 10 mL of the LB medium, and the grown bacterial cells were recovered and subjected to genomic DNA extraction. Using a genomic DNA of the DH5α strain as a template, and using a combination of DNAs of base sequences represented by GEP2722 (SEQ ID NO: 75) and GEP2723 (SEQ ID NO: 76), PCR products were obtained by the PCR method, agarose gel electrophoresis was performed thereon, and then extraction and purification were performed. This is a DNA fragment containing a nanA gene (Ec_nanA) of the *Escherichia coli* DH5α strain. In addition, pGE409 was treated with NdeI and BamHI, agarose gel electrophoresis was performed thereon, and then extraction and purification were performed. These two DNA fragments were mixed, and a plasmid pGE1226 in which Ec_nanA was cloned into pGE409 was obtained by the same operation as in the creation of pGE1143.

Using pGE1226 as a template, and using a combination of DNAs of base sequences represented by GEP2637 (SEQ ID NO: 69) and GEP2638 (SEQ ID NO: 70), PCR products were obtained by the PCR method, agarose gel electrophoresis was performed thereon, and then extraction and purification were performed. This is a DNA fragment containing PgapA-nanA-TrrnB. In addition, pGE1218 was treated with XhoI, agarose gel electrophoresis was performed thereon, and then extraction and purification were performed. These two DNA fragments were mixed, and a plasmid obtained by the same operation as in the creation of pGE1185 was designated as pGE1272.

2-2-(9) Construction of pGE1273 (Plasmid for Creating Δald::nanA-Substituted Strain)

Using pGE1226 as a template, and using a combination of DNAs of base sequences represented by GEP2639 (SEQ ID NO: 71) and GEP2640 (SEQ ID NO: 72), PCR products were obtained by the PCR method, agarose gel electrophoresis was performed thereon, and then extraction and purification were performed. In addition, pGE1221 was treated with XhoI, agarose gel electrophoresis was performed thereon, and then extraction and purification were performed. This is a DNA fragment containing PgapA-nanA-TrrnB. These two DNA fragments were mixed, and a plasmid obtained by the same operation as in the creation of pGE1185 was designated as pGE1273.

2-2-(10) Creation of ΔadhE::nanA- and Δald::nanA-Substituted Strains

Using pGE1273, GES1041 was transformed by electroporation, and a strain in which the ald gene was substituted by PgapA-nanA-TrrnB was selected by the same operation as in the creation of GES1052. This was named GES1188. Furthermore, using pGE1272, GES1188 was transformed by electroporation, and a strain in which PgapA-nanA-TrrnB was inserted at the position of the adhE gene was selected by the same operation as in the creation of GES1052. This was named GES1223.

Using pGE1273, GES1042 was transformed by electroporation, and a strain in which the ald gene was substituted by PgapA-nanA-TrrnB was selected by the same operation as in the creation of GES1052. This was named GES1189. Furthermore, using pGE1272, GES1189 was transformed by electroporation, and a strain in which PgapA-nanA-TrrnB was inserted at the position of the adhE gene was selected by the same operation as in the creation of GES1052. This was named GES1233.

(2-3) Gene Overexpression Plasmid 2-3-(1) Construction of pGE411

Using pHSG298 (manufactured by Takara Bio Inc.) as a template, and using a combination of DNAs of base sequences represented by GEP433 (SEQ ID NO: 55) and GEP434 (SEQ ID NO: 56), and a combination of DNAs of base sequences represented by GEP437 (SEQ ID NO: 57) and GEP438 (SEQ ID NO: 58), PCR products were obtained by the PCR method, agarose gel electrophoresis was performed thereon, and then extraction and purification were performed. These are DNA fragments respectively containing a kanamycin-resistant gene and a replication origin, pUCori for *Escherichia coli*.

A *Corynebacterium casei* strain JCM12072 was obtained from RIKEN BioResource Research Center and cultured according to the attached instructions, and the bacterial cells were recovered by centrifugation. The bacterial cell pellet was suspended in 1 mL of a buffer solution of 10 mM cyclohexylene dinitrilotetraacetic acid and 25 mM Tris-HCl (pH 8.0), centrifuged at 6,000×g and 4° C. for 5 minutes, and recovered again. The bacterial cell pellet was suspended in 300 µL of Buffer A1 containing 15 mg/ml lysozyme (attached to NucleoSpin (registered trademark) Plasmid Easy-Pure manufactured by MACHEREY-NAGEL GmbH & Co. KG) and shaken at 37° C. for 2 hours. Thereafter, a pCASE1 plasmid was extracted and purified according to the attached instructions of NucleoSpin (registered trademark) Plasmid EasyPure. Using this as a template, and using a combination of DNAs of base sequences represented by GEP443 (SEQ ID NO: 77) and GEP444 (SEQ ID NO: 78), PCR products were obtained by the PCR method, agarose gel electrophoresis was performed thereon, and then extraction and purification were performed. This is a DNA fragment containing a replication origin, pCASE1ori for *Corynebacterium*.

The above three DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 50 µg/ml of kanamycin. This transformant was cultured in an LB medium containing 50 µg/ml of kanamycin, and plasmid extraction was performed using the obtained culture suspension. The plasmid thus obtained was designated as pGE402.

Using a genomic DNA of the ATCC13032 strain as a template, and using a combination of DNAs of base sequences represented by GEP474 (SEQ ID NO: 79) and GEP477 (SEQ ID NO: 80), PCR products were obtained by the PCR method, agarose gel electrophoresis was performed thereon, and then extraction and purification were performed. In addition, using pFLAG-CTC (manufactured by Sigma-Aldrich) as a template, and using a combination of DNAs of base sequences represented by GEP467 (SEQ ID NO: 63) and GEP468 (SEQ ID NO: 64), PCR products were obtained by the PCR method, agarose gel electrophoresis was performed thereon, and then extraction and purification were performed. These are DNA fragments respectively containing a ldhA promoter (PldhA) and an *E. coli*-ribosomal-RNA-transcriptional terminator (TrrnB) of the ATCC 13032 strain. In addition, pGE402 was treated with BamHI and EcoRV, agarose gel electrophoresis was performed thereon, and then extraction and purification were performed. These three DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 50 µg/ml of kanamycin. This transformant was cultured in an LB medium containing 50 µg/ml of kanamycin, and plasmid extraction was performed using the obtained culture suspension. The plasmid thus obtained was designated as pGE411.

2-3-(2) Construction of pGE945-2

Using pCR8/GW/TOPO (manufactured by Invitrogen) as a template, and using a combination of DNAs of base sequences represented by GEP435 (SEQ ID NO: 81) and GEP436 (SEQ ID NO: 82), PCR products were obtained by the PCR method, agarose gel electrophoresis was performed thereon, and then extraction and purification were performed. In addition, using pHSG298 (manufactured by Takara Bio Inc.) as a template, and using a combination of DNAs of base sequences represented by GEP437 (SEQ ID NO: 57) and GEP438 (SEQ ID NO: 58), PCR products were obtained by the PCR method, agarose gel electrophoresis was performed thereon, and then extraction and purification were performed. These are DNA fragments respectively containing a spectinomycin-resistant gene and a replication origin, pUCori for *Escherichia coli*.

The above two DNA fragments, and the DNA fragments containing pCASE1ori obtained when creating pGE402 were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 100 µg/ml of spectinomycin. This transformant was cultured in an LB medium containing 100 µg/ml of spectinomycin, and plasmid extraction was performed using the obtained culture suspension. The plasmid thus obtained was designated as pGE619.

Using a genomic DNA of the ATCC13032 strain as a template, and using a combination of DNAs of base sequences represented by GEP474 (SEQ ID NO: 79) and GEP477 (SEQ ID NO: 80), PCR products were obtained by the PCR method, agarose gel electrophoresis was performed thereon, and then extraction and purification were performed. In addition, using pFLAG-CTC (manufactured by Sigma-Aldrich) as a template, and using a combination of DNAs of base sequences represented by GEP467 (SEQ ID NO: 63) and GEP2897 (SEQ ID NO: 83), PCR products were obtained by the PCR method, agarose gel electrophoresis was performed thereon, and then extraction and purification were performed. These are DNA fragments respectively containing a ldhA promoter (PldhA) and an *E. coli*-ribosomal-RNA-transcriptional terminator (TrrnB) of the ATCC 13032 strain. In addition, pGE619 was treated with BamHI and EcoRV, agarose gel electrophoresis was performed thereon, and then extraction and purification were performed. These three DNA fragments were mixed, and a binding reaction of the DNA fragments was performed using an In-Fusion (registered trademark) HD Cloning Kit according to the attached instructions. Using the reaction products, *E. coli* DH5α Competent Cells (manufactured by Takara Bio Inc.) were transformed according to the attached instructions. A target transformant was selected by culturing on an LB agar medium containing 100 µg/ml of spectinomycin. This transformant was cultured in an LB medium containing 100 µg/ml of spectinomycin, and plasmid extraction was performed using the obtained culture suspension. The plasmid thus obtained was designated as pGE945-2.

2-3-(3) Construction of Pp_mdIC Overexpression Plasmid

A *Pseudomonas putida* NBRC14164 strain was obtained from the Biotechnology Center of the National Institute of Technology and Evaluation, cultured according to the attached instructions, and then genomic DNA extraction was performed. Using a genomic DNA of the NBRC14164 strain as a template, and using a combination of DNAs of base sequences represented by GEP2550 (SEQ ID NO: 84) and GEP2551 (SEQ ID NO: 85), PCR products were obtained by the PCR method, agarose gel electrophoresis was performed thereon, and then extraction and purification were performed. This is a DNA fragment containing a mdIC gene (Pp_mdIC) of the *Pseudomonas putida* NBRC14164 strain. In addition, pET-15b (manufactured by Novagen) was treated with NdeI, agarose gel electrophoresis was performed thereon, and then extraction and purification were performed. These two DNA fragments were mixed, and a plasmid pGE1161 in which Pp_mdIC was cloned into pET-15b was obtained by the same operation as in the creation of pGE1031.

Using pGE1161 as a template, and using a combination of DNAs of base sequences represented by GEP2653 (SEQ ID NO: 86) and GEP2654 (SEQ ID NO: 87), PCR products were obtained by the PCR method, agarose gel electrophoresis was performed thereon, and then extraction and purification were performed. In addition, pGE409 was treated with NdeI, agarose gel electrophoresis was performed thereon, and then extraction and purification were performed. These two DNA fragments were mixed, and a plasmid pGE1197 in which Pp_mdIC was subcloned into pGE409 was obtained by the same operation as in the creation of pGE1185.

2-3-(4) Construction of Kp_dhaT Overexpression Plasmid

A plasmid pHA12-dhaBT containing a gene derived from *Klebsiella pneumoniae* (DDBJ accession number: LC419022) was provided by Dr. Takahisa Tajima from Hiroshima University. Using this as a template, and using a combination of DNAs of base sequences represented by GEP2529 (SEQ ID NO: 88) and GEP2530 (SEQ ID NO: 89), PCR products were obtained by the PCR method, agarose gel electrophoresis was performed thereon, and then extraction and purification were performed. This is a DNA fragment containing a dhaT gene (Kp_dhaT) of *Klebsiella pneumoniae*. In addition, pET-15b (manufactured by Novagen) was treated with NdeI, agarose gel electrophoresis was performed thereon, and then extraction and purification were performed. These two DNA fragments were mixed, and a plasmid pGE1150 in which Kp_dhaT was cloned into pET-15b was obtained by the same operation as in the creation of pGE1161.

pGE1150 was treated with NdeI and BamHI, a 1.2 kb DNA fragment was subjected to agarose gel electrophoresis, and then extracted and purified. In addition, pGE945-2 was treated with NdeI and BamHI, agarose gel electrophoresis was performed thereon, and then extraction and purification were performed. These two DNA fragments were mixed, and a binding reaction of the DNA fragments was performed using a Ligation high Ver. 2 (manufactured by TOYOBO CO., LTD.) according to the attached instructions. Using the reaction products, *E. coli* DH5α Competent Cells (manufactured by Takara Bio Inc.) were transformed according to the attached instructions. A target transformant was selected by culturing on an LB agar medium containing 100 μg/ml of spectinomycin. This transformant was cultured in an LB medium containing 100 μg/ml of spectinomycin, and plasmid extraction was performed using the obtained culture suspension. In this manner, a plasmid pGE1190 in which Kp_dhaT was subcloned into pGE945-2 was obtained.

3. Bacterial Cell Construction

(3-1) Creation of Strain into which Pp_mdIC and Kp_dhaT Overexpression Plasmid is Introduced GES1070 was transformed by electroporation using pGE1197 and pGE1190, and a kanamycin/spectinomycin-resistant strain was selected on an A agar medium containing 25 μg/ml of kanamycin and 100 μg/ml of spectinomycin at 33° C. This was named GES1206.

GES1063 was transformed by electroporation using pGE1197 and pGE1190, and a kanamycin/spectinomycin-resistant strain was selected on an A agar medium containing 25 μg/ml of kanamycin and 100 μg/ml of spectinomycin at 33° C. This was named GES1077.

GES1064 was transformed by electroporation using pGE1197 and pGE1190, and a kanamycin/spectinomycin-resistant strain was selected on an A agar medium containing 25 μg/ml of kanamycin and 100 μg/ml of spectinomycin at 33° C. This was named GES1068.

GES1242 was transformed by electroporation using pGE1197 and pGE1190, and a kanamycin/spectinomycin-resistant strain was selected on an A agar medium containing 25 μg/ml of kanamycin and 100 μg/ml of spectinomycin at 33° C. This was named GES1282.

*Corynebacterium glutamicum* GES1068 was deposited in NITE Patent Microorganisms Depositary, NPMD (2-5-8 Kazusakamatari, Kisarazu City, Chiba, Japan (postal code: 292-0818)) (Deposit Date: Sep. 13, 2018, Accession Number: NITE BP-02780). GES1223 was transformed by electroporation using pGE1197 and pGE1190, and a kanamycin/spectinomycin-resistant strain was selected on an A agar medium containing 25 μg/ml of kanamycin and 100 μg/ml of spectinomycin at 33° C. This was named GES1253.

GES1233 was transformed by electroporation using pGE1197 and pGE1190, and a kanamycin/spectinomycin-resistant strain was selected on an A agar medium containing 25 μg/ml of kanamycin and 100 μg/ml of spectinomycin at 33° C. This was named GES1254.

*Corynebacterium glutamicum* GES1254 was deposited in NITE Patent Microorganisms Depositary, NPMD (2-5-8 Kazusakamatari, Kisarazu City, Chiba, Japan (postal code: 292-0818)) (Deposit Date: Sep. 13, 2018, Accession Number: NITE BP-02781).

4. Material Production Experiment

(4-1) Production of 4-hydroxy-2-oxobutyric Acid (HOB)

4-1-(1) Culture of GES1077

A glycerol stock of GES1077 was inoculated under aseptic conditions into an A agar medium containing 25 μg/ml of kanamycin and 100 μg/ml of spectinomycin, and cultured at 33° C. Bacterial cells grown on the agar medium were inoculated into 10 mL of a BA medium containing 25 μg/ml of kanamycin and 100 µg/ml of spectinomycin and shaking-cultured at 33° C., and thereby a seed culture solution was obtained. This seed culture was inoculated into 500 mL of a BA medium containing 25 µg/ml of kanamycin and 100 µg/ml of spectinomycin prepared in a 2 L flask so that a turbidity was 0.1. The mixture was shaken at 33° C. and cultured overnight. This main culture solution was centrifuged at 4° C. and 5500×g for 15 minutes, and the supernatant was removed. The wet bacterial cells thus obtained were used for the following reaction.

4-1-(2) Production of HOB Using GES1077

The wet bacterial cells prepared as described above were suspended in BR buffer so that a concentration thereof became 10% (w/v). A 50% (w/v) aqueous glucose solution and a 1.2 M aqueous formaldehyde solution were added to this bacterial cell suspension so that their concentrations respectively became 50 mM and 40 mM, and cultured at 33° C. while adjusting a pH to 6.0 using a 1.0 M aqueous potassium hydroxide solution. In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction solution was analyzed by liquid chromatography for organic acid analysis after 3 hours, 0.65 mM of HOB was produced.

4-1-(3) Comparative Example 1

The wet bacterial cells prepared as described above were suspended in BR buffer so that a concentration thereof became 10% (w/v). A 50% (w/v) aqueous glucose solution was added to this bacterial cell suspension so that its concentration became 50 mM, and cultured at 33° C. while adjusting a pH to 6.0 using a 1.0 M aqueous potassium hydroxide solution. When the supernatant of the reaction suspension was analyzed by liquid chromatography for organic acid analysis after 3 hours, HOB was not detected.

4-1-(4) Comparative Example 2

For GES1206, the same experiment as in 4-1-(1) and 4-1-(2) was performed. When the supernatant of the reaction suspension was analyzed by liquid chromatography for organic acid analysis 3 hours after the reaction, HOB was not detected.

Based on the results of 4-1-(2), 4-1-(3), and 4-1-(4), it was found that when bacterial cells having a gene encoding a class II aldolase such as GES1077 are cultured in the presence of saccharides and aldehydes, pyruvic acid is generated from saccharides, and when the enzyme catalyzes the aldol reaction between this pyruvic acid and aldehydes, an aldol compound typified by HOB is generated.

4-1-(5) Culture of GES1282

Wet bacterial cells obtained by culturing a glycerol stock of GES1282 in the same manner as in 4-1-(1) were used in the following reaction.

4-1-(6) Production of HOB Using GES1282

The wet bacterial cells prepared as described above were cultured in the same manner as in 4-1-(2). In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction solution was analyzed by liquid chromatography for organic acid analysis after 3 hours, 0.36 mM of HOB was produced.

4-1-(7) Comparative Example 1

The wet bacterial cells prepared as described above were cultured in the same manner as in 4-1-(3). In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction suspension was analyzed by liquid chromatography for organic acid analysis after 3 hours, HOB was not detected.

Based on the results of 4-1-(6), 4-1-(7), and 4-1-(4), it was found that when bacterial cells having a gene encoding a class II aldolase such as GES1282 which is different from GES1077 are cultured in the presence of saccharides and aldehydes, pyruvic acid is also generated from saccharides, and when the enzyme catalyzes the aldol reaction between this pyruvic acid and aldehydes, an aldol compound typified by HOB is generated.

4-1-(8) Culture of GES1253

Wet bacterial cells obtained by culturing a glycerol stock of GES1253 in the same manner as in 4-1-(1) were used in the following reaction.

4-1-(9) Production of HOB Using GES1253

The wet bacterial cells prepared as described above were cultured in the same manner as in 4-1-(2). In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction solution was analyzed by liquid chromatography for organic acid analysis after 3 hours, 0.34 mM of HOB was produced.

4-1-(10) Comparative Example 1

The wet bacterial cells prepared as described above were cultured in the same manner as in 4-1-(2). In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction suspension was analyzed by liquid chromatography for organic acid analysis after 3 hours, HOB was not detected.

Based on the results of 4-1-(9), 4-1-(10), and 4-1-(4), it was found that when bacterial cells having a gene encoding a class I aldolase such as GES1253 are cultured in the presence of saccharides and aldehydes, pyruvic acid is generated from saccharides, and when the enzyme catalyzes the aldol reaction between this pyruvic acid and aldehydes, an aldol compound typified by HOB is generated.

4-1-(11) Culture of GES1068 and GES1254

Wet bacterial cells obtained by culturing a glycerol stock of GES1068 and GES1254 in the same manner as in 4-1-(1) were used in the following reaction.

4-1-(12) Production of HOB Using GES1068 and GES1254

The wet bacterial cells prepared as described above were cultured in the same manner as in 4-1-(2). In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction solution was analyzed by liquid chromatography for organic acid analysis after 3 hours, 1.2 mM of HOB was produced in the reaction using GES1068, and 0.42 mM of HOB was produced in the reaction using GES1254.

Based on the results of 4-1-(12), it was found that even when a microorganism having a genotype different from GES1077 and GES1253, such as GES1068 and GES1254, are cultured in the presence of saccharides and aldehydes, as long as it is a bacterial cell having a gene encoding a class II aldolase, pyruvic acid is also generated from saccharides, and when the enzyme catalyzes the aldol reaction between this pyruvic acid and aldehydes, an aldol compound typified by HOB is generated.

(4-2) Production of 1,3-propanediol (PDO)

4-2-(1) Culture of GES1077 and GES1068

A glycerol stock of GES1077 and GES1068 was inoculated under aseptic conditions into an A agar medium containing 25 µg/ml of kanamycin and 100 µg/ml of spectinomycin, and cultured at 33° C. Bacterial cells grown on the agar medium were inoculated into 10 mL of a BA medium containing 25 µg/ml of kanamycin and 100 µg/ml of spectinomycin and shaking-cultured at 33° C., and thereby a seed culture solution was obtained. This seed culture was inoculated into 500 mL of a BA medium containing 25 µg/ml of kanamycin and 100 µg/ml of spectinomycin prepared in a 2 L flask so that a turbidity was 0.1. The mixture was shaken at 33° C. and cultured overnight. This main culture solution was centrifuged at 4° C. and 5500×g for 15 minutes, and the supernatant was removed. The wet bacterial cells thus obtained were used for the following reaction.

4-2-(2) Production of PDO Using GES1077 and GES1068

The wet bacterial cells prepared as described above were suspended in BR buffer so that a concentration thereof became 10% (w/v). A 50% (w/v) aqueous glucose solution and a 1.2 M aqueous formaldehyde solution were added to this bacterial cell suspension so that their concentrations respectively became 50 mM and 40 mM, and cultured at 33° C. while adjusting a pH to 6.0 using a 1.0 M aqueous potassium hydroxide solution. In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction solution was analyzed by liquid chromatography for sugar analysis after 3 hours, 7.4 mM of PDO was produced in the reaction using GES1077, and 11.4 mM of PDO was produced in the reaction using GES1068.

Based on the above results, it was found that in a case where a bacterial cell, which has a gene encoding a class II aldolase such as GES1077 and GES1068 and which can produce HOB when being cultured in the presence of saccharides and formaldehydes, further has a gene encoding decarboxylase and alcohol dehydrogenase, HOB can be further converted to PDO, and thereby PDO can be manufactured.

4-2-(3) Culture of GES1282

Wet bacterial cells obtained by culturing a glycerol stock of GES1282 in the same manner as in 4-2-(1) were used in the following reaction.

4-2-(4) Production of PDO Using GES1282

The wet bacterial cells prepared as described above were cultured in the same manner as in 4-2-(2). In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction solution was analyzed by liquid chromatography for sugar analysis after 6 hours, 11.4 mM of PDO was produced.

Based on the above results, it was found that in a case where a bacterial cell, which has a gene encoding a class II aldolase different from GES1077 and GES1068, such as GES1282, and which can produce HOB when being cultured in the presence of saccharides and formaldehydes, further has a gene encoding decarboxylase and alcohol dehydrogenase, HOB can also be further converted to PDO, and thereby PDO can be manufactured.

4-2-(5) Culture of GES1253 and GES1254

Wet bacterial cells obtained by culturing a glycerol stock of GES1253 and GES1254 in the same manner as in 4-2-(1) were used in the following reaction.

4-2-(6) Production of PDO Using GES1253 and GES1254

The wet bacterial cells prepared as described above were cultured in the same manner as in 4-2-(2). In the culture, stirring was performed to efficiently mix the aqueous potassium hydroxide solution, and aeration was not performed. By this operation, anaerobic conditions or microaerobic conditions were achieved at the above-mentioned concentration of the wet bacterial cells. When the supernatant of the reaction solution was analyzed by liquid chromatography for sugar analysis after 6 hours, 4.1 mM of PDO was produced in the reaction using GES1253, and 5.8 mM of PDO was produced in the reaction using GES1254.

Based on the above results, it was found that in a case where a bacterial cell, which has a gene encoding a class I aldolase such as GES1253 and GES1254 and which can produce HOB when being cultured in the presence of saccharides and formaldehydes, further has a gene encoding decarboxylase and alcohol dehydrogenase, HOB can be further converted to PDO, and thereby PDO can be manufactured.

The invention claimed is:

1. A method for manufacturing 1,3-propanediol, comprising culturing, in the presence of a saccharide and formaldehyde to produce 1,3-propanediol, a microorganism including the following genes:
  (a) a first gene encoding an enzyme having EC numbers selected from the group consisting of EC NO: 4.1.3.39, EC NO: 4.1.2.14, EC NO: 4.1.2.55, EC NO: 4.1.3.16, EC NO: 4.1.3.42, EC NO: 4.1.2.28, EC NO: 4.1.2.51, EC NO: 4.1.2.23, EC NO: 4.1.2.34, EC NO: 4.1.2.52, EC NO: 4.1.2.20, EC NO: 4.1.2.53, EC NO: 4.1.3.17 and EC NO: 4.1.3.43, that catalyzes an aldol reaction between pyruvic acid and formaldehyde;
  (b) a second gene encoding an enzyme having EC numbers selected from the group consisting of EEC NO: 4.1.1.7, EC NO: 4.1.1.1 and EC NO: 4.1.1.74 that catalyzes a decarboxylation reaction of 4-hydroxy-2-oxobutyric acid; and
  (c) a third gene encoding an enzyme having EC NO: 1.1.1.202 that catalyzes a reduction reaction of 3-hydroxypropionaldehyde.

2. The method for manufacturing 1,3-propanediol according to claim 1, wherein the culturing is performed under anaerobic conditions or microaerobic conditions.

3. The method for manufacturing 1,3-propanediol according to claim 1, wherein the culturing is performed in a state where the microorganism is suspended in a culture solution at a high density.

4. The method for manufacturing 1,3-propanediol according to claim 1, wherein the microorganism is an aerobic bacterium.

5. The method for manufacturing 1,3-propanediol according to claim 4, wherein the aerobic bacterium is a coryneform bacterium.

6. The method for manufacturing 1,3-propanediol according to claim 1,
  wherein the first gene is selected from the group consisting of:
  (1-1) a gene encoding a protein that consists of the amino acid sequence set forth in SEQ ID NO: 2 and catalyzes an aldol reaction between pyruvic acid and formaldehyde;
  (1-2) a gene encoding a protein that comprise at least 90% sequence identity to the amino acid sequence set forth in SEQ ID NO: 2 and catalyzes an aldol reaction between pyruvic acid and formaldehyde;
  (1-3) a gene encoding a protein that consists of the amino acid sequence set forth in SEQ ID NO: 4 and catalyzes an aldol reaction between pyruvic acid and formaldehyde;
  (1-4) a gene encoding a protein that comprise at least 90% sequence identity to the amino acid sequence set forth in SEQ ID NO: 4 and catalyzes an aldol reaction between pyruvic acid and formaldehyde;

(1-5) a gene encoding a protein that consists of the amino acid sequence set forth in SEQ ID NO: 6 and catalyzes an aldol reaction between pyruvic acid and formaldehyde; and
(1-6) a gene encoding a protein comprise at least 90% sequence identity to the amino acid sequence set forth in SEQ ID NO: 6 and catalyzes an aldol reaction between pyruvic acid and formaldehyde;
wherein the second gene is selected from the group consisting of:
(2-1) a gene encoding a protein that consists of the amino acid sequence set forth in SEQ ID NO: 8 and catalyzes a decarboxylation reaction of 4-hydroxy-2-oxobutyric acid; and
(2-2) a gene encoding a protein that comprise at least 90% sequence identity to the amino acid sequence set forth in SEQ ID NO: 8 and catalyzes a decarboxylation reaction of 4-hydroxy-2-oxobutyric acid, and
wherein the third gene is selected from the group consisting of:
(3-1) a gene encoding a protein that consists of the amino acid sequence set forth in SEQ ID NO: 10 and catalyzes a reduction reaction of 3-hydroxypropionaldehyde; and
(3-2) a gene encoding a protein comprise at least 90% sequence identity to the amino acid sequence set forth in SEQ ID NO: 10 and catalyzes a reduction reaction of 3-hydroxypropionaldehyde.

7. The method for manufacturing 1,3-propanediol according to claim 2, wherein the culturing is performed in a state where the microorganism is suspended in a culture solution at a high density.

8. The method for manufacturing 1,3-propanediol according to claim 2, wherein the microorganism is an aerobic bacterium.

9. The method for manufacturing 1,3-propanediol according to claim 3, wherein the microorganism is an aerobic bacterium.

10. The method for manufacturing 1,3-propanediol according to claim 2,
wherein the first gene is selected from the group consisting of:
(1-1) a gene encoding a protein that consists of the amino acid sequence set forth in SEQ ID NO: 2 and catalyzes an aldol reaction between pyruvic acid and formaldehyde;
(1-2) a gene encoding a protein that comprise at least 90% sequence identity to the amino acid sequence set forth in SEQ ID NO: 2 and catalyzes an aldol reaction between pyruvic acid and formaldehyde;
(1-3) a gene encoding a protein that consists of the amino acid sequence set forth in SEQ ID NO: 4 and catalyzes an aldol reaction between pyruvic acid and formaldehyde;
(1-4) a gene encoding a protein that comprise at least 90% sequence identity to the amino acid sequence set forth in SEQ ID NO: 4 and catalyzes an aldol reaction between pyruvic acid and formaldehyde;
(1-5) a gene encoding a protein that consists of the amino acid sequence set forth in SEQ ID NO: 6 and catalyzes an aldol reaction between pyruvic acid and formaldehyde; and
(1-6) a gene encoding a protein comprise at east 90% sequence identity to the amino acid sequence set forth in SEQ ID NO: 6 and catalyzes an aldol reaction between pyruvic acid and formaldehyde;
wherein the second gene is selected from the group consisting of:
(2-1) a gene encoding a protein that consists of the amino acid sequence set forth in SEQ ID NO: 8 and catalyzes a decarboxylation reaction of 4-hydroxy-2-oxobutyric acid; and
(2-2) a gene encoding a protein that comprise at least 90 sequence identity to the amino acid sequence set forth in SEQ ID NO: 8 and catalyzes a decarboxylation reaction of 4-hydroxy-2-oxobutyric acid, and
wherein the third gene is selected from the group consisting of:
(3-1) a gene encoding a protein that consists of the amino acid sequence set forth in SEQ ID NO: 10 and catalyzes a reduction reaction of 3-hydroxypropionaldehyde; and
(3-2) a gene encoding a protein comprise at least 90% sequence identity to the amino acid sequence set forth in SEQ ID NO: 10 and catalyzes a reduction reaction of 3-hydroxypropionaldehyde.

11. The method for manufacturing 1,3-propanediol according to claim 3,
wherein the first gene is selected from the group consisting of:
(1-1) a gene encoding a protein that consists of the amino acid sequence set forth in SEQ ID NO: 2 and catalyzes an aldol reaction between pyruvic acid and formaldehyde;
(1-2) a gene encoding a protein that comprise at least 90% sequence identity to the amino acid sequence set forth in SEQ ID NO: 2 and catalyzes an aldol reaction between pyruvic acid and formaldehyde;
(1-3) a gene encoding a protein that consists of the amino acid sequence set forth in SEQ ID NO: 4 and catalyzes an aldol reaction between pyruvic acid and formaldehyde;
(1-4) a gene encoding a protein that comprise at least 90% sequence identity to the amino acid sequence set forth in SEQ ID NO: 4 and catalyzes an aldol reaction between pyruvic acid and formaldehyde;
(1-5) a gene encoding a protein that consists of the amino acid sequence set forth in SEQ ID NO: 6 and catalyzes an aldol reaction between pyruvic acid and formaldehyde; and
(1-6) a gene encoding a protein comprise at least 90% sequence identity to the amino acid sequence set forth in SEQ ID NO: 6 and catalyzes an aldol reaction between pyruvic acid and formaldehyde;
wherein the second gene is selected from the group consisting of:
(2-1) a gene encoding a protein that consists of the amino acid sequence set forth in SEQ ID NO: 8 and catalyzes a decarboxylation reaction of 4-hydroxy-2-oxobutyric acid; and
(2-2) a gene encoding a protein that comprise at least 90% sequence identity to the amino acid sequence set forth in SEQ ID NO: 8 and catalyzes a decarboxylation reaction of 4-hydroxy-2-oxobutyric acid, and
wherein the third gene is selected from the group consisting of:
(3-1) a gene encoding a protein that consists of the amino acid sequence set forth in SEQ ID NO: 10 and catalyzes a reduction reaction of 3-hydroxypropionaldehyde; and
(3-2) a gene encoding a protein comprise at east 90% sequence identity to the amino acid sequence set forth in SEQ ID NO: 10 and catalyzes a reduction reaction of 3-hydroxypropionaldehyde.

12. The method for manufacturing 1,3-propanediol according to claim 4, wherein the first gene is selected from the group consisting of:

(1-1) a gene encoding a protein that consists of the amino acid sequence set forth in SEQ ID NO: 2 and catalyzes an aldol reaction between pyruvic acid and formaldehyde;

(1-2) a gene encoding a protein that comprise at least 90% sequence identity to the amino acid sequence set forth in SEQ ID NO: 2 and catalyzes an aldol reaction between pyruvic acid and formaldehyde;

(1-3) a gene encoding a protein that consists of the amino acid sequence set forth in SEQ ID NO: 4 and catalyzes an aldol reaction between pyruvic acid and formaldehyde;

(1-4) a gene encoding a protein that comprise at least 90% sequence identity to the amino acid sequence set forth in SEQ ID NO: 4 and catalyzes an aldol reaction between pyruvic acid and formaldehyde;

(1-5) a gene encoding a protein that consists of the amino acid sequence set forth in SEQ ID NO: 6 and catalyzes an aldol reaction between pyruvic acid and formaldehyde; and (1-6) a gene encoding a protein comprise at least 90% sequence identity to the amino acid sequence set forth in SEQ ID NO: 6 and catalyzes an aldol reaction between pyruvic acid and formaldehyde;

wherein the second gene is selected from the group consisting of:

(2-1) a gene encoding a protein that consists of the amino acid sequence set forth in SEQ ID NO: 8 and catalyzes a decarboxylation reaction of 4-hydroxy-2-oxobutyric acid; and (2-2) a gene encoding a protein that comprise at least 90% sequence identity to the amino acid sequence set forth in SEQ ID NO: 8 and catalyzes a decarboxylation reaction of 4-hydroxy-2-oxobutyric acid, and wherein the third gene is selected from the group consisting of:

(3-1) a gene encoding a protein that consists of the amino acid sequence set forth in SEQ ID NO: 10 and catalyzes a reduction reaction of 3-hydroxypropionaldehyde; and (3-2) a gene encoding a protein comprise at least 90% sequence identity to the amino acid sequence set forth in SEQ ID NO: 10 and catalyzes a reduction reaction of 3-hydroxypropionaldehyde.

13. The method for manufacturing 1,3-propanediol according to claim 5, wherein the first gene is selected from the group consisting of:

(1-1) a gene encoding a protein that consists of the amino acid sequence set forth in SEQ ID NO: 2 and catalyzes an aldol reaction between pyruvic acid and formaldehyde;

(1-2) a gene encoding a protein that comprise at least 90% sequence identity to the amino acid sequence set forth in SEQ ID NO: 2 and catalyzes an aldol reaction between pyruvic acid and formaldehyde;

(1-3) a gene encoding a protein that consists of the amino acid sequence set forth in SEQ ID NO: 4 and catalyzes an aldol reaction between pyruvic acid and formaldehyde;

(1-4) a gene encoding a protein that comprise at les 90% sequence identity to the amino acid sequence set forth in SEQ ID NO: 4 and catalyzes an aldol reaction between pyruvic acid and formaldehyde;

(1-5) a gene encoding a protein that consists of the amino acid sequence set forth in SEQ ID NO: 6 and catalyzes an aldol reaction between pyruvic acid and formaldehyde; and (1-6) a gene encoding a protein comprise at least 90% sequence identity to the amino acid sequence set forth in SEQ ID NO: 6 and catalyzes an aldol reaction between pyruvic acid and formaldehyde;

wherein the second gene is selected from the group consisting of:

(2-1) a gene encoding a protein that consists of the amino acid sequence set forth in SEQ ID NO: 8 and catalyzes a decarboxylation reaction of 4-hydroxy-2-oxobutyric acid; and (2-2) a gene encoding a protein that comprise at least 90% sequence identity to the amino acid sequence set forth in SEQ ID NO: 8 and catalyzes a decarboxylation reaction of 4-hydroxy-2-oxobutyric acid, and wherein the third gene is selected from the group consisting of:

(3-1) a gene encoding a protein that consists of the amino acid sequence set forth in SEQ ID NO: 10 and catalyzes a reduction reaction of 3-hydroxypropionaldehyde; and (3-2) a gene encoding a protein comprise at least 90% sequence identity to the amino acid sequence set forth in SEQ ID NO: 10 and catalyzes a reduction reaction of 3-hydroxypropionaldehyde.

14. The method for manufacturing 1,3-propanediol according to claim 1, wherein the microorganism is a bacterium.

15. The method for manufacturing 1,3-propanediol according to claim 1, wherein the microorganism is one selected from the group consisting of coryneform bacteria, *Escherichia coli*, and *Vibrio natriegens*.

* * * * *

SEQUENCE LISTING

<160> NUMBER OF SEQ ID NOS: 89

<210> SEQ ID NO 1
<211> LENGTH: 789
<212> TYPE: DNA
<213> ORGANISM: Escherichia coli

<400> SEQUENCE: 1

| | | |
|---|---|---|
| atggaaaaca gttttaaagc ggcgctgaaa gcaggccgtc cgcagattgg attatggctg | 60 |
| gggctgagca gcagctacag cgcggagtta ctggccggag caggattcga ctggttgttg | 120 |
| atcgacggtg agcacgcacc gaacaacgta caaaccgtgc tcacccagct acaggcgatt | 180 |
| gcgccctatc ccagccagcc ggtagtacgt ccgtcgtgga acgatccggt gcaaatcaaa | 240 |
| caactgctgg acgtcggcac acaaacctta ctggtgccga tggtacaaaa cgccgacgaa | 300 |
| gcccgtgaag cggtacgcgc cacccgttat ccccccgccg gtattcgcgg tgtgggcagt | 360 |
| gcgctggctc gcgcctcgcg ctggaatcgc attcctgatt acctgcaaaa agccaacgat | 420 |
| caaatgtgcg tgctggtgca gatcgaaacg cgtgaggcaa tgaagaactt accgcagatt | 480 |
| ctggacgtga aggcgtcga cggcgtgttt atcggcccgg cggatctgag cgccgatatg | 540 |
| ggttatgccg gtaatccgca gcacccggaa gtacaggccg ccattgagca ggcgatcgtg | 600 |
| cagatccgcg aagcgggcaa agcgccgggg atcctgatcg ccaatgagct actggcaaaa | 660 |
| cgctatctgg aactgggcgc gctgtttgtc gccgtcggcg ttgacaccac cctgctcgcc | 720 |
| cgcgccgccg aagcgctggc agcacggttt ggcgcgcagg ctacagcgat taagcccggc | 780 |
| gtgtattaa | 789 |

<210> SEQ ID NO 2
<211> LENGTH: 262
<212> TYPE: PRT
<213> ORGANISM: Escherichia coli

<400> SEQUENCE: 2

Met Glu Asn Ser Phe Lys Ala Ala Leu Lys Ala Gly Arg Pro Gln Ile
1               5                   10                  15

Gly Leu Trp Leu Gly Leu Ser Ser Ser Tyr Ser Ala Glu Leu Leu Ala
            20                  25                  30

Gly Ala Gly Phe Asp Trp Leu Leu Ile Asp Gly Glu His Ala Pro Asn
        35                  40                  45

Asn Val Gln Thr Val Leu Thr Gln Leu Gln Ala Ile Ala Pro Tyr Pro
    50                  55                  60

Ser Gln Pro Val Val Arg Pro Ser Trp Asn Asp Pro Val Gln Ile Lys
65                  70                  75                  80

Gln Leu Leu Asp Val Gly Thr Gln Thr Leu Leu Val Pro Met Val Gln
                85                  90                  95

Asn Ala Asp Glu Ala Arg Glu Ala Val Arg Ala Thr Arg Tyr Pro Pro
            100                 105                 110

Ala Gly Ile Arg Gly Val Gly Ser Ala Leu Ala Arg Ala Ser Arg Trp
        115                 120                 125

Asn Arg Ile Pro Asp Tyr Leu Gln Lys Ala Asn Asp Gln Met Cys Val
    130                 135                 140

Leu Val Gln Ile Glu Thr Arg Glu Ala Met Lys Asn Leu Pro Gln Ile
145                 150                 155                 160

Leu Asp Val Glu Gly Val Asp Gly Val Phe Ile Gly Pro Ala Asp Leu
                165                 170                 175

Ser Ala Asp Met Gly Tyr Ala Gly Asn Pro Gln His Pro Glu Val Gln
            180                 185                 190

Ala Ala Ile Glu Gln Ala Ile Val Gln Ile Arg Glu Ala Gly Lys Ala
        195                 200                 205

Pro Gly Ile Leu Ile Ala Asn Glu Leu Leu Ala Lys Arg Tyr Leu Glu
        210                 215                 220

Leu Gly Ala Leu Phe Val Ala Val Gly Val Asp Thr Thr Leu Leu Ala
225                 230                 235                 240

Arg Ala Ala Glu Ala Leu Ala Ala Arg Phe Gly Ala Gln Ala Thr Ala
                245                 250                 255

Ile Lys Pro Gly Val Tyr
            260

<210> SEQ ID NO 3
<211> LENGTH: 804
<212> TYPE: DNA
<213> ORGANISM: Escherichia coli

<400> SEQUENCE: 3
atgaacgcat tattaagcaa tcccttaaa gaacgtttac gcaagggcga agtgcaaatt      60
ggtctgtggt taagctcaac gactgcctat atggcagaaa ttgccgccac ttctggttat    120
gactggttgc tgattgacgg ggagcacgcg ccaaacacca ttcaggatct ttatcatcag    180
ctacaggcgg tagcgcccta tgccagccaa cccgtgatcc gtccggtgga aggcagtaaa    240
ccgctgatta aacaagtcct ggatattggc gcgcaaactc tactgatccc gatggtcgat    300
actgccgaac aggcacgtca ggtggtgtct gccacgcgct atcctcccta cggtgagcgt    360
ggtgtcgggg ccagtgtggc acgggctgcg cgctggggac gcattgagaa ttacatggcg    420
caagttaacg attcgctttg tctgttggtg caggtggaaa gtaaaacggc actggataac    480
ctggacgaaa tcctcgacgt cgaagggatt gatggcgtgt tattggacc tgcggatctt     540
tctgcgtcgt gggctacccc ggataacgcc gggcacccgg aagtgcagcg aattattgaa    600
accagtattc ggcggatccg tgctgcgggt aaagcggctg gttttctggc tgtggctcct    660
gatatggcgc agcaatgcct ggcgtgggga gcgaactttg tcgctgttgg cgttgacacg    720
atgctctaca gcgatgccct ggatcaacga ctggcgatgt taaatcagg caaaaatggg     780
ccacgcataa aagtagtta ttaa                                            804

<210> SEQ ID NO 4
<211> LENGTH: 267
<212> TYPE: PRT
<213> ORGANISM: Escherichia coli

<400> SEQUENCE: 4

Met Asn Ala Leu Leu Ser Asn Pro Phe Lys Glu Arg Leu Arg Lys Gly
1               5                   10                  15

Glu Val Gln Ile Gly Leu Trp Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
    50                  55                  60

Ala Pro Tyr Ala Ser Gln Pro Val Ile Arg Pro Val Glu Gly Ser Lys
65                  70                  75                  80

Pro Leu Ile Lys Gln Val Leu Asp Ile Gly Ala Gln Thr Leu Leu Ile
                85                  90                  95

```
Pro Met Val Asp Thr Ala Glu Gln Ala Arg Gln Val Val Ser Ala Thr
            100                 105                 110

Arg Tyr Pro Pro Tyr Gly Glu Arg Gly Val Gly Ala Ser Val Ala Arg
        115                 120                 125

Ala Ala Arg Trp Gly Arg Ile Glu Asn Tyr Met Ala Gln Val Asn Asp
    130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
                165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
        195                 200                 205

Ala Gly Lys Ala Ala Gly Phe Leu Ala Val Ala Pro Asp Met Ala Gln
    210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
                245                 250                 255

Gly Lys Asn Gly Pro Arg Ile Lys Gly Ser Tyr
            260                 265

<210> SEQ ID NO 5
<211> LENGTH: 894
<212> TYPE: DNA
<213> ORGANISM: Escherichia coli

<400> SEQUENCE: 5
atggcaacga atttacgtgg cgtaatggct gcactcctga ctccttttga ccaacaacaa      60
gcactggata aagcgagtct gcgtcgcctg gttcagttca atattcagca gggcatcgac     120
ggtttatacg tgggtggttc gaccggcgag gcctttgtac aaagcctttc gagcgtgaa     180 caggtactgg aaatcgtcgc cgaagaggcg aaaggtaaga ttaaactcat cgcccacgtc     240
ggttgcgtca gcaccgccga agccaacaa cttgcggcat cggctaaacg ttatggcttc     300
gatgccgtct ccgccgtcac gccgttctac tatccttttca gctttgaaga cactgcgat     360 cactatcggg caattattga ttcggcggat ggtttgccga tggtggtgta caacattcca     420
gccctgagtg gggtaaaaact gaccctggat cagatcaaca cacttgttac attgcctggc     480
gtaggtgcgc tgaaacagac ctctggcgat ctctatcaga tggagcagat ccgtcgtgaa     540
catcctgatc ttgtgctcta taacggttac gacgaaatct tcgcctctgg tctgctggcg     600
ggcgctgatg gtggtatcgg cagtacctac aacatcatgg gctggcgcta tcaggggatc     660
gttaaggcgc tgaaagaagg cgatatccag accgcgcaga aactgcaaac tgaatgcaat     720
aaagtcattg atttactgat caaaacgggc gtattccgcg gcctgaaaac tgtcctccat     780
tatatggatg tcgtttctgt gccgctgtgc cgcaaaccgt ttggaccggt agatgaaaaa     840
tatctgccag aactgaaggc gctggcccag cagttgatgc aagagcgcgg gtaa           894

<210> SEQ ID NO 6
<211> LENGTH: 297
<212> TYPE: PRT
<213> ORGANISM: Escherichia coli

<400> SEQUENCE: 6
```

```
Met Ala Thr Asn Leu Arg Gly Val Met Ala Ala Leu Leu Thr Pro Phe
1               5                   10                  15

Asp Gln Gln Gln Ala Leu Asp Lys Ala Ser Leu Arg Arg Leu Val Gln
            20                  25                  30

Phe Asn Ile Gln Gln Gly Ile Asp Gly Leu Tyr Val Gly Gly Ser Thr
        35                  40                  45

Gly Glu Ala Phe Val Gln Ser Leu Ser Glu Arg Glu Gln Val Leu Glu
50                  55                  60

Ile Val Ala Glu Glu Ala Lys Gly Lys Ile Lys Leu Ile Ala His Val
65                  70                  75                  80

Gly Cys Val Ser Thr Ala Glu Ser Gln Gln Leu Ala Ala Ser Ala Lys
                85                  90                  95

Arg Tyr Gly Phe Asp Ala Val Ser Ala Val Thr Pro Phe Tyr Tyr Pro
            100                 105                 110

Phe Ser Phe Glu Glu His Cys Asp His Tyr Arg Ala Ile Ile Asp Ser
        115                 120                 125

Ala Asp Gly Leu Pro Met Val Val Tyr Asn Ile Pro Ala Leu Ser Gly
130                 135                 140

Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
            180                 185                 190

Ile Phe Ala Ser Gly Leu Leu Ala Gly Ala Asp Gly Ile Gly Ser
        195                 200                 205

Thr Tyr Asn Ile Met Gly Trp Arg Tyr Gln Gly Ile Val Lys Ala Leu
210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
            260                 265                 270

Pro Phe Gly Pro Val Asp Glu Lys Tyr Leu Pro Glu Leu Lys Ala Leu
        275                 280                 285

Ala Gln Gln Leu Met Gln Glu Arg Gly
290                 295
```

<210> SEQ ID NO 7
<211> LENGTH: 1587
<212> TYPE: DNA
<213> ORGANISM: Pseudomonas putida

<400> SEQUENCE: 7

```
atggcttcgg tacacggcac acatacgaa  ctcttgcgac gtcaaggcat cgatacggtc    60
ttcggcaatc ctggctcgaa cgagctcccg tttttgaagg actttccaga ggactttcga   120
tacatcctgg ctttgcagga agcgtgtgtg gtgggcattg cagacggcta tgcgcaagcc   180
agtcggaagc cggctttcat taacctgcat tctgctgctg gtaccggcaa tgctatgggt   240
gcactcagta acgcctggaa ctcacattcc ccgctgatcg tcactgccgg ccagcagacc   300
agggcgatga ttgcgttgga agctctgctg accaacgtcg atgccgccaa cctgccacga   360
ccacttgtca aatggagcta cgagcccgca agcgcagcag aagtccctca tgcgatgagc   420
```

-continued

```
agggctatcc atatggcaag catggcgcca caaggccctg tctatctttc ggtgccatat    480
gacgattggg ataaggatgc tgatcctcag tcccaccacc tttttgatcg ccatgtcagt    540
tcatcagtac gcctgaacga ccaggatctc gatattctgg tgaaagctct caacagcgca    600
tccaacccgg cgatcgtcct gggcccggac gtcgacgcag caaatgcgaa cgcagactgc    660
gtcatgttgg ccgaacgcct caaagctccg gtttggggttg cgccatccgc tccacgctgc    720
ccattcccta cccgtcatcc ttgcttccgt ggattgatgc cagctggcat cgcagcgatt    780
tctcagctgc tcgaaggtca cgatgtggtt ttggtaatcg gcgctccagt gttccgttac    840
caccaatacg acccaggtca atatctcaaa cctggcacgc gattgatttc ggtgacctgc    900
gacccgctcg aagctgcacg cgcgccaatg ggcgatgcga tcgtggcaga cattggtgcg    960
atggctagcg ctcttgccaa cttggttgaa gagagcagcc gccagctccc aactgcagct   1020
ccggaacccg cgaaggttga ccaagacgct ggccgacttc acccagagac agtgttcgac   1080
acactgaacg acatggcccc ggagaatgcg atttacctga cgagtcgac ttcaacgacc   1140
gcccaaatgt ggcagcgcct gaacatgcgc aaccctggta gctactactt ctgtgcagct   1200
ggcggactgg gcttcgccct gcctgcagca attggcgttc aactcgcaga acccgagcga   1260
caagtcatcg ccgtcattgg cgacggatcg gcgaactaca gcattagtgc gttgtggact   1320
gcagctcagt acaacatccc cactatcttc gtgatcatga acaacggcac ctacggtgcg   1380
ttgcgatggt ttgccggcgt tctcgaagca gaaaacgttc ctgggctgga tgtgccaggg   1440
atcgacttcc gcgcactcgc caagggctat ggtgtccaag cgctgaaagc cgacaacctt   1500
gagcagctca agggttcgct acaagaagcg ctttctgcca aaggcccggt acttatcgaa   1560
gtaagcaccg taagcccggt gaagtga                                      1587
```

<210> SEQ ID NO 8
<211> LENGTH: 528
<212> TYPE: PRT
<213> ORGANISM: Pseudomonas putida

<400> SEQUENCE: 8

```
Met Ala Ser Val His Gly Thr Thr Tyr Glu Leu Leu Arg Arg Gln Gly
1               5                   10                  15

Ile Asp Thr Val Phe Gly Asn Pro Gly Ser Asn Glu Leu Pro Phe Leu
            20                  25                  30

Lys Asp Phe Pro Glu Asp Phe Arg Tyr Ile Leu Ala Leu Gln Glu Ala
        35                  40                  45

Cys Val Val Gly Ile Ala Asp Gly Tyr Ala Gln Ala Ser Arg Lys Pro
    50                  55                  60

Ala Phe Ile Asn Leu His Ser Ala Ala Gly Thr Gly Asn Ala Met Gly
65                  70                  75                  80

Ala Leu Ser Asn Ala Trp Asn Ser His Ser Pro Leu Ile Val Thr Ala
                85                  90                  95

Gly Gln Gln Thr Arg Ala Met Ile Gly Val Glu Ala Leu Leu Thr Asn
            100                 105                 110

Val Asp Ala Ala Asn Leu Pro Arg Pro Leu Val Lys Trp Ser Tyr Glu
        115                 120                 125

Pro Ala Ser Ala Ala Glu Val Pro His Ala Met Ser Arg Ala Ile His
    130                 135                 140

Met Ala Ser Met Ala Pro Gln Gly Pro Val Tyr Leu Ser Val Pro Tyr
145                 150                 155                 160
```

```
Asp Asp Trp Asp Lys Asp Ala Asp Pro Gln Ser His His Leu Phe Asp
                 165                 170                 175

Arg His Val Ser Ser Val Arg Leu Asn Gln Asp Leu Asp Ile
            180                 185                 190

Leu Val Lys Ala Leu Asn Ser Ala Ser Asn Pro Ala Ile Val Leu Gly
            195                 200                 205

Pro Asp Val Asp Ala Ala Asn Ala Asn Ala Asp Cys Val Met Leu Ala
210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Val Val Leu Val
                260                 265                 270

Ile Gly Ala Pro Val Phe Arg Tyr His Gln Tyr Asp Pro Gly Gln Tyr
            275                 280                 285

Leu Lys Pro Gly Thr Arg Leu Ile Ser Val Thr Cys Asp Pro Leu Glu
    290                 295                 300

Ala Ala Arg Ala Pro Met Gly Asp Ala Ile Val Ala Asp Ile Gly Ala
305                 310                 315                 320

Met Ala Ser Ala Leu Ala Asn Leu Val Glu Glu Ser Ser Arg Gln Leu
                325                 330                 335

Pro Thr Ala Ala Pro Glu Pro Ala Lys Val Asp Gln Asp Ala Gly Arg
                340                 345                 350

Leu His Pro Glu Thr Val Phe Asp Thr Leu Asn Asp Met Ala Pro Glu
            355                 360                 365

Asn Ala Ile Tyr Leu Asn Glu Ser Thr Ser Thr Thr Ala Gln Met Trp
370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Glu Arg Gln Val Ile Ala Val Ile Gly Asp Gly Ser Ala Asn
            420                 425                 430

Tyr Ser Ile Ser Ala Leu Trp Thr Ala Ala Gln Tyr Asn Ile Pro Thr
    435                 440                 445

Ile Phe Val Ile Met Asn Asn Gly Thr Tyr Gly Ala Leu Arg Trp Phe
450                 455                 460

Ala Gly Val Leu Glu Ala Glu Asn Val Pro Gly Leu Asp Val Pro Gly
465                 470                 475                 480

Ile Asp Phe Arg Ala Leu Ala Lys Gly Tyr Gly Val Gln Ala Leu Lys
                485                 490                 495

Ala Asp Asn Leu Glu Gln Leu Lys Gly Ser Leu Gln Glu Ala Leu Ser
            500                 505                 510

Ala Lys Gly Pro Val Leu Ile Glu Val Ser Thr Val Ser Pro Val Lys
    515                 520                 525

<210> SEQ ID NO 9
<211> LENGTH: 1164
<212> TYPE: DNA
<213> ORGANISM: Klebsiella pneumoniae

<400> SEQUENCE: 9
atgagctatc gtatgttcga ttatctggtg ccaaacgtta actttttttgg ccccaacgcc    60
```

```
atttccgtag tcggcgaacg ctgccagctg ctggggggga aaaaagccct gctggtcacc    120
gacaaaggcc tgcgggcaat taaagatggc gcggtggaca aaaccctgca ttatctgcgg    180
gaggccggga tcgaggtggc gatctttgac ggcgtcgagc cgaacccgaa agacaccaac    240
gtgcgcgacg gcctcgctgt gtttcgccgc gaacagtgcg acatcatcgt caccgtgggc    300
ggcggcagcc cgcacgattg cggcaaaggc atcggcatcg ccgccaccca tgagggcgat    360
ctgtaccagt atgccggaat cgagaccctg accaacccgc tgccgcctat cgtcgcggtc    420
aataccaccg ccggcaccgc cagcgaggtc acccgccact gcgtcctgac caacaccgaa    480
accaaagtga agtttgtgat cgtcagctgg cgcaacctgc cgtcggtctc tatcaacgat    540
ccactgctga tgatcggtaa accggccgcc ctgaccgcgg cgaccgggat ggatgccctg    600
acccacgccg tagaggccta tatctccaaa gacgctaacc cggtgacgga cgccgccgcc    660
atgcaggcga tccgcctcat cgcccgcaac ctgcgccagg ccgtggccct cggcagcaat    720
ctgcaggcgc gggaaaacat ggcctatgcc tctctgctgg ccgggatggc tttcaataac    780
gccaacctcg gctacgtgca cgccatggca caccagctgg gcggcctgta cgacatgccg    840
cacggcgtgg ccaacgctgt cctgctgccg catgtggcgc gctacaacct gatcgccaac    900
ccggagaaat cgccgatat tgctgaactg atgggcgaaa atatcaccgg actgtccact    960
ctcgacgcgg cggaaaaagc catcgccgct atcacgcgtc tgtcgatgga tatcggtatt   1020
ccgcagcatc tgcgcgatct gggagtaaaa gaggccgact tcccctacat ggcggagatg   1080
gctctgaaag acggcaatgc gttctcgaac ccgcgtaaag caacgagca ggagattgcc   1140 gcgatttttcc gccaggcatt ctaa                                         1164

<210> SEQ ID NO 10
<211> LENGTH: 387
<212> TYPE: PRT
<213> ORGANISM: Klebsiella pneumoniae

<400> SEQUENCE: 10

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175
```

```
Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Met Gln Ala Ile
210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
370                 375                 380

Gln Ala Phe
385

<210> SEQ ID NO 11
<211> LENGTH: 30
<212> TYPE: DNA
<213> ORGANISM: Artificial Sequence
<220> FEATURE:
<223> OTHER INFORMATION: Forward primer for sacB gene

<400> SEQUENCE: 11
ggggaagctt gacgtccaca tatacctgcc                                        30

<210> SEQ ID NO 12
<211> LENGTH: 24
<212> TYPE: DNA
<213> ORGANISM: Artificial Sequence
<220> FEATURE:
<223> OTHER INFORMATION: Reverse primer for sacB gene

<400> SEQUENCE: 12
attcggatcc gtatccacct ttac                                              24

<210> SEQ ID NO 13
<211> LENGTH: 26
<212> TYPE: DNA
<213> ORGANISM: Artificial Sequence
<220> FEATURE:
<223> OTHER INFORMATION: Forward primer for deleting KpnI recognition
      site on sacB gene

<400> SEQUENCE: 13
tgaacagata ccatttgccg ttcatt                                            26
```

<210> SEQ ID NO 14
<211> LENGTH: 26
<212> TYPE: DNA
<213> ORGANISM: Artificial Sequence
<220> FEATURE:
<223> OTHER INFORMATION: Reverse primer for deleting KpnI recognition
      site on sacB gene

<400> SEQUENCE: 14
aatggtatct gttcactgac tcccgc                                         26

<210> SEQ ID NO 15
<211> LENGTH: 35
<212> TYPE: DNA
<213> ORGANISM: Artificial Sequence
<220> FEATURE:
<223> OTHER INFORMATION: Up-Forward primer for ppc gene deletion

<400> SEQUENCE: 15
ccatgattac gaattcggga aacttttta agaaa                                35

<210> SEQ ID NO 16
<211> LENGTH: 20
<212> TYPE: DNA
<213> ORGANISM: Artificial Sequence
<220> FEATURE:
<223> OTHER INFORMATION: Up-Reverse primer for ppc gene deletion

<400> SEQUENCE: 16
taactacttt aaacactctt                                                20

<210> SEQ ID NO 17
<211> LENGTH: 35
<212> TYPE: DNA
<213> ORGANISM: Artificial Sequence
<220> FEATURE:
<223> OTHER INFORMATION: Down-Forward primer for ppc gene deletion

<400> SEQUENCE: 17
tgtttaaagt agttatccag ccggctgggt agtac                               35

<210> SEQ ID NO 18
<211> LENGTH: 35
<212> TYPE: DNA
<213> ORGANISM: Artificial Sequence
<220> FEATURE:
<223> OTHER INFORMATION: Down-Reverse primer for ppc gene deletion

<400> SEQUENCE: 18
taccgagctc gaattgaagt attcaagggg atttc                               35

<210> SEQ ID NO 19
<211> LENGTH: 35
<212> TYPE: DNA
<213> ORGANISM: Artificial Sequence
<220> FEATURE:
<223> OTHER INFORMATION: Up-Forward primer for ldhA gene deletion

<400> SEQUENCE: 19
gacggccagt gaattttca tacgaccacg ggcta                                35

<210> SEQ ID NO 20
<211> LENGTH: 20
<212> TYPE: DNA
<213> ORGANISM: Artificial Sequence
<220> FEATURE:

<223> OTHER INFORMATION: Up-Reverse primer for ldhA gene deletion

<400> SEQUENCE: 20
gacaatcttg ttaccgacgg                                              20

<210> SEQ ID NO 21
<211> LENGTH: 35
<212> TYPE: DNA
<213> ORGANISM: Artificial Sequence
<220> FEATURE:
<223> OTHER INFORMATION: Down-Forward primer for ldhA gene deletion

<400> SEQUENCE: 21
ggtaacaaga ttgtccattc cgcaaatacc ctgcg                             35

<210> SEQ ID NO 22
<211> LENGTH: 35
<212> TYPE: DNA
<213> ORGANISM: Artificial Sequence
<220> FEATURE:
<223> OTHER INFORMATION: Down-Reverse primer for ldhA gene deletion

<400> SEQUENCE: 22
taccgagctc gaattgggac gttgatgacg ctgcc                             35

<210> SEQ ID NO 23
<211> LENGTH: 35
<212> TYPE: DNA
<213> ORGANISM: Artificial Sequence
<220> FEATURE:
<223> OTHER INFORMATION: Up-Forward primer for pyc gene deletion

<400> SEQUENCE: 23
gacggccagt gaattgttga tgactgttgg ttcca                             35

<210> SEQ ID NO 24
<211> LENGTH: 26
<212> TYPE: DNA
<213> ORGANISM: Artificial Sequence
<220> FEATURE:
<223> OTHER INFORMATION: Up-Reverse primer for pyc gene deletion

<400> SEQUENCE: 24
ctcgagtaga gtaattattc ctttca                                       26

<210> SEQ ID NO 25
<211> LENGTH: 35
<212> TYPE: DNA
<213> ORGANISM: Artificial Sequence
<220> FEATURE:
<223> OTHER INFORMATION: Down-Forward primer for pyc gene deletion

<400> SEQUENCE: 25
attactctac tcgagacctt tctgtaaaaa gcccc                             35

<210> SEQ ID NO 26
<211> LENGTH: 35
<212> TYPE: DNA
<213> ORGANISM: Artificial Sequence
<220> FEATURE:
<223> OTHER INFORMATION: Down-Reverse primer for pyc gene deletion

<400> SEQUENCE: 26
taccgagctc gaattcacga tccgccgggc agcct                             35

```
<210> SEQ ID NO 27
<211> LENGTH: 33
<212> TYPE: DNA
<213> ORGANISM: Artificial Sequence
<220> FEATURE:
<223> OTHER INFORMATION: Up-Forward primer for poxB gene deletion

<400> SEQUENCE: 27
gacggccagt gaaaacgtta atgaggaaaa ccg                            33

<210> SEQ ID NO 28
<211> LENGTH: 20
<212> TYPE: DNA
<213> ORGANISM: Artificial Sequence
<220> FEATURE:
<223> OTHER INFORMATION: Up-Reverse primer for poxB gene deletion

<400> SEQUENCE: 28
aattaattgt tctgcgtagc                                           20

<210> SEQ ID NO 29
<211> LENGTH: 41
<212> TYPE: DNA
<213> ORGANISM: Artificial Sequence
<220> FEATURE:
<223> OTHER INFORMATION: Down-Forward primer for poxB gene deletion

<400> SEQUENCE: 29
gcagaacaat taattctcga gtcgaacata aggaatattc c                   41

<210> SEQ ID NO 30
<211> LENGTH: 35
<212> TYPE: DNA
<213> ORGANISM: Artificial Sequence
<220> FEATURE:
<223> OTHER INFORMATION: Down-Reverse primer for poxB gene deletion

<400> SEQUENCE: 30
taccgagctc gaattttcca ggtacggaaa gtgcc                          35

<210> SEQ ID NO 31
<211> LENGTH: 35
<212> TYPE: DNA
<213> ORGANISM: Artificial Sequence
<220> FEATURE:
<223> OTHER INFORMATION: Up-Forward primer for alaA gene deletion

<400> SEQUENCE: 31
gacggccagt gaattttca ccgaagtgac accta                           35

<210> SEQ ID NO 32
<211> LENGTH: 26
<212> TYPE: DNA
<213> ORGANISM: Artificial Sequence
<220> FEATURE:
<223> OTHER INFORMATION: Up-Reverse primer for alaA gene deletion

<400> SEQUENCE: 32
ctcgagccgc tcaatgttgc cacttt                                    26

<210> SEQ ID NO 33
<211> LENGTH: 35
<212> TYPE: DNA
<213> ORGANISM: Artificial Sequence
<220> FEATURE:
<223> OTHER INFORMATION: Down-Forward primer for alaA gene deletion
```

<400> SEQUENCE: 33
attgagcggc tcgagtagtt gttaggattc accac          35

<210> SEQ ID NO 34
<211> LENGTH: 35
<212> TYPE: DNA
<213> ORGANISM: Artificial Sequence
<220> FEATURE:
<223> OTHER INFORMATION: Down-Reverse primer for alaA gene deletion

<400> SEQUENCE: 34
taccgagctc gaattgttcc ctggaaattg tttgc          35

<210> SEQ ID NO 35
<211> LENGTH: 35
<212> TYPE: DNA
<213> ORGANISM: Artificial Sequence
<220> FEATURE:
<223> OTHER INFORMATION: Up-Forward primer for ilvB gene deletion

<400> SEQUENCE: 35
gacggccagt gaattaccgc acgcgaccag ttatt          35

<210> SEQ ID NO 36
<211> LENGTH: 26
<212> TYPE: DNA
<213> ORGANISM: Artificial Sequence
<220> FEATURE:
<223> OTHER INFORMATION: Up-Reverse primer for ilvB gene deletion

<400> SEQUENCE: 36
gctagcgact ttctggctcc tttact          26

<210> SEQ ID NO 37
<211> LENGTH: 35
<212> TYPE: DNA
<213> ORGANISM: Artificial Sequence
<220> FEATURE:
<223> OTHER INFORMATION: Down-Forward primer for ilvB gene deletion

<400> SEQUENCE: 37
cagaaagtcg ctagcggaga gacccaagat ggcta          35

<210> SEQ ID NO 38
<211> LENGTH: 35
<212> TYPE: DNA
<213> ORGANISM: Artificial Sequence
<220> FEATURE:
<223> OTHER INFORMATION: Down-Reverse primer for ilvB gene deletion

<400> SEQUENCE: 38
taccgagctc gaattctcga tgtcgttggt gaaga          35

<210> SEQ ID NO 39
<211> LENGTH: 35
<212> TYPE: DNA
<213> ORGANISM: Artificial Sequence
<220> FEATURE:
<223> OTHER INFORMATION: Up-Forward primer for cg0931 gene deletion

<400> SEQUENCE: 39
gacggccagt gaattagcag ggacgaaagt cggga          35

<210> SEQ ID NO 40
<211> LENGTH: 26

<210> SEQ ID NO 40
<211> LENGTH: 26
<212> TYPE: DNA
<213> ORGANISM: Artificial Sequence
<220> FEATURE:
<223> OTHER INFORMATION: Up-Reverse primer for cg0931 gene deletion

<400> SEQUENCE: 40
ctcgaggcag ctactatatt tgatcc                                          26

<210> SEQ ID NO 41
<211> LENGTH: 35
<212> TYPE: DNA
<213> ORGANISM: Artificial Sequence
<220> FEATURE:
<223> OTHER INFORMATION: Down-Forward primer for cg0931 gene deletion

<400> SEQUENCE: 41
agtagctgcc tcgagtttga acaggttgtt ggggg                                35

<210> SEQ ID NO 42
<211> LENGTH: 35
<212> TYPE: DNA
<213> ORGANISM: Artificial Sequence
<220> FEATURE:
<223> OTHER INFORMATION: Down-Reverse primer for cg0931 gene deletion

<400> SEQUENCE: 42
taccgagctc gaattatcga cggcaaaacg cccaa                                35

<210> SEQ ID NO 43
<211> LENGTH: 35
<212> TYPE: DNA
<213> ORGANISM: Artificial Sequence
<220> FEATURE:
<223> OTHER INFORMATION: Up-Forward primer for adhE gene deletion

<400> SEQUENCE: 43
gtgaattcga gctcgcagaa gcagatcttg caatc                                35

<210> SEQ ID NO 44
<211> LENGTH: 32
<212> TYPE: DNA
<213> ORGANISM: Artificial Sequence
<220> FEATURE:
<223> OTHER INFORMATION: Up-Reverse primer for adhE gene deletion

<400> SEQUENCE: 44
cttcctcgag aattccaggc actacagtgc tc                                   32

<210> SEQ ID NO 45
<211> LENGTH: 32
<212> TYPE: DNA
<213> ORGANISM: Artificial Sequence
<220> FEATURE:
<223> OTHER INFORMATION: Down-Forward primer for adhE gene deletion

<400> SEQUENCE: 45
gaattctcga ggaagaggct ttcaacacca tg                                   32

<210> SEQ ID NO 46
<211> LENGTH: 35
<212> TYPE: DNA
<213> ORGANISM: Artificial Sequence
<220> FEATURE:
<223> OTHER INFORMATION: Down-Reverse primer for adhE gene deletion

<400> SEQUENCE: 46
aggtggatac ggatcggaac aaagtgtctc cagag        35

<210> SEQ ID NO 47
<211> LENGTH: 37
<212> TYPE: DNA
<213> ORGANISM: Artificial Sequence
<220> FEATURE:
<223> OTHER INFORMATION: Up-Forward primer for adhE gene deletion

<400> SEQUENCE: 47
gtgaattcga gctcgattca ggatttgctt cgcgacg        37

<210> SEQ ID NO 48
<211> LENGTH: 37
<212> TYPE: DNA
<213> ORGANISM: Artificial Sequence
<220> FEATURE:
<223> OTHER INFORMATION: Down-Reverse primer for adhE gene deletion

<400> SEQUENCE: 48
aggtggatac ggatcacagt gtccggatca tctgctg        37

<210> SEQ ID NO 49
<211> LENGTH: 35
<212> TYPE: DNA
<213> ORGANISM: Artificial Sequence
<220> FEATURE:
<223> OTHER INFORMATION: Up-Forward primer for ald gene deletion

<400> SEQUENCE: 49
gtgaattcga gctcgccgaa acctcaaaga atccc        35

<210> SEQ ID NO 50
<211> LENGTH: 32
<212> TYPE: DNA
<213> ORGANISM: Artificial Sequence
<220> FEATURE:
<223> OTHER INFORMATION: Up-Reverse primer for ald gene deletion

<400> SEQUENCE: 50
ggtactcgag tcctggattt gcgtagacag tc        32

<210> SEQ ID NO 51
<211> LENGTH: 32
<212> TYPE: DNA
<213> ORGANISM: Artificial Sequence
<220> FEATURE:
<223> OTHER INFORMATION: Down-Forward primer for ald gene deletion

<400> SEQUENCE: 51
caggactcga gtaccagcag accaagaacc tg        32

<210> SEQ ID NO 52
<211> LENGTH: 35
<212> TYPE: DNA
<213> ORGANISM: Artificial Sequence
<220> FEATURE:
<223> OTHER INFORMATION: Down-Reverse primer for ald gene deletion

<400> SEQUENCE: 52
aggtggatac ggatcgatct ccagaggttt caagc        35

<210> SEQ ID NO 53
<211> LENGTH: 38
<212> TYPE: DNA
<213> ORGANISM: Artificial Sequence

```
<220> FEATURE:
<223> OTHER INFORMATION: Up-Forward primer for ald gene deletion

<400> SEQUENCE: 53
gtgaattcga gctcgaacgc cagatggtcg tactttgc                              38

<210> SEQ ID NO 54
<211> LENGTH: 38
<212> TYPE: DNA
<213> ORGANISM: Artificial Sequence
<220> FEATURE:
<223> OTHER INFORMATION: Down-Reverse primer for ald gene deletion

<400> SEQUENCE: 54
aggtggatac ggatcttcaa caccgctgat ttcctacg                              38

<210> SEQ ID NO 55
<211> LENGTH: 39
<212> TYPE: DNA
<213> ORGANISM: Artificial Sequence
<220> FEATURE:
<223> OTHER INFORMATION: Forward primer for KnR gene

<400> SEQUENCE: 55
cggtaccgtc gacgatatcg aggtctgcct cgtgaagaa                             39

<210> SEQ ID NO 56
<211> LENGTH: 35
<212> TYPE: DNA
<213> ORGANISM: Artificial Sequence
<220> FEATURE:
<223> OTHER INFORMATION: Reverse primer for KnR gene

<400> SEQUENCE: 56
gcctttttac ggttcgattt attcaacaaa gccgc                                 35

<210> SEQ ID NO 57
<211> LENGTH: 35
<212> TYPE: DNA
<213> ORGANISM: Artificial Sequence
<220> FEATURE:
<223> OTHER INFORMATION: Forward primer for pUCori

<400> SEQUENCE: 57
gaaccgtaaa aaggccgcgt tgctggcgtt tttcc                                 35

<210> SEQ ID NO 58
<211> LENGTH: 35
<212> TYPE: DNA
<213> ORGANISM: Artificial Sequence
<220> FEATURE:
<223> OTHER INFORMATION: Reverse primer for pUCori

<400> SEQUENCE: 58
gcggccgcgt agaaaagatc aaaggatctt cttga                                 35

<210> SEQ ID NO 59
<211> LENGTH: 35
<212> TYPE: DNA
<213> ORGANISM: Artificial Sequence
<220> FEATURE:
<223> OTHER INFORMATION: Forward primer for pCG1ori

<400> SEQUENCE: 59
tttctacgcg gccgcccatg gtcgtcacag agctg                                 35
```

<210> SEQ ID NO 60
<211> LENGTH: 40
<212> TYPE: DNA
<213> ORGANISM: Artificial Sequence
<220> FEATURE:
<223> OTHER INFORMATION: Reverse primer for pCG1ori

<400> SEQUENCE: 60
tcgtcgacgg taccggatcc ttgggagcag tccttgtgcg                          40

<210> SEQ ID NO 61
<211> LENGTH: 35
<212> TYPE: DNA
<213> ORGANISM: Artificial Sequence
<220> FEATURE:
<223> OTHER INFORMATION: Forward primer for PgapA

<400> SEQUENCE: 61
ctgctcccaa ggatcgaaga aatttagatg attga                               35

<210> SEQ ID NO 62
<211> LENGTH: 39
<212> TYPE: DNA
<213> ORGANISM: Artificial Sequence
<220> FEATURE:
<223> OTHER INFORMATION: Reverse primer for PgapA

<400> SEQUENCE: 62
ccgtcgacga tatcatatgg tgtctcctct aaagattgt                           39

<210> SEQ ID NO 63
<211> LENGTH: 39
<212> TYPE: DNA
<213> ORGANISM: Artificial Sequence
<220> FEATURE:
<223> OTHER INFORMATION: Forward primer for TrrnB

<400> SEQUENCE: 63
tgatatcgtc gacggatcct gcctggcggc agtagcgcg                           39

<210> SEQ ID NO 64
<211> LENGTH: 35
<212> TYPE: DNA
<213> ORGANISM: Artificial Sequence
<220> FEATURE:
<223> OTHER INFORMATION: Reverse primer for TrrnB

<400> SEQUENCE: 64
gaggcagacc tcgataaaaa ggccatccgt cagga                               35

<210> SEQ ID NO 65
<211> LENGTH: 35
<212> TYPE: DNA
<213> ORGANISM: Artificial Sequence
<220> FEATURE:
<223> OTHER INFORMATION: Forward primer for Ec_hpaI

<400> SEQUENCE: 65
cgcgcggcag ccatatggaa aacagtttta aagcg                               35

<210> SEQ ID NO 66
<211> LENGTH: 37
<212> TYPE: DNA
<213> ORGANISM: Artificial Sequence
<220> FEATURE:
<223> OTHER INFORMATION: Reverse primer for Ec_hpaI

```
<400> SEQUENCE: 66
ggatcctcga gcatattaat acacgccggg cttaatc                                37

<210> SEQ ID NO 67
<211> LENGTH: 36
<212> TYPE: DNA
<213> ORGANISM: Artificial Sequence
<220> FEATURE:
<223> OTHER INFORMATION: Forward primer for Ec_hpaI

<400> SEQUENCE: 67
agaggagaca ccatatgggc agcagccatc atcatc                                 36

<210> SEQ ID NO 68
<211> LENGTH: 38
<212> TYPE: DNA
<213> ORGANISM: Artificial Sequence
<220> FEATURE:
<223> OTHER INFORMATION: Reverse primer for Ec_hpaI

<400> SEQUENCE: 68
ccgccaggca ggatccttaa tacacgccgg gcttaatc                               38

<210> SEQ ID NO 69
<211> LENGTH: 37
<212> TYPE: DNA
<213> ORGANISM: Artificial Sequence
<220> FEATURE:
<223> OTHER INFORMATION: Forward primer for PgapA-hpaI-TrrnB

<400> SEQUENCE: 69
gcctggaatt ctcgagaagg actgctccca aggatcg                                37

<210> SEQ ID NO 70
<211> LENGTH: 34
<212> TYPE: DNA
<213> ORGANISM: Artificial Sequence
<220> FEATURE:
<223> OTHER INFORMATION: Reverse primer for PgapA-hpaI-TrrnB

<400> SEQUENCE: 70
aagcctcttc ctcgatcttc acgaggcaga cctc                                   34

<210> SEQ ID NO 71
<211> LENGTH: 37
<212> TYPE: DNA
<213> ORGANISM: Artificial Sequence
<220> FEATURE:
<223> OTHER INFORMATION: Forward primer for PgapA-hpaI-TrrnB

<400> SEQUENCE: 71
aaatccagga ctcgagaagg actgctccca aggatcg                                37

<210> SEQ ID NO 72
<211> LENGTH: 34
<212> TYPE: DNA
<213> ORGANISM: Artificial Sequence
<220> FEATURE:
<223> OTHER INFORMATION: Reverse primer for PgapA-hpaI-TrrnB

<400> SEQUENCE: 72
tctgctggta ctcgatcttc acgaggcaga cctc                                   34

<210> SEQ ID NO 73
```

<211> LENGTH: 34
<212> TYPE: DNA
<213> ORGANISM: Artificial Sequence
<220> FEATURE:
<223> OTHER INFORMATION: Forward primer for Ec_rhmA

<400> SEQUENCE: 73
agaggagaca ccatatgaac gcattattaa gcaa                           34

<210> SEQ ID NO 74
<211> LENGTH: 41
<212> TYPE: DNA
<213> ORGANISM: Artificial Sequence
<220> FEATURE:
<223> OTHER INFORMATION: Reverse primer for Ec_rhmA

<400> SEQUENCE: 74
ccgccaggca ggatcagatc ttaataacta ccttttatgc g                   41

<210> SEQ ID NO 75
<211> LENGTH: 34
<212> TYPE: DNA
<213> ORGANISM: Artificial Sequence
<220> FEATURE:
<223> OTHER INFORMATION: Forward primer for Ec_nanA

<400> SEQUENCE: 75
agaggagaca ccatatggca acgaatttac gtgg                           34

<210> SEQ ID NO 76
<211> LENGTH: 38
<212> TYPE: DNA
<213> ORGANISM: Artificial Sequence
<220> FEATURE:
<223> OTHER INFORMATION: Reverse primer for Ec_nanA

<400> SEQUENCE: 76
ccgccaggca ggatccttac ccgcgctctt gcatcaac                       38

<210> SEQ ID NO 77
<211> LENGTH: 35
<212> TYPE: DNA
<213> ORGANISM: Artificial Sequence
<220> FEATURE:
<223> OTHER INFORMATION: Forward primer for pCASE1ori

<400> SEQUENCE: 77
tttctacgcg gccgccactg gaagggttct tcagg                          35

<210> SEQ ID NO 78
<211> LENGTH: 40
<212> TYPE: DNA
<213> ORGANISM: Artificial Sequence
<220> FEATURE:
<223> OTHER INFORMATION: Reverse primer for pCASE1ori

<400> SEQUENCE: 78
tcgtcgacgg taccggatcc ctgacttggt tacgatggac                     40

<210> SEQ ID NO 79
<211> LENGTH: 35
<212> TYPE: DNA
<213> ORGANISM: Artificial Sequence
<220> FEATURE:
<223> OTHER INFORMATION: Forward primer for PldhA

<400> SEQUENCE: 79
accaagtcag ggatcgcgga actagctctg caatg      35

<210> SEQ ID NO 80
<211> LENGTH: 39
<212> TYPE: DNA
<213> ORGANISM: Artificial Sequence
<220> FEATURE:
<223> OTHER INFORMATION: Reverse primer for PldhA

<400> SEQUENCE: 80
ccgtcgacga tatcatatgc gatcccactt cctgatttc      39

<210> SEQ ID NO 81
<211> LENGTH: 39
<212> TYPE: DNA
<213> ORGANISM: Artificial Sequence
<220> FEATURE:
<223> OTHER INFORMATION: Forward primer for SpR

<400> SEQUENCE: 81
cggtaccgtc gacgatatct ctagaccagc caggacaga      39

<210> SEQ ID NO 82
<211> LENGTH: 35
<212> TYPE: DNA
<213> ORGANISM: Artificial Sequence
<220> FEATURE:
<223> OTHER INFORMATION: Reverse primer for SpR

<400> SEQUENCE: 82
gcctttttac ggttcctcga gggttatttg ccgac      35

<210> SEQ ID NO 83
<211> LENGTH: 35
<212> TYPE: DNA
<213> ORGANISM: Artificial Sequence
<220> FEATURE:
<223> OTHER INFORMATION: Reverse primer for TrrnB

<400> SEQUENCE: 83
ggctggtcta gagataaaaa ggccatccgt cagga      35

<210> SEQ ID NO 84
<211> LENGTH: 34
<212> TYPE: DNA
<213> ORGANISM: Artificial Sequence
<220> FEATURE:
<223> OTHER INFORMATION: Forward primer for Pp_mdlC

<400> SEQUENCE: 84
cgcgcggcag ccatatggct tcggtacacg gcac      34

<210> SEQ ID NO 85
<211> LENGTH: 37
<212> TYPE: DNA
<213> ORGANISM: Artificial Sequence
<220> FEATURE:
<223> OTHER INFORMATION: Reverse primer for Pp_mdlC

<400> SEQUENCE: 85
ggatcctcga gcatatcact tcaccgggct tacggtg      37

<210> SEQ ID NO 86
<211> LENGTH: 34
<212> TYPE: DNA

```
<213> ORGANISM: Artificial Sequence
<220> FEATURE:
<223> OTHER INFORMATION: Forward primer for Pp_mdlC

<400> SEQUENCE: 86
agaggagaca ccatatggct tcggtacacg gcac                              34

<210> SEQ ID NO 87
<211> LENGTH: 36
<212> TYPE: DNA
<213> ORGANISM: Artificial Sequence
<220> FEATURE:
<223> OTHER INFORMATION: Reverse primer for Pp_mdlC

<400> SEQUENCE: 87
gtcgacgata tcatatcact tcaccgggct tacggt                            36

<210> SEQ ID NO 88
<211> LENGTH: 39
<212> TYPE: DNA
<213> ORGANISM: Artificial Sequence
<220> FEATURE:
<223> OTHER INFORMATION: Forward primer for Kp_dhaT

<400> SEQUENCE: 88
cgcgcggcag ccatatgagc tatcgtatgt tcgattatc                         39

<210> SEQ ID NO 89
<211> LENGTH: 38
<212> TYPE: DNA
<213> ORGANISM: Artificial Sequence
<220> FEATURE:
<223> OTHER INFORMATION: Reverse primer for Kp_dhaT

<400> SEQUENCE: 89
ggatcctcga gcatattaga atgcctggcg gaaaatcg                          38
```